US009074128B2

(12) United States Patent
Stoessel et al.

(10) Patent No.: US 9,074,128 B2
(45) Date of Patent: Jul. 7, 2015

(54) METAL COMPLEXES HAVING AZABOROL LIGANDS AND ELECTRONIC DEVICE HAVING THE SAME

(75) Inventors: Philipp Stoessel, Frankfurt (DE); Holger Heil, Frankfurt am Main (DE); Dominik Joosten, Frankfurt (DE); Christof Pflumm, Frankfurt (DE); Anja Gerhard, Egelsbach (DE)

(73) Assignee: Merck Patent GmbH (DE)

( * ) Notice: Subject to any disclaimer, the term of this patent is extended or adjusted under 35 U.S.C. 154(b) by 224 days.

(21) Appl. No.: 13/254,220

(22) PCT Filed: Feb. 3, 2010

(86) PCT No.: PCT/EP2010/000635
§ 371 (c)(1),
(2), (4) Date: Sep. 1, 2011

(87) PCT Pub. No.: WO2010/099852
PCT Pub. Date: Sep. 10, 2010

(65) Prior Publication Data
US 2012/0004407 A1 Jan. 5, 2012

(30) Foreign Application Priority Data
Mar. 2, 2009 (DE) .................. 10 2009 011 223

(51) Int. Cl.
*C07F 15/00* (2006.01)
*C07F 5/02* (2006.01)
*C09K 11/06* (2006.01)
*H01L 51/50* (2006.01)
*C09B 57/10* (2006.01)
*H01L 51/00* (2006.01)

(52) U.S. Cl.
CPC ............. *C09K 11/06* (2013.01); *C07F 5/022* (2013.01); *C07F 15/0033* (2013.01); *C07F 15/004* (2013.01); *C07F 15/0086* (2013.01); *C07F 15/0093* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1055* (2013.01); *C09K 2211/1059* (2013.01); *C09K 2211/185* (2013.01); *H01L 51/006* (2013.01); *H01L 51/0081* (2013.01); *H01L 51/0085* (2013.01); *H01L 51/0087* (2013.01); *H01L 51/5012* (2013.01); *C09B 57/10* (2013.01); *Y02E 10/549* (2013.01)
USPC ........................................... 548/110; 548/101

(58) Field of Classification Search
CPC ............ C09K 11/06; C09K 2211/183; C09K 2211/185; C09K 2211/186; H01L 51/0079; H01L 51/0084; H01L 51/0091; H01L 51/5012; C07F 15/0013; C07F 1/005
USPC ................................................. 548/101, 110
See application file for complete search history.

(56) References Cited

U.S. PATENT DOCUMENTS

| | | | |
|---|---|---|---|
| 4,539,507 A | 9/1985 | VanSlyke et al. |
| 5,151,629 A | 9/1992 | VanSlyke |
| 5,621,131 A | 4/1997 | Kreuder et al. |
| 5,840,217 A | 11/1998 | Lupo et al. |
| 6,458,909 B1 | 10/2002 | Spreitzer et al. |
| 6,653,438 B1 | 11/2003 | Spreitzer et al. |
| 7,109,345 B1 | 9/2006 | Ortiz-Marciales et al. |
| 2005/0069729 A1 | 3/2005 | Ueda et al. |
| 2006/0175958 A1 | 8/2006 | Gerhard et al. |
| 2006/0208221 A1 | 9/2006 | Gerhard et al. |
| 2006/0255332 A1 | 11/2006 | Becker et al. |
| 2006/0284140 A1 | 12/2006 | Breuning et al. |
| 2007/0060736 A1 | 3/2007 | Becker et al. |
| 2007/0176147 A1 | 8/2007 | Buesing et al. |
| 2007/0205714 A1 | 9/2007 | Busing et al. |
| 2007/0249834 A1 | 10/2007 | Stoessel et al. |
| 2008/0027220 A1 | 1/2008 | Stoessel et al. |
| 2009/0134384 A1 | 5/2009 | Stoessel et al. |
| 2009/0167166 A1 | 7/2009 | Bach et al. |
| 2009/0226759 A1 | 9/2009 | Heun et al. |
| 2009/0302742 A1 | 12/2009 | Komori et al. |
| 2009/0302752 A1 | 12/2009 | Parham et al. |
| 2010/0102305 A1 | 4/2010 | Heun et al. |
| 2010/0187977 A1 | 7/2010 | Kai et al. |

(Continued)

FOREIGN PATENT DOCUMENTS

DE 102008033943 A1 1/2010
DE 102008036982 A1 2/2010

(Continued)

OTHER PUBLICATIONS

Kajiwara et al., Angew. Chem. Int. Ed., vol. 47, pp. 6606-6610 (published online Jul. 21, 2008).*
Segawa et al., Angew. Chem. Int. Ed., vol. 46, pp. 6710-6713 (2007).*
Terabayashi et al., Journal of American Chemical Society, vol. 131, No. 40, pp. 14162-14163 (published online Sep. 23, 2009).*
Suginome et al., Organometalllics, vol. 25, No. 12, pp. 2911-2913 (2006).*
Käpplinger, C., et al., "New Tetraazafulvadienes Via Cascade Reactions and Their Cyclizations to Diazaborolidines," *Tetrahedron*, vol. 60, pp. 3847-3853 (2004).

(Continued)

*Primary Examiner* — Porfirio Nazario Gonzalez
(74) *Attorney, Agent, or Firm* — Drinker Biddle & Reath LLP

(57) ABSTRACT

The present invention relates to an electronic device, in particular an organic electroluminescent device, which comprises metal complexes containing azaborole ligands. The invention also relates to the metal complexes themselves, to the use thereof in an organic electronic device, and to a process for the preparation thereof. Finally, the invention is directed to the ligands and to the use of the ligands for the preparation of the metal complexes according to the invention.

15 Claims, No Drawings

(56) References Cited

U.S. PATENT DOCUMENTS

| | | |
|---|---|---|
| 2010/0227978 A1 | 9/2010 | Stoessel et al. |
| 2010/0244009 A1 | 9/2010 | Parham et al. |
| 2010/0288974 A1 | 11/2010 | Buesing et al. |
| 2010/0331506 A1 | 12/2010 | Fortte et al. |
| 2011/0012100 A1 | 1/2011 | Stoessel |
| 2011/0068304 A1 | 3/2011 | Parham et al. |
| 2011/0121274 A1 | 5/2011 | Parham et al. |
| 2011/0140043 A1 | 6/2011 | Stoessel et al. |
| 2012/0200808 A1 | 8/2012 | Yamamoto et al. |

FOREIGN PATENT DOCUMENTS

| | | |
|---|---|---|
| EP | 0 652 273 A1 | 5/1995 |
| EP | 0 676 461 A2 | 10/1995 |
| EP | 0 707 020 A2 | 4/1996 |
| EP | 0 842 208 A1 | 5/1998 |
| EP | 0 894 107 | 2/1999 |
| EP | 1 028 136 A2 | 8/2000 |
| EP | 1 191 612 A2 | 3/2002 |
| EP | 1 191 613 A2 | 3/2002 |
| EP | 1 191 614 A2 | 3/2002 |
| EP | 1 205 527 A1 | 5/2002 |
| EP | 1 617 710 A1 | 1/2006 |
| EP | 1 617 711 A1 | 1/2006 |
| EP | 1 731 584 A1 | 12/2006 |
| JP | 2004288381 | 10/2004 |
| JP | 2005347160 | 12/2005 |
| JP | 2007 162008 A | 6/2007 |
| WO | WO-92/18552 A1 | 10/1992 |
| WO | WO-97/05184 A1 | 2/1997 |
| WO | WO-97/39045 A1 | 10/1997 |
| WO | WO-98/27136 A1 | 6/1998 |
| WO | WO-00/22026 A1 | 4/2000 |
| WO | WO-00/70655 A2 | 11/2000 |
| WO | WO-01/41512 A1 | 6/2001 |
| WO | WO-02/02714 A2 | 1/2002 |
| WO | WO-02/15645 A1 | 2/2002 |
| WO | WO-2004/013080 A1 | 2/2004 |
| WO | WO-2004/041901 A1 | 5/2004 |
| WO | WO-2004/070772 A2 | 8/2004 |
| WO | WO-2004/081017 A1 | 9/2004 |
| WO | WO-2004/093207 A2 | 10/2004 |
| WO | WO-2004/113412 A2 | 12/2004 |
| WO | WO-2004/113468 A1 | 12/2004 |
| WO | WO-2005/003253 A2 | 1/2005 |
| WO | WO-2005/011013 A1 | 2/2005 |
| WO | WO-2005/014689 A2 | 2/2005 |
| WO | WO-2005/033244 A1 | 4/2005 |
| WO | WO-2005/039246 A1 | 4/2005 |
| WO | WO-2005/040302 A1 | 5/2005 |
| WO | WO-2005/104264 A1 | 11/2005 |
| WO | WO-2005/111172 A2 | 11/2005 |
| WO | WO-2005/113563 A1 | 12/2005 |
| WO | WO-2006/005627 A1 | 1/2006 |
| WO | WO-2006/008069 A1 | 1/2006 |
| WO | WO-2006/061181 A1 | 6/2006 |
| WO | WO-2006/117052 A1 | 11/2006 |
| WO | WO-2007/017066 A1 | 2/2007 |
| WO | WO-2007/063754 A1 | 6/2007 |
| WO | WO-2007/137725 A1 | 12/2007 |
| WO | WO-2008/056746 A1 | 5/2008 |
| WO | WO-2008/086851 A1 | 7/2008 |
| WO | WO-2009/062578 A1 | 5/2009 |
| WO | WO-2009/118087 A1 | 10/2009 |

OTHER PUBLICATIONS

Engstrom, K.M., et al., "Synthesis of the Glucuronide Metabolite of ABT-751," *Tetrahedron Letters*, vol. 48, pp. 1359-1362 (2007).

Segawa, Y., et al., "Chemistry of Boryllithium: Synthesis, Structure, and Reactivity," *J. Am. Chem. Soc.*, vol. 130, pp. 16069-16079 (2008).

Chinese Office Action for Invention No. 201080007829.4, received May 29, 2013 by Merck Patent GmbH.

Cruz, A., et al., "1,3 Heterazolidin-2-ones as starting materials for optically active 1,3,2-oxazaborolines and 1,3,2,-diazaboroline derived from ephedrines", Tetrahedron Asymmetry, vol. 9 (1998), pp. 3991-3996.

Cruz, A., et al., "Thiazaborolidines and $BH_3$ Adducts Derived From Thioephedrines", Tetrahedron: Asymmetry, vol. 6, No. 8, (1995), pp. 1933-1940.

Segawa, Y., et al., "Boryl Anion Attacks Transition-Metal Chlorides To Form Boryl Complexes: Syntheses, Spectroscopic, and Structural Studies on Group II Borylmetal Complexes", Angew Chem., vol. 119, (2007), pp. 6830-6833.

Weber, L., et al., "Chiral 2,3-Dihydro-1H-1,3,2-diazaboroles", Eur. J. lnorg. Chem., (2002), pp. 2438-2446.

Weber, L., et al., "Synthesis and Structure of 2-Hydro-, 2-Alkyl-, 2-Alkynyl, and 2-Stannyl1-2-3-dihydro-1H-1,3,2-diazaboroles", Eur. J. lnorg. Chem., (1999), pp. 491-497.

Toumelin, J-B., et al., "Chiral Intramolecular Amine-Borane Complexes as Reducing Agents for Prochiral Ketones", Tetrahedron; Asymmetry, vol. 8, No. 8, (1997), pp. 1259-1265.

Tlahuext, H., et al., "N-Alkyloxazaborolidines Derived from Ephedrines", Tetradehron: Asymmetry, vol. 3, No. 6, (1992), pp. 727-730.

Weber, L., "Contribution to the Reactivity of $N,N'$-Diaryl-1,4,diazabutadienes Aryl-N=CH-CH=N-Aryl (Aryl = 2,6-Dimethylphenly; 2,4,6-Trimethylphenyl) Towards Boron Trichloride", Eur. J. Inorg. Chem., (2006), pp. 5048-5056.

Berenguer, R., et al., "Enantioselective Reduction of Acetophenone with 1,3,2-Oxazaborolidines Derived from Ephedrine, Pseudoephedrine, and Phenylglycine", Tetrahedron: Asymmety, vol. 4, No. 1, (1993), pp. 13-16.

Weber, L., Recent Developments in the Chemistry of 1,3,2-diazaborolines-(2,3-dyhydro-1H-1,3,2-diazaboroles), Coordination Chemistry Reviews, vol. 252, (2008), pp. 1-31.

Segawa, Y., et al., "Chemistry of Boryllithium: Synthesis, Structure, and Reactivity", J. Am. Chem. Soc., vol. 130; (2006), pp. 16069-16079.

\* cited by examiner

METAL COMPLEXES HAVING AZABOROL LIGANDS AND ELECTRONIC DEVICE HAVING THE SAME

RELATED APPLICATIONS

This application is a national stage application (under 35 U.S.C. §371) of PCT/EP2010/000635, filed Feb. 3, 2010, which claims benefit of German Application No. 10 2009 011 223.5, filed Mar. 2, 2009.

The present invention relates to an electronic device which comprises metal complexes of the formula I. The invention also relates to the metal complexes themselves, to the use thereof in an electronic device, and to a process for the preparation thereof. The invention is furthermore directed to the ligands and to the use of the ligands for the preparation of the metal complexes according to the invention.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organo-metallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in the case of OLEDs which exhibit triplet emission. Thus, the physical properties of phosphorescent OLEDs are still inadequate in respect of the stability of the metal complexes, efficiency, operating voltage and lifetime for use of triplet emitters in high-quality and long-lived electroluminescent devices. This applies, in particular, to blue-emitting triplet emitters. Further improvements are therefore desirable here. There is also still a need for improvement in the case of other compounds used in organic electroluminescent devices, such as, for example, matrix materials and charge-transport materials.

In accordance with the prior art, iridium complexes containing bidentate ligands which coordinate via C and N are usually employed as triplet emitters in phosphorescent OLEDs. It has been possible to achieve an improvement in these OLEDs by employing metal complexes containing polypodal ligands or cryptates, which means that the complexes have higher thermal stability, which results in a longer lifetime of the OLEDs (WO 04/081017, WO 05/113563, WO 06/008069). However, further improvements in the complexes are still desirable in order to be able to employ the latter in high-quality and long-lived electroluminescent devices, for example for televisions or computer monitors.

Metal complexes are also employed in other functions in organic electroluminescent devices, for example Alq$_3$ (aluminium tris(hydroxyquinolinate)) is employed as electron-transport material or BAlq (for example T. Tsuji et al., *Journal of the Society of Information Display* 2005, 13(2), 117-122) is employed as triplet matrix material, as hole-blocking material or as electron-transport material. Zinc complexes are also used as triplet matrix materials (for example WO 09/062578, EP 652273). Further improvements are also still desirable in the case of these materials for use thereof in high-quality electroluminescent devices.

The object of the present invention is therefore the provision of novel organic electroluminescent devices comprising metal complexes. The metal complexes can be employed here as emitters, as matrix materials, as hole-blocking materials, as electron-transport materials or also in other functions in the OLEDs. There is still a need for improvement in the case of red-, green- and blue-phosphorescent metal complexes, in particular in the case of blue-phosphorescent metal complexes.

Surprisingly, it has been found that certain organic electroluminescent devices which comprise the metal chelate complexes described in greater detail below achieve this object and result in significant improvements in the organic electroluminescent device, in particular with respect to the lifetime, the efficiency and the emission colour. This applies, in particular, to green- and blue-phosphorescent electroluminescent devices. The present invention therefore relates to organic electroluminescent devices which comprise these complexes. The present invention furthermore relates to particularly suitable metal complexes which can be used in organic electroluminescent devices.

The invention therefore provides an electronic device comprising a compound of the general formula I

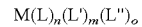

where the compound of the general formula I contains a moiety $M(L)_n$ of the formula II and/or III and/or IV:

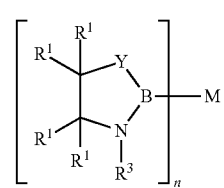

formula II

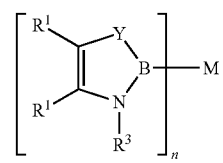

formula III

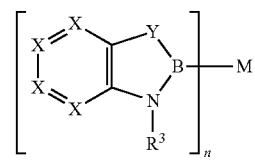

formula IV where the following applies to the symbols and indices used:
M is a metal;
Y is on each occurrence, in each case independently of one another, NR$^3$, O or S;
X is on each occurrence, in each case independently of one another, CR$^1$ or N;
R$^1$ is on each occurrence, in each case independently of one another, H, D, F, Cl, Br, I, CHO, N(R$^2$)$_2$, N(Ar)$_2$, C(=O) Ar, P(=O)(Ar)$_2$, S(=O)Ar, S(=O)$_2$Ar, CR$^2$=CR$^2$)$_2$, CR$^2$=CR$^2$Ar, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thio-alkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C=O, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or hetero-aromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where two or more adjacent substituents $R^1$ may also form a mono- or polycyclic, aliphatic or aromatic ring system with one another;

$R^2$ is on each occurrence, in each case independently of one another, H, D, F or an aliphatic, aromatic and/or heteroaromatic hydrocarbon radical having 1 to 20 C atoms, in which, in addition, one or more H atoms may be replaced by F; two or more substituents $R^2$ here may also form a mono- or polycyclic, aliphatic or aromatic ring system with one another;

$R^3$ is on each occurrence, in each case independently of one another, H, D, an aliphatic hydrocarbon radical having 1 to 20 C atoms or an aromatic or heteroaromatic ring system having 5 to 30 aromatic ring atoms, which may be substituted by one or more radicals $R^1$; or $R^3$ is a coordinating group, where $R^3$ bonds to the metal M via a charged or uncharged exocyclic or endocyclic donor atom D;

a plurality of part-ligands L here may form a polydentate or polypodal ligand with one another or L together with L' and/or L", optionally via a link via $R^3$;

Ar is on each occurrence, in each case independently of one another, an aromatic or heteroaromatic ring system having 5 to 30 aromatic ring atoms, which may be substituted by one or more non-aromatic radicals $R^1$;

L', L" are any desired co-ligands;

where furthermore n=1 to 6 (1, 2, 3, 4, 5, 6), o=0 to 5 (0, 1, 2, 3, 4, 5) and m=0 to 5 (0, 1, 2, 3, 4, 5) if M has the coordination number 6, and n=1 to 5 (1, 2, 3, 4, 5), o=0 to 4 (0, 1, 2, 3, 4) and m=0 to 4 (0, 1, 2, 3, 4) if M has the coordination number 5, and n=1 to 4 (1, 2, 3, 4), m=0 to 3 (0, 1, 2, 3) and o=0 to 3 (0, 1, 2, 3) if M has the coordination number 4.

In the moiety $M(L)_n$, L denotes a ligand, which is represented in the square brackets in the formulae II, III and IV.

The indices n, m and o here are selected so that the coordination number on the metal M in total corresponds, depending on the metal, to the usual coordination number for this metal. For transition metals, this is, depending on the metal, usually the coordination number 4, 5 or 6, preferably 4 or 6. It is generally known that metal coordination compounds have different coordination numbers depending on the metal and on the oxidation state of the metal, i.e. bond a different number of ligands. Since the preferred coordination numbers of metals and metal ions in various oxidation states are part of the general expert knowledge of the person skilled in the art in the area of organometallic chemistry or coordination chemistry, it is straightforward for the person skilled in the art to use a suitable number of ligands L, L' and/or L", depending on the metal and its oxidation state and depending on the precise structure of the ligand of the formula II, III or IV, and thus to make a suitable choice of the indices n, m and o.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

For the purposes of this invention, a cyclic carbene is a cyclic group which bonds to the metal via a neutral C atom.

The cyclic group here may be saturated or unsaturated. Preference is given here to Arduengo carbenes, i.e. carbenes in which two nitrogen atoms are bonded to the carbene C atom. For the purposes of this invention, a five-membered Arduengo carbene ring or another unsaturated five-membered carbene ring is likewise regarded as being an aryl group.

For the purposes of this invention, an aromatic ring system contains 6 to 60 C atoms in the ring system. For the purposes of this invention, a heteroaromatic ring system contains 1 to 59 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as 9,9'-spirobifluorene, 9,9-diarylfluorene, triarylamine, diaryl ether, stilbene, etc., are also intended to be taken to mean aromatic ring systems for the purposes of this invention, as are systems in which two or more aryl groups are interrupted, for example, by a linear or cyclic alkyl group or by a silyl group.

An aromatic or heteroaromatic ring system having 5-60 aromatic ring atoms, which may also in each case be substituted by the radicals $R^1$ to $R^3$ mentioned above and which may be linked to the aromatic or heteroaromatic ring system via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, an alkyl group having 1 to 40 C atoms or a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. For the purposes of the present invention, an alkenyl group is taken to mean, for example, ethenyl, propenyl, butenyl, pentenyl, cyclopentenyl, hexenyl, cyclohexenyl, heptenyl, cycloheptenyl, octenyl or cyclooctenyl. For the purposes of the present invention, an alkynyl group is taken to mean, for example, ethynyl, propynyl, butynyl, pentynyl, hexynyl, heptynyl or octynyl. A $C_1$- to $C_{40}$-alkoxy group or an alkoxy group having 1 to 40 C atoms is taken to mean, for example, methoxy, trifluoromethoxy, ethoxy, n-propoxy, i-propoxy, n-butoxy, i-butoxy, s-butoxy, t-butoxy or 2-methylbutoxy.

For the purposes of the present invention, a donor atom is taken to mean an atom which has at least one free electron pair and is thus capable of bonding to a metal atom or metal ion. The donor atom here may be neutral or negatively or positively charged. The donor atom is preferably neutral or negatively charged. Examples of neutral donor atoms are nitrogen which is bonded in a heteroaromatic compound, such as, for example, pyridine, or which is in the form of an imine, or carbon in the form of a carbene. Examples of anionic donor atoms are carbon which is part of an aromatic or heteroaromatic group, such as, for example, a carbon atom in a phenyl group, or nitrogen which is part of a five-membered heteroaromatic group, such as, for example, nitrogen in pyrrole which bonds via the nitrogen. For the purposes of this invention, an exocyclic donor atom D is taken to mean a donor atom which is not part of a cyclic substituent $R^3$ or of the cyclic group Cy1, as defined below, but instead is bonded as substituent to $R^3$ or Cy1 and has at least one free electron pair and is thus capable of bonding to a metal atom. Examples of exocyclic donor atoms are oxygen in the form of a phenolate, sulfur in the form of a thiolate, nitrogen in the form of a nitrile, amine, imine, amide or imide, phosphorus in the form of a phosphine or phosphite or carbon in the form of an isonitrile or acetylide.

In an embodiment of the invention, it is preferred for the moiety $M(L)_n$ to conform to the formula IIa, IIIa, IVa, IIb, IIIb or IVb:

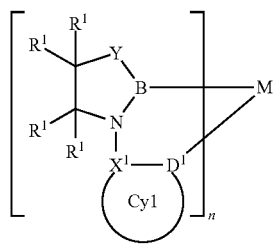
formula IIa

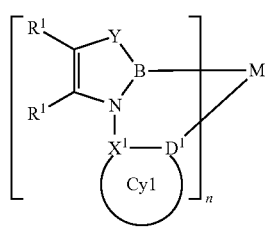
formula IIIa

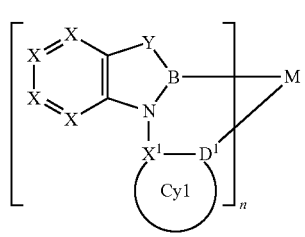
formula IVa

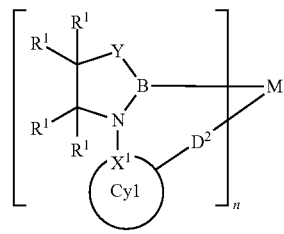
formula IIb

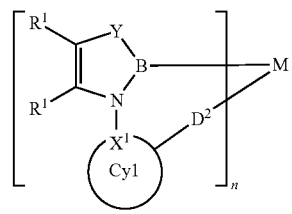
formula IIIb

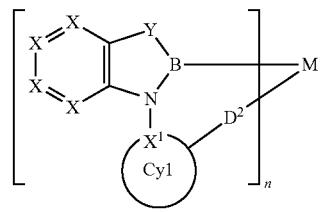
formula IVb where the symbols and indices have the meanings indicated above, and furthermore:

$D^1$ is on each occurrence, in each case independently of one another, an endocyclic donor atom selected from the group consisting of B, C, N, O and S;

$D^2$ is on each occurrence, in each case independently of one another, an exocyclic donor group selected from the group consisting of O, S, $NR^1$, $N(R^1)_2$, $PR^1$, $P(R^1)_2$, $P(O)R^1$, $P(O)(R^1)_2$, $AsR^1$, $As(R^1)_2$, $As(O)R^1$, $As(O)(R^1)_2$, $SbR^1$, $Sb(R^1)_2$, $Sb(O)R^1$, $Sb(O)(R^1)_2$, $BiR^2$, $Bi(R^1)_2$, $Bi(O)R^1$, $Bi(O)(R^1)_2$, $OR^1$, $SR^1$, $SeR^1$ and $TeR^1$;

$X^1$ is on each occurrence, in each case independently of one another, C or N;

Cy1 is on each occurrence, in each case independently of one another, an aromatic or heteroaromatic group or an aromatic or heteroaromatic ring system having 5 to 30 ring atoms, where $X^1$ and $D^1$ are present in the aromatic or heteroaromatic group or the aromatic or heteroaromatic ring system, or $D^2$ is bonded as an exocyclic group.

In an embodiment of the invention, it is preferred for $D^1$ to be on each occurrence, in each case independently of one another, an endocyclic donor atom selected from N, C, O or S.

In a further embodiment of the invention, it is preferred for $D^2$ to be on each occurrence, in each case independently of one another, an exocyclic donor group selected from O, S, $NR^1$, $N(R^1)_2$, $PR^1$, $P(R^1)_2$, where $R^1$ has the meaning indicated above.

Particular preference is given to structures of the formulae IIa, IIIa and IVa given above in which $D^1$ stands for N or C.

In a further embodiment of the invention, it is preferred in the compounds of the general formula II, III or IV or IIa, IIIa or IVa or IIb, IIIb or IVb for all groups Y to be identical and for all groups $R^3$ and Cy1 to be identical and for all groups Ar to be identical and for all groups $X^1$ to be identical.

For the purposes of this invention, preference is furthermore given to electronic devices where $R^3$ in the formulae II, III and IV or Cy1 in the formulae IIa, IIIa and IVa is selected from the following structures (1) to (24):
(1) 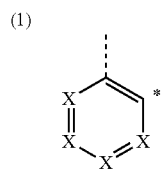
(2) 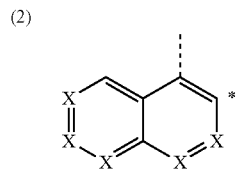
(3) 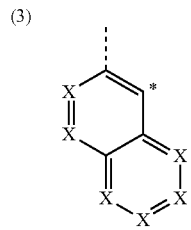
(4) 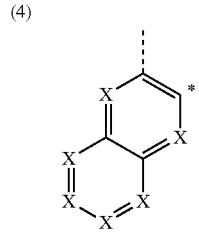
(5) 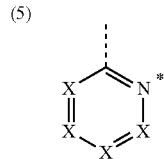
(6) 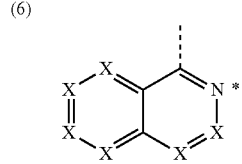
(7) 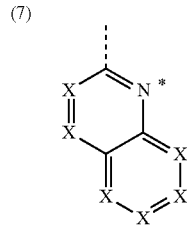
(8) 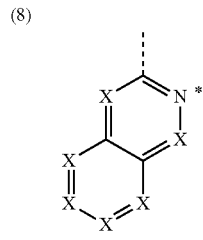
-continued
(9) 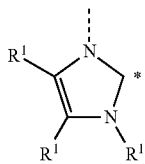
(10) 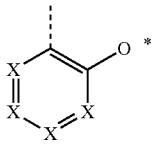
(11) 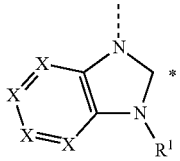
(12) 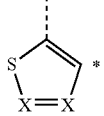
(13) 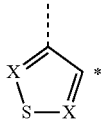
(14) 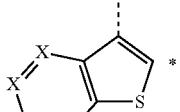
(15) 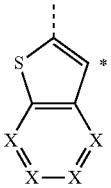
(16) 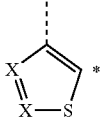
(17) 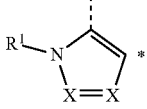

-continued

(18) 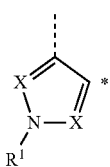

(19) 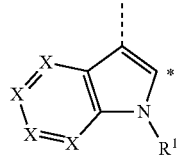

(20) 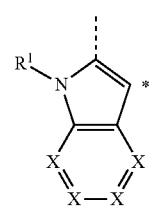

(21) 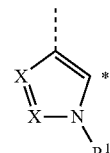

(22) 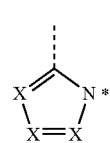

(23) 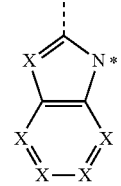

(24) 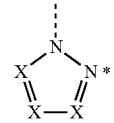

where X is on each occurrence, in each case independently of one another, $CR^1$ or N, $R^1$ has the meaning indicated above, the dashed line denotes a bond to the nitrogen atom of the boron/nitrogen heterocycle, and * denotes the coordination site on the metal.

In a further embodiment of the invention, it is preferred for Y in the compounds of the general formulae II, III and IV to be $NR^3$.

The metal M is preferably intended to be taken to mean a transition metal or a main-group metal. M is preferably a transition metal selected from Zr, Hf, Mo, W, Re, Ru, Os, Rh, Ir, Pd, Pt, Cu, Ag and Au. The metal can be in various oxidation states. The above-mentioned metals are preferably in the oxidation states Zr(IV), Hf(IV), Mo(II), Mo(III), Mo(IV), W(II), W(III), W(IV), Re(I), Re(II), Re(III), Re(IV), Ru(II), Ru(III), Os(II), Os(III), Os(IV), Rh(I), Rh(III), Ir(I), Ir(III), Ir(IV), Pd(II), Pt(II), Pt(IV), Cu(I), Cu(II), Cu(III), Ag(I), Ag(III), Au(I), Au(III) and Au(V). Particular preference is given to Ir(III), Pt(II) and Cu(I). M is furthermore preferably a main-group metal selected from alkali metals (Li, Na, K, Rb, Cs), alkaline-earth metals (Be, Mg, Ca, Sr, Ba), Al, Sn, Ge, Bi and Te.

Embodiments which are furthermore preferred are the structures IIc, IIIc and IVc:

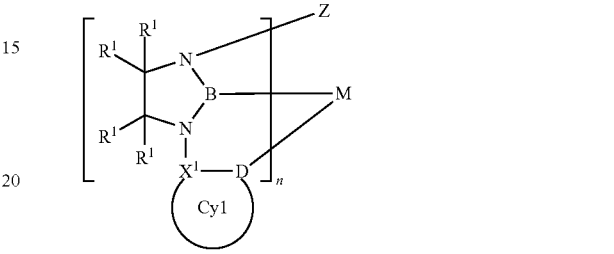

formula IIc

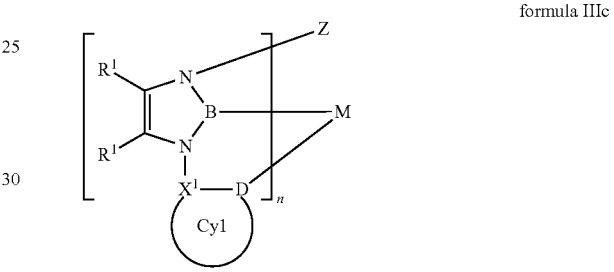

formula IIIc

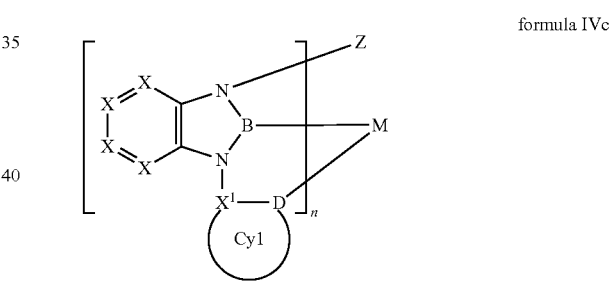

formula IVc where the symbols and indices used have the meanings indicated above, and Z stands for any desired bridging unit.

Entirely analogously, a plurality of ligands L in the structures IIb, IIIb and IVb) given above can be connected to one another by a group Z.

In a particularly preferred embodiment, the moiety $M(L)_n$ is selected from the following structures (25) to (30):

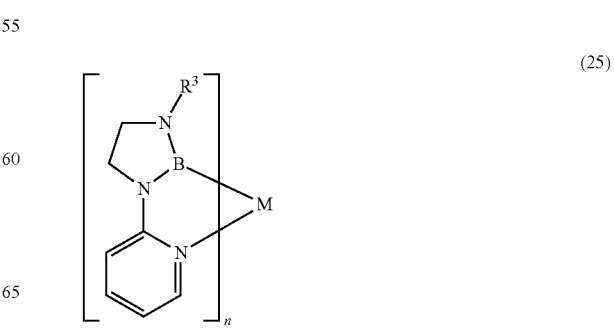

(25)

-continued

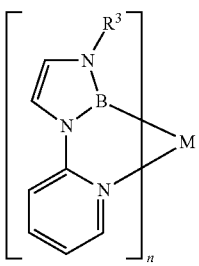 (26)

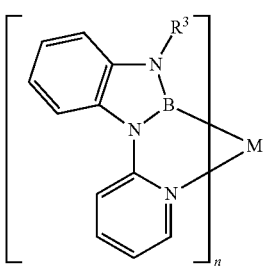 (27)

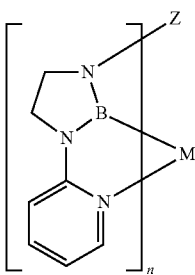 (28)

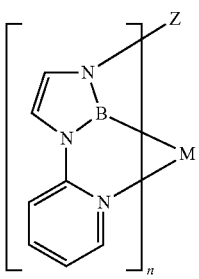 (29)

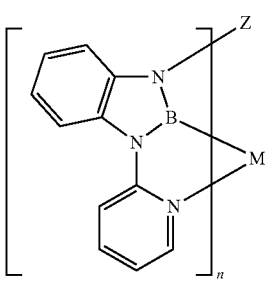 (30)

where the pyridine ring may in each case also be substituted by one or more radicals $R^1$. The index n here is selected in accordance with the coordination number of the metal M and depending on the presence of further co-ligands L' and L". Z here is any desired bridging unit. Since the job of Z is to link the ligands, however, Z only plays a secondary role for the electronic properties of the complex, and the precise structure of Z is unimportant.

If n=3, Z preferably stands for B, $B(R^1)^-$, $B(C(R^1)_2)_3$, $(R^1)B(C(R^1)_2)_3^-$, $B(O)_3$, $(R^1)B(O)_3^-$, $B(C(R^1)_2C(R^1)_2)_3$, $(R^1)B(C(R^1)_2C(R^1)_2)_3^-$, $B(C(R^1)_2O)_3$, $(R^1)B(C(R^1)_2O)_3^-$, $B(OC(R^1)_2)_3$, $(R^1)B(OC(R^1)_2)_3^-$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2C(R^1)_2)_3$, $(R^1)Si(C(R^1)_2Si(R^1)_2)_3$, $(R^1)Si(Si(R^1)_2Si(R^1)_2)_3$, N, NO, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)^+$, P, $P(R^1)^+$, PO, PS, PSe, PTe, $P(O)_3$, $PO(O)_3$, $P(OC(R^1)_2)_3$, $PO(OC(R^1)_2)_3$, $P(C(R^1)_2)_3$, $P(C(R^1)_2)_3$, $P(R^1)(C(R^1)_2)_3^+$, $PO(C(R^1)_2)_3$, $P(C(R^1)_2C(R^1)_2)_3$, $P(R^1)(C(R^1)_2C(R^1)_2)_3^+$, $PO(C(R^1)_2C(R^1)_2)_3$, As, $As(R^1)^+$, AsO, AsS, AsSe, AsTe, $As(O)_3$, $AsO(O)_3$, $As(OC(R^1)_2)_3$, $AsO(OC(R^1)_2)_3$, $As(C(R^1)_2)_3$, $As(R^1)(C(R^1)_2)_3^+$, $AsO(C(R^1)_2)_3$, $As(C(R^1)_2C(R^1)_2)_3$, $As(R^1)(C(R^1)_2C(R^1)_2)_3^+$, $AsO(C(R^1)_2C(R^1)_2)_3$, Sb, $Sb(R^1)^+$, SbO, SbS, SbSe, SbTe, $Sb(O)_3$, $SbO(O)_3$, $Sb(OC(R^1)_2)_3$, $SbO(OC(R^1)_2)_3$, $Sb(C(R^1)_2)_3$, $Sb(R^1)(C(R^1)_2)_3^+$, $SbO(C(R^1)_2)_3$, $Sb(C(R^1)_2C(R^1)_2)_3$, $Sb(R^1)(C(R^1)_2C(R^1)_2)_3^+$, $SbO(C(R^1)_2C(R^1)_2)_3$, Bi, $Bi(R^1)^+$, BiO, BiS, BiSe, BiTe, $Bi(O)_3$, $BiO(O)_3$, $Bi(OC(R^1)_2)_3$, $BiO(OC(R^1)_2)_3$, $Bi(C(R^1)_2)_3$, $Bi(R^1)(C(R^1)_2)_3^+$, $BiO(C(R^1)_2)_3$, $Bi(C(R^1)_2C(R^1)_2)_3$, $Bi(R^1)(C(R^1)_2C(R^1)_2)_3^+$, $BiO(C(R^1)_2C(R^1)_2)_3$, $S^+$, $S(C(R^1)_2)_3^+$, $S(C(R^1)_2C(R^1)_2)_3^+$, $Se^+$, $Se(C(R^1)_2)_3^+$, $Se(C(R^1)_2C(R^1)_2)_3^+$, $Te^+$, $Te(C(R^1)_2)_3^+$, $Te(C(R^1)_2C(R^1)_2)_3^+$ or a unit of the formula (31), (32), (33) or (34):

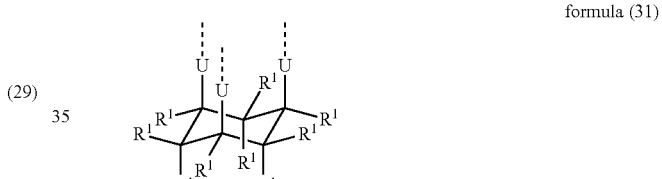
formula (31)

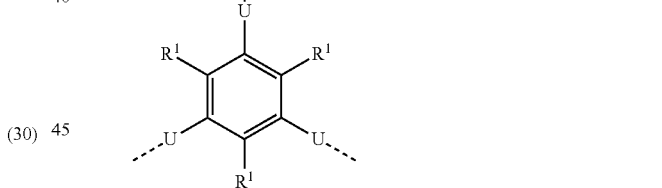
formula (32)

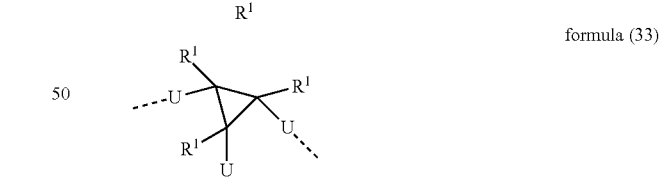
formula (33)

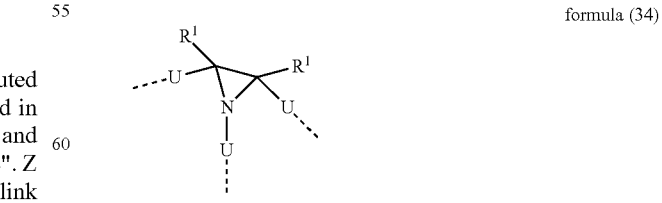
formula (34)

where the dashed bonds in each case indicate the bond to the part-ligands L, L' and L", and U is selected, identically or differently on each occurrence, from the group consisting of a single bond, O, S, S(=O), $S(=O)_2$, $NR^2$, $PR^2$, $P(=O)R^2$, $P(=NR^2)$, $C(R^2)_2$, $C(=O)$, $C(=NR^2)$, $C(=C(R^2)_2)$, $Si(R^2)_2$ and $BR^2$. The other symbols used have the meanings indicated above.

If Z is a divalent group, i.e. bridges two ligands L or L and L' or L' to one another, Z is preferably selected from the group consisting of $BR^1$, $B(R^1)_2^-$, $C(R^1)_2$, $C(=O)$, $Si(R^1)_2$, $NR^1$, $PR^1$, $P(R^1)_2^+$, $PO(R^1)$, $PS(R^1)$, $AsR^1$, $AsO(R^1)$, AsS, O, S, Se, or a unit of the formulae (35) to (43):

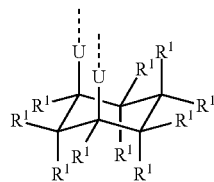

formula (35)

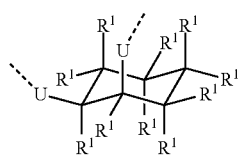

formula (36)

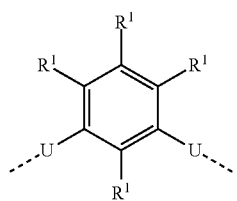

formula (37)

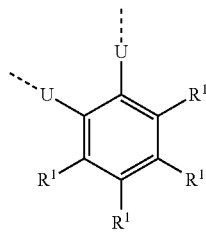

formula (38)

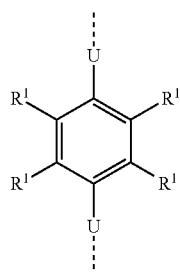

formula (39)

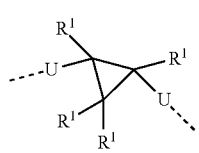

formula (40)

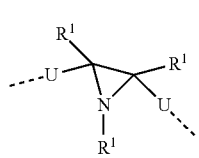

formula (41)

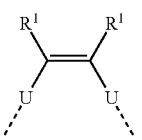

formula (42)

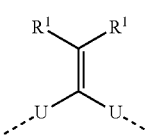

formula (43)

where the dashed bonds in each case indicate the bond to the part-ligands L or L' or L", and the other symbols used in each case have the meanings indicated above.

It is furthermore possible for more than one bridging unit Z to be present in the molecule, in particular two bridging units Z. If more than one bridging unit Z is present in the molecule, these groups Z may be identical or different. Thus, the formation of macrocyclic ligands or cryptands is possible with two bridging units Z.

It is preferred here for L' and/or L" to denote neutral, monoanionic, dianionic or trianionic ligands, preferably neutral or monoanionic ligands. L' and/or L" can be monodentate, bidentate, tridentate, tetradentate or pentadentate ligands.

In an embodiment of the invention, it is preferred for the compound of the general formula I in the electronic device to contain only ligands L according to the invention. These can be monodentate, bidentate or tridentate ligands, i.e. n=4 in the case of a tetracoordinated metal in the general formula I, n=6 in the case of a hexacoordinated metal, if L is a monodentate ligand. In the case of a tetracoordinated metal, the compound of the general formula I can contain four monodentate ligands or two bidéntate ligands or one tridentate ligand and one monodentate ligand or one tetradentate ligand. In the case of an octahedral complex, the compound of the general formula I can contain six monodentate ligands or three bidentate ligands or two tridentate ligands or one hexadentate ligand. Combinations of mono-, bi-, tri-, tetra- and pentadentate ligands are likewise possible if the coordination number on the metal is six.

In a further preferred embodiment of the invention, the metal M in the compound of the general formula I is hexacoordinated and contains two bidentate ligands L. In this embodiment, the compound of the general formula I can thus in each case contain two monodentate ligands L' and L" or one bidentate ligand L' or L". L' or L" here is preferably a cyclometallated ligand or a ligand which bonds via two oxygen atoms, in particular a ketoketonate derivative, preferably acetylacetonate, or a ligand which bonds via oxygen and nitrogen, preferably piccolinate.

In a further preferred embodiment of the invention, the metal M in the compound of the general formula I is coordinated in a square-planar or tetrahedral manner and preferably contains a bidentate ligand L. In this embodiment, the compound of the general formula I can thus in each case contain a monodentate ligand L' or L" or a bidentate ligand L', preferably a bidentate ligand. The ligand L' or L" is preferably a cyclometallated ligand or a ligand which bonds via two oxygen atoms, in particular a ketoketonate derivative, preferably acetylacetonate, or a ligand which bonds via oxygen and nitrogen, preferably piccolinate. The combinations of a monodentate ligand L and a tridentate ligand L' or a tridentate ligand L and a monodentate ligand L' are also furthermore possible.

Preferred neutral, monodentate ligands L' and L" are in each case selected, independently of one another on each occurrence, from carbon monoxide, NO, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, amines, such as, for example, trimethylamine, triethylamine, morpholine, phosphines, such as, for example, trifluorophosphine, trimethylphosphine, tricyclohexylphosphine, tri-tert-butylphosphine, triphenylphosphine, tris(pentafluorophenyl) phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butyl-arsine, triphenylstibine, tris(pentafluorophenyl)stibine, and nitrogen-containing heterocycles, such as, for example, pyridine, pyridazine, pyrazine, pyrimidine, triazine.

Preferred monoanionic, monodentate ligands L' and L" are in each case selected, independently of one another on each occurrence, from hydride, deuteride, the halides F, Cl, Br and I, alkylacetylides, such as, for example, methyl-$C\equiv C^-$, tert-butyl-$C\equiv C^-$, aryl- and heteroarylacetylides, such as, for example, phenyl-$C\equiv C^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. These groups and the aryl and heteroaryl groups are as defined above.

Preferred di- or trianionic, monodentate ligands L' and L" are $O^{2-}$, $S^{2-}$, nitrenes, which result in coordination in the form R—N=M, where R generally stands for a substituent, or $N^{3-}$.

Preferred neutral or mono- or dianionic, bidentate or polydentate ligands L' and L" are in each case selected, independently of one another on each occurrence, from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino) ethyl]-pyridine, 2-[1-(ethylimino)ethyl]pyridine, 2-[1-(isopropylimino)ethyl]pyridine, 2-[1-(tert-butylimino)ethyl] pyridine, diimines, such as, for example, 1,2-bis-(methylimino)ethane, 1,2-bis(ethylimino)ethane, 1,2-bis (isopropylimino)ethane, 1,2-bis(tert-butylimino)ethane, 2,3-bis(methylimino)butane, 2,3-bis-(ethylimino)butane, 2,3-bis (isopropylimino)butane, 2,3-bis(tert-butylimino)butane, 1,2-bis(phenylimino)ethane, 1,2-bis(2-methylphenylimino) ethane, 1,2-bis(2,6-diisopropylphenylimino)ethane, 1,2-bis (2,6-di-tert-butylphenylimino)ethane, 2,3-bis(phenylimino) butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino) ethane, bis(diphenylphosphino)propane, bis(dimethylphosphino)methane, bis(dimethylphosphino)ethane, bis (dimethylphosphino)propane, bis(diethylphosphino) methane, bis(diethylphosphino)ethane, bis (diethylphosphino)propane, bis(di-tert-butylphosphino) methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands L' and L" are borates of nitrogen-containing heterocycles, such as, for example, tetrakis(1-imidazolyl)borate and tetrakis(1-pyrazolyl) borate.

Preference is furthermore given to bidentate monoanionic ligands L' and L" which, with the metal, form a cyclometallated five-membered ring having at least one metal-carbon bond. These are, in particular, ligands as are generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals $R^1$. A multiplicity of such ligands is known to the person skilled in the art in the area of phosphorescent electroluminescent devices, and he will be able, without an inventive step, to select further ligands of this type as ligand L' and L", for compounds of the formula I. Generally suitable for this purpose is, in particular, the combination of two groups, as depicted above by the formulae (1) to (24), where one group preferably bonds via a neutral nitrogen atom or a carbene atom and the other group preferably bonds via a negatively charged carbon atom or a negatively charged nitrogen atom. The ligand L' or L" can then be formed from the groups of the formulae (1) to (24) by these groups bonding to one another, in each case at the position denoted by a dashed bond, and to the metal at the positions denoted by *.

Likewise preferred ligands L' or L" are $\eta^5$-cyclopentadienyl, $\eta^5$-pentamethylcyclopentadienyl, $\eta^6$-benzene or $\eta^7$-cycloheptatrienyl, each of which may be substituted by one or more radicals $R^1$.

Likewise preferred ligands L' or L" are 1,3,5-cis-cyclohexane derivatives, in particular of the formula (44), 1,1,1-tri (methylene)methane derivatives, in particular of the formula (45), and 1,1,1-trisubstituted methanes, in particular of the formula (46):

formula (44)

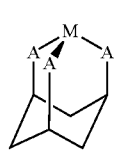

-continued

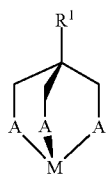

formula (45)

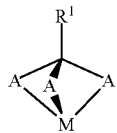

formula (46)

where, in the formulae, the coordination to the metal M is shown in each case, $R^1$ has the meaning indicated above, and A denotes, identically or differently on each occurrence, $O^-$, $S^-$, $COO^-$, $P(R^1)_2$ or $N(R^1)_2$.

The complexes of the formula I can in principle be prepared by various processes, but where the processes described below have proven particularly suitable. The complexes of the formula I are obtained by reaction of the ligand of the formula V, VI or VII and optionally further ligands L', L" with metal alkoxides of the formula (47), with metal ketoketonates of the formula (48) or metal halides of the formula (49):

$M(OR^2)_r$   formula (47)

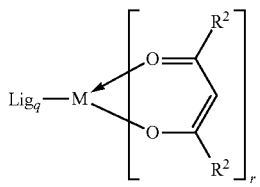

formula (48)

$MHal_r$   formula (49)

where M and $R^2$ have the same meaning as described above, and the following applies to the other symbols and indices:
  Hal is on each occurrence, identically or differently, F, Cl, Br or I;
  Lig is on each occurrence, identically or differently, a neutral or monoanionic, monodentate or bidentate ligand, for example a halide, hydroxide or ethylene glycolate;
  q is on each occurrence, identically or differently, 0, 1, 2, 3 or 4, preferably 0, 1 or 2;
  r is on each occurrence, identically or differently, 1, 2, 3, 4, 5 or 6;
the compounds of the formulae (48) and (49) here may also be charged and also contain one or more counterions; furthermore, the compounds of the formulae (47) to (49), in particular of the formula (49), may also be in the form of the hydrate.

A complex-analogous synthesis of the ligands is likewise possible by reacting precursors of the ligand with metal compounds of the formula (47), (48) or (49) and reacting the precursors of the ligand further on the metal complexes formed in this way to give the finished ligand. This may be advantageous, in particular, for systems containing tetradentate or hexadentate ligands in that the bridging unit Z is introduced on the complex.

The synthesis can be activated, for example, thermally, photochemically and/or by microwave radiation.

These processes enable the complexes to be obtained easily in high purity, preferably in a purity of >99% according to $^1$H-NMR or HPLC analysis, particularly preferably >99.9%.

Examples of preferred structures are structures (1) to (362) shown in the following table.

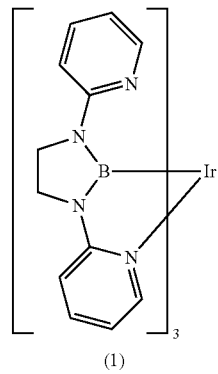

(1)

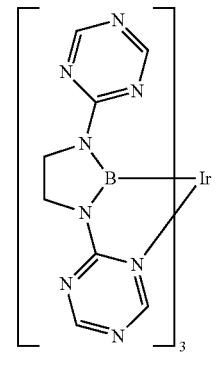

(2)

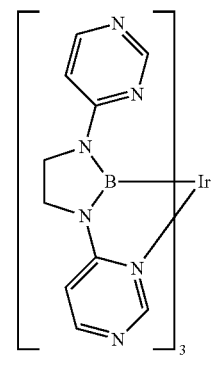

(3)

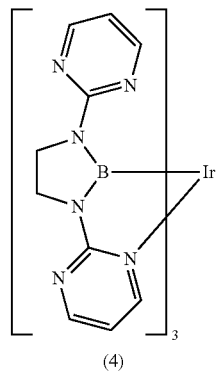
(4)
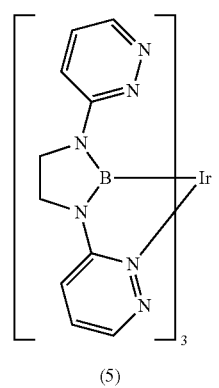
(5)
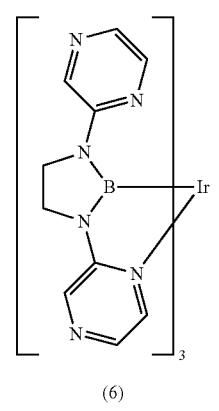
(6)
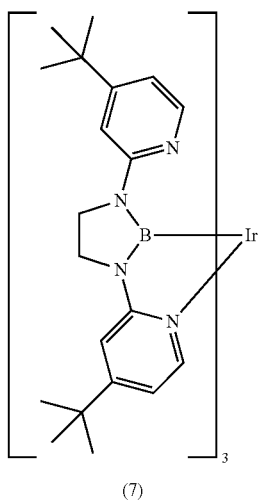
(7)
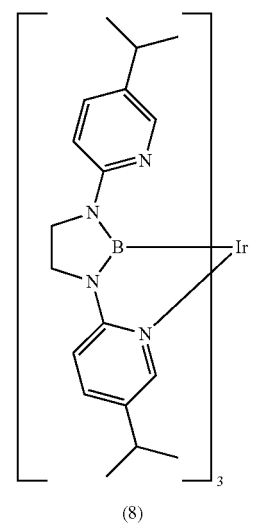
(8)
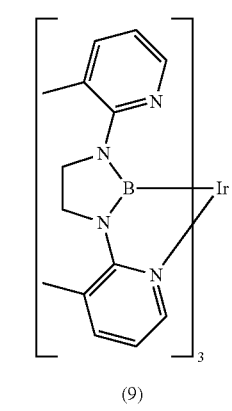
(9)

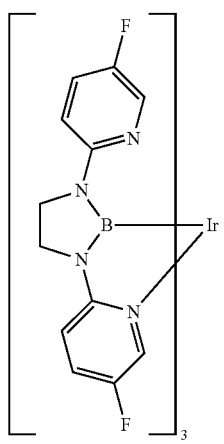
(10)
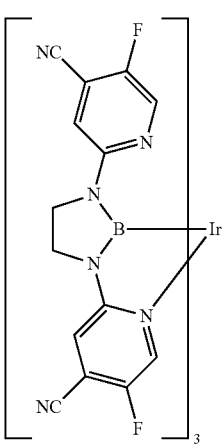
(11)
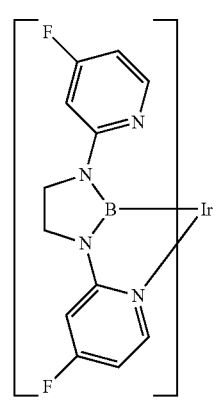
(12)
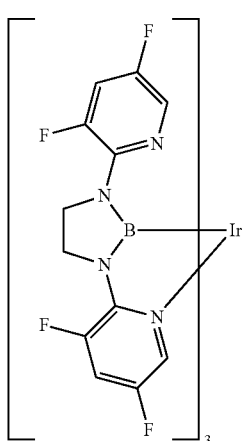
(13)
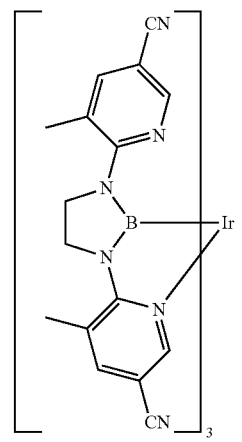
(14)
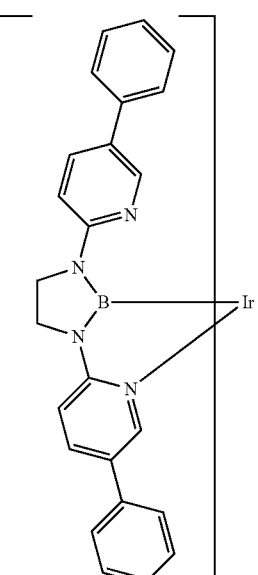
(15)

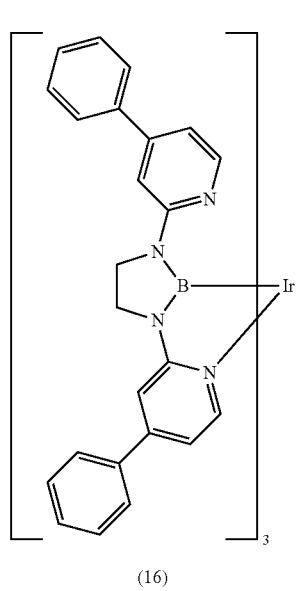
(16)
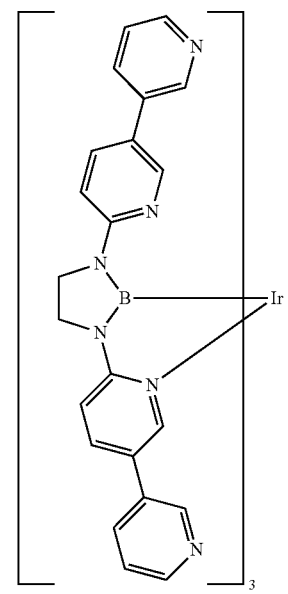
(18)
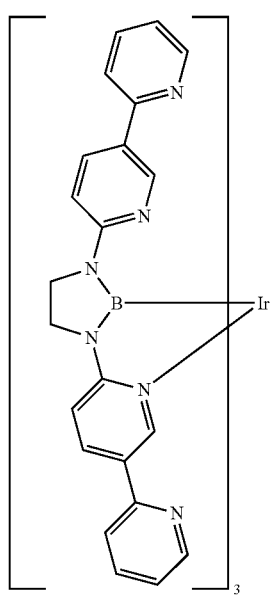
(17)
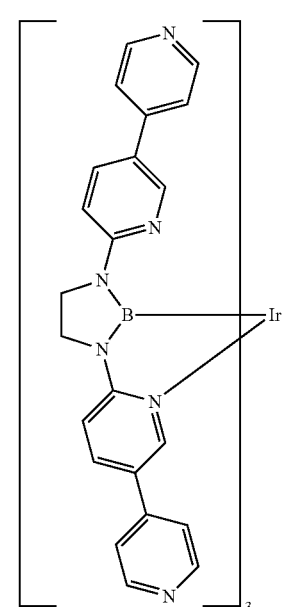
(19)

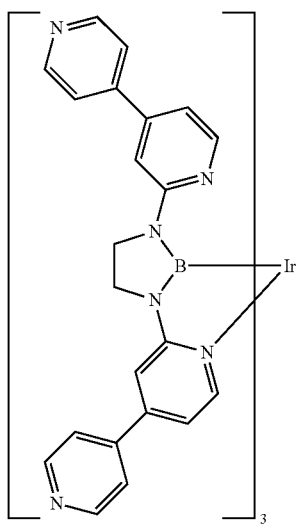
(20)
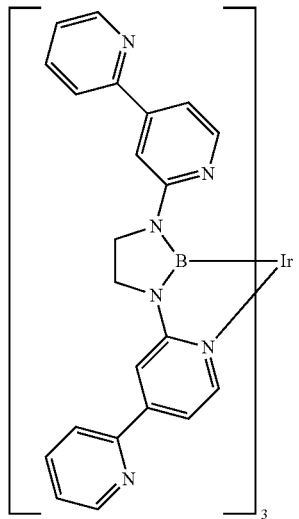
(22)
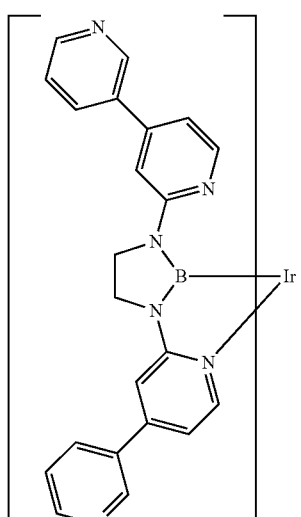
(21)
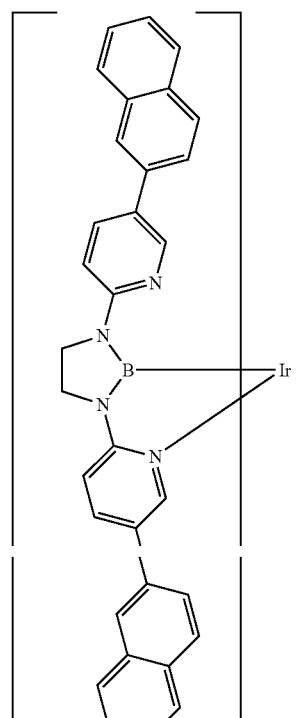
(23)

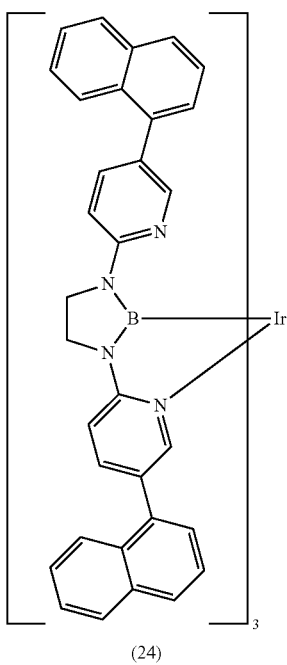
(24)
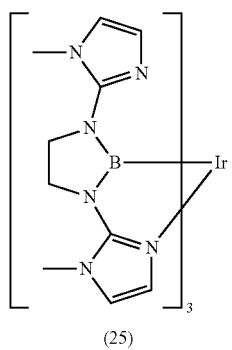
(25)
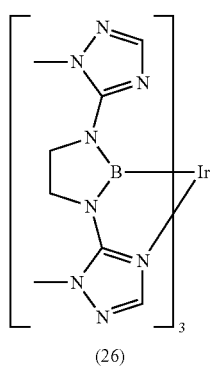
(26)
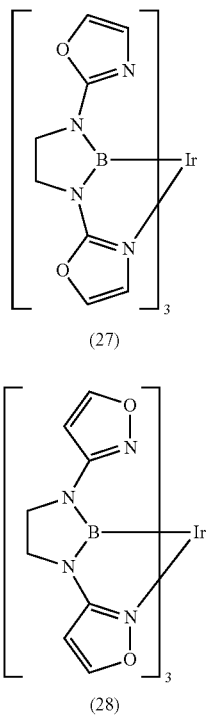
(27)
(28)
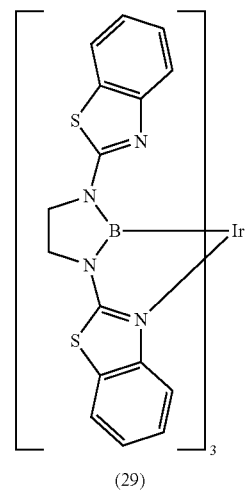
(29)
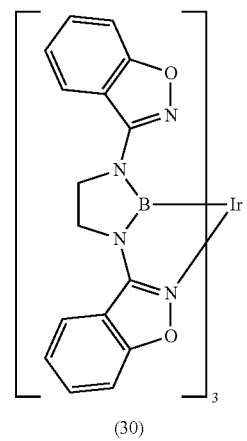
(30)

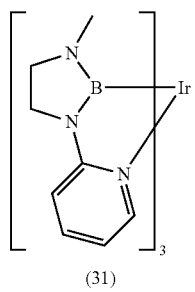
(31)
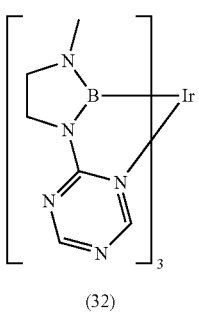
(32)
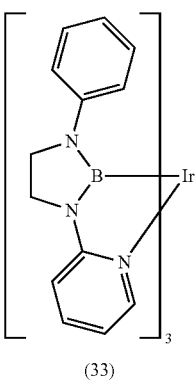
(33)
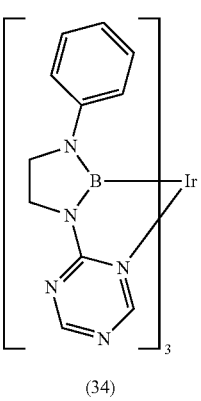
(34)
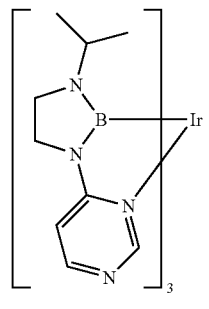
(35)
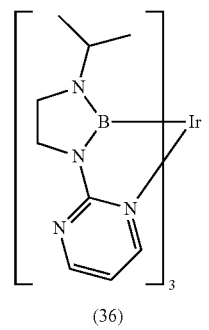
(36)
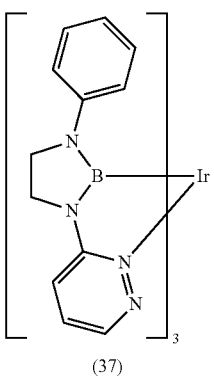
(37)
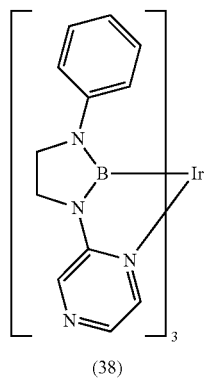
(38)

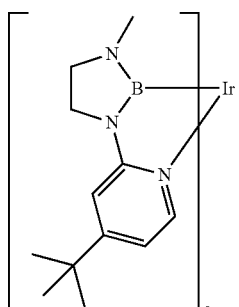
(39)
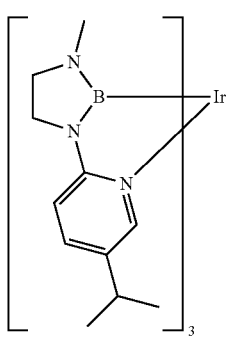
(40)
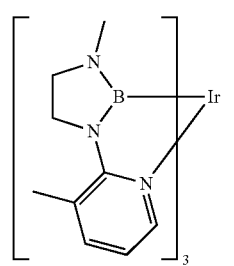
(41)
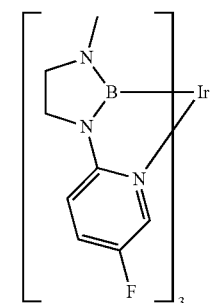
(42)
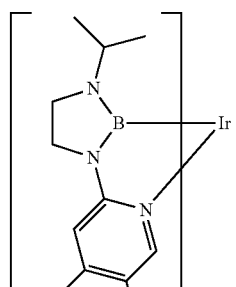
(43)
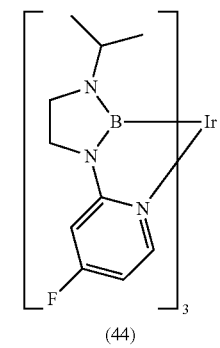
(44)
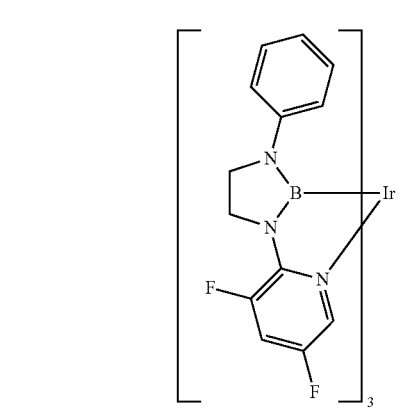
(45)
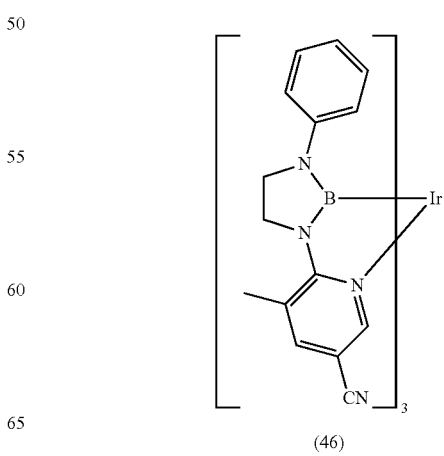
(46)

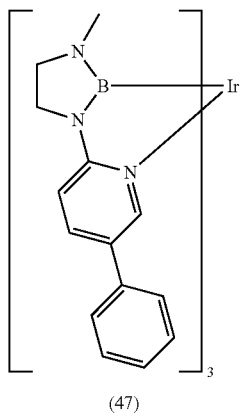
(47)
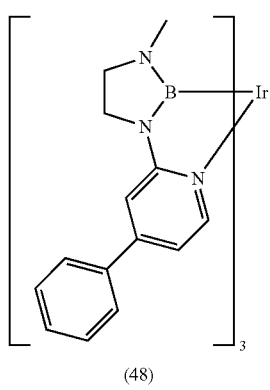
(48)
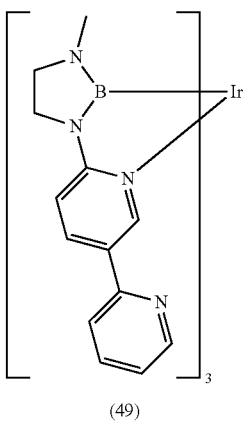
(49)
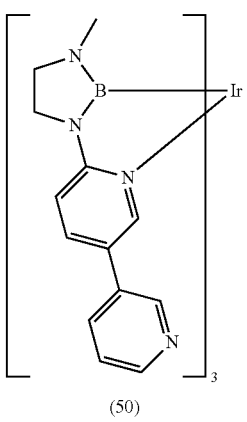
(50)
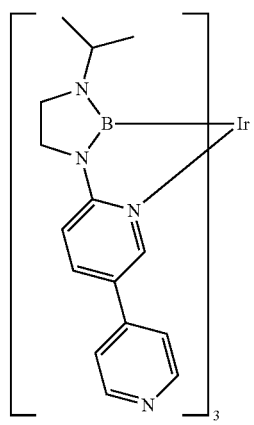
(51)
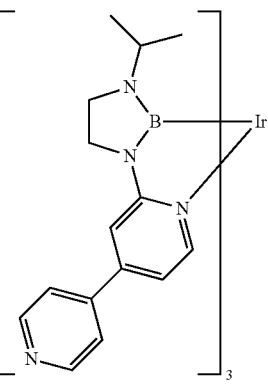
(52)
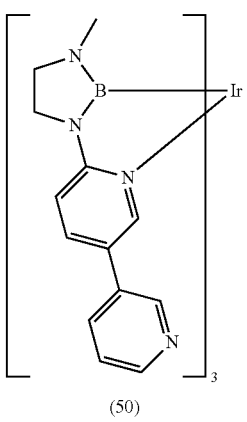
(53)

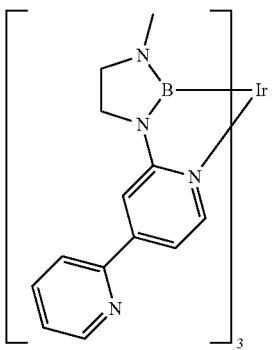
(54)
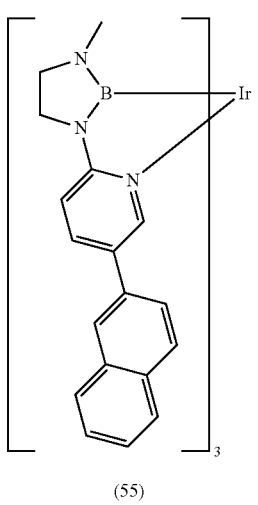
(55)
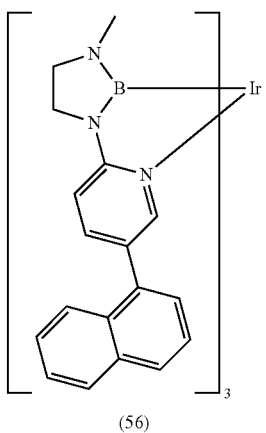
(56)
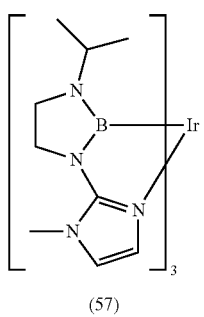
(57)
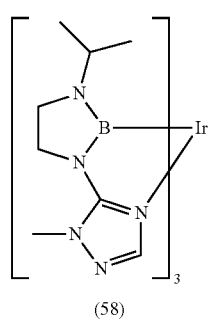
(58)
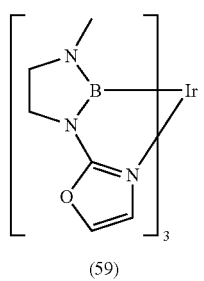
(59)
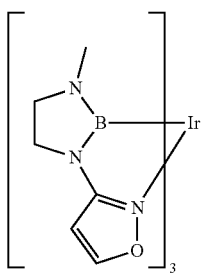
(60)
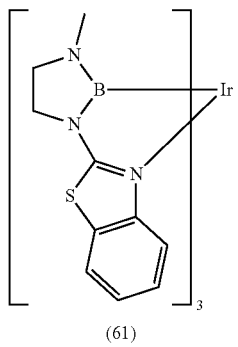
(61)
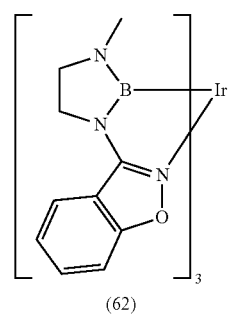
(62)

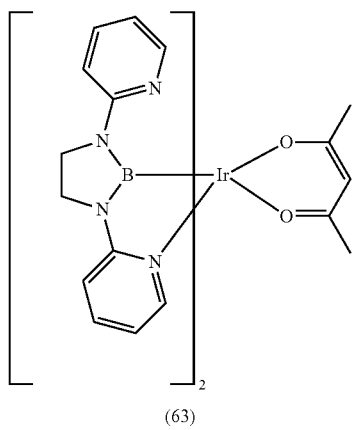
(63)
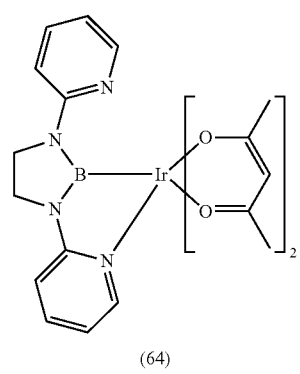
(64)
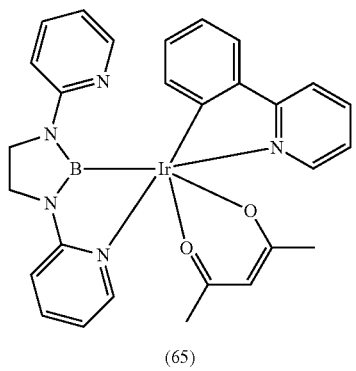
(65)
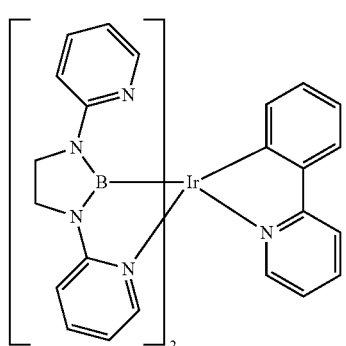
(66)
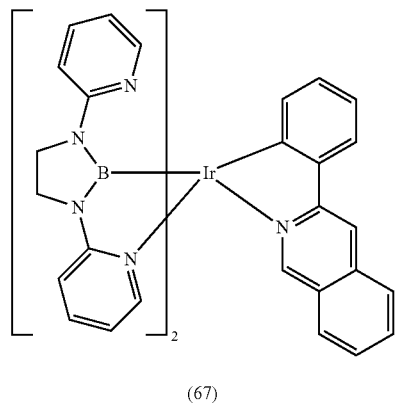
(67)
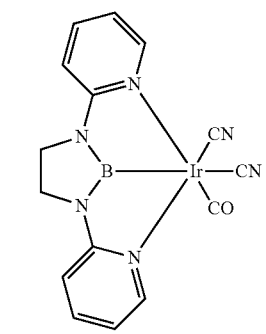
(68)
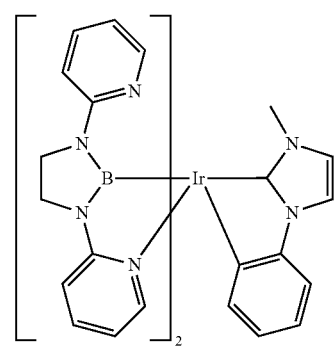
(69)
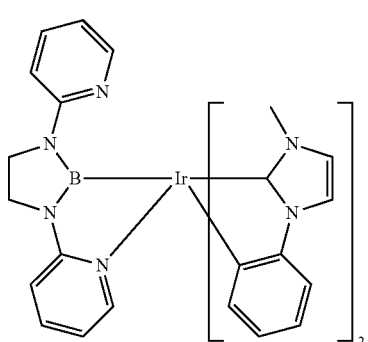
(70)

-continued
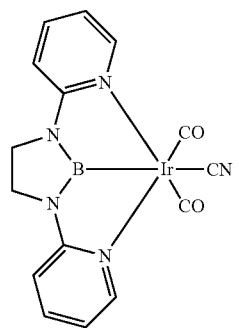
(71)
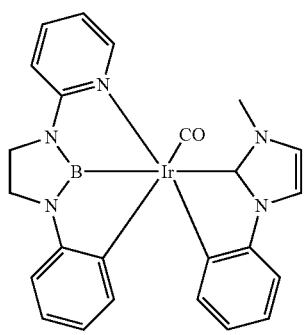
(72)
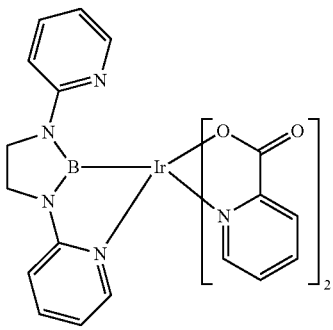
(73)
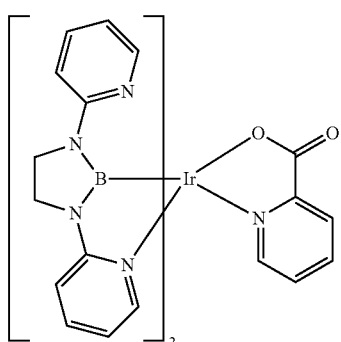
(74)
-continued
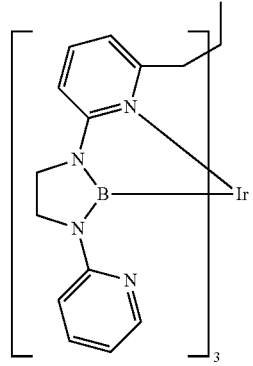
(75)
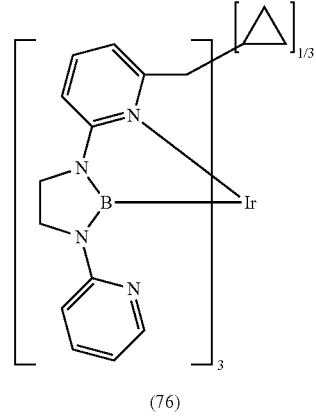
(76)
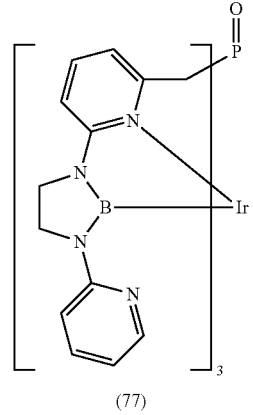
(77)
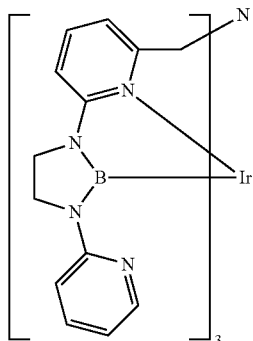
(78)

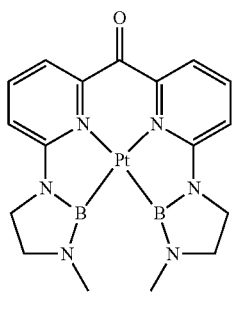
(79)
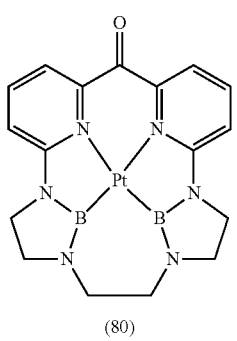
(80)
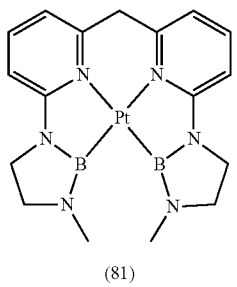
(81)
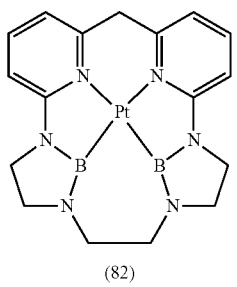
(82)
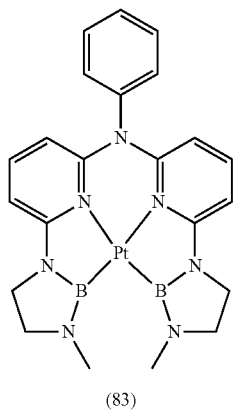
(83)
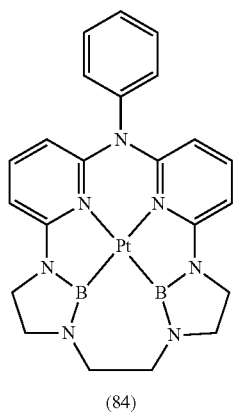
(84)
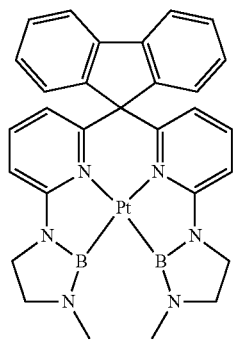
(85)
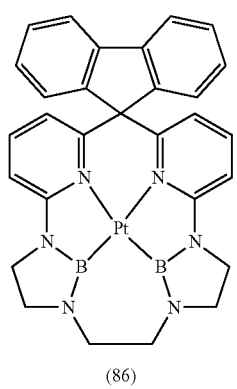
(86)

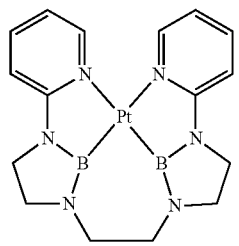
(87)
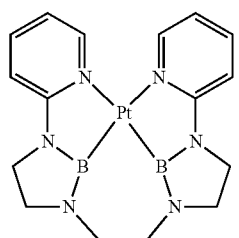
(88)
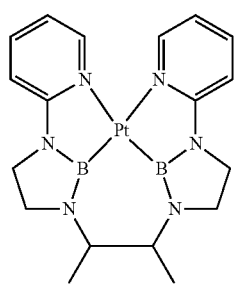
(89)
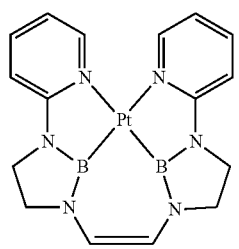
(90)
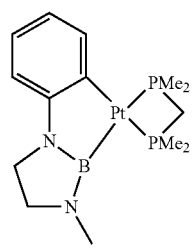
(91)
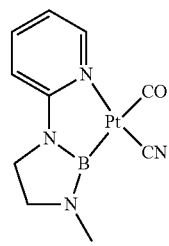
(92)
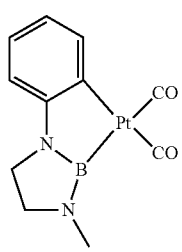
(93)
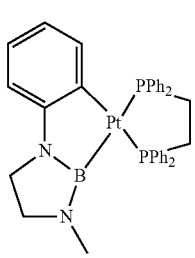
(94)
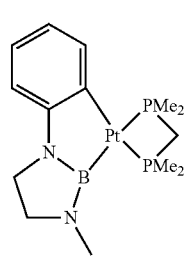
(95)
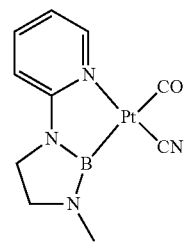
(96)

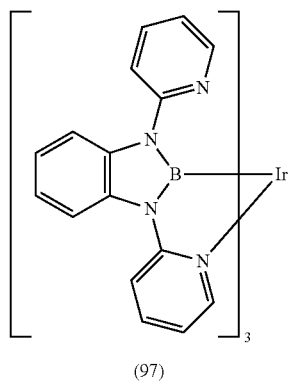
(97)
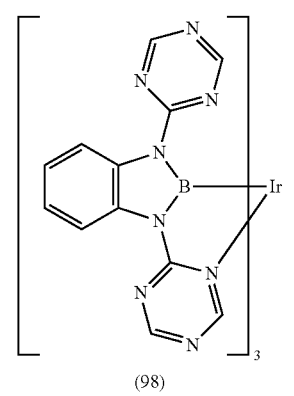
(98)
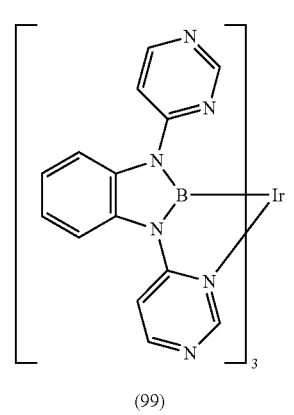
(99)
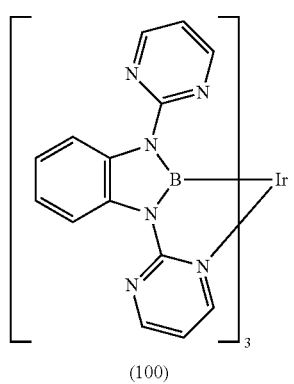
(100)
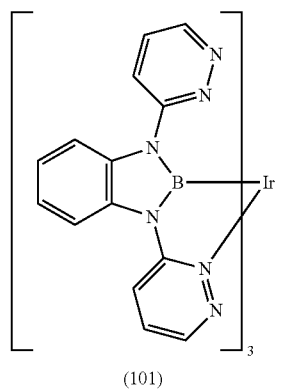
(101)
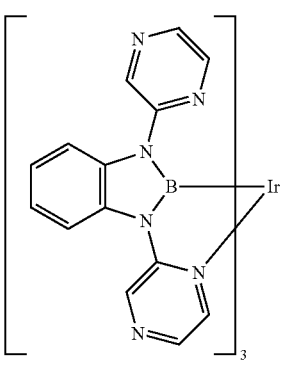
(102)
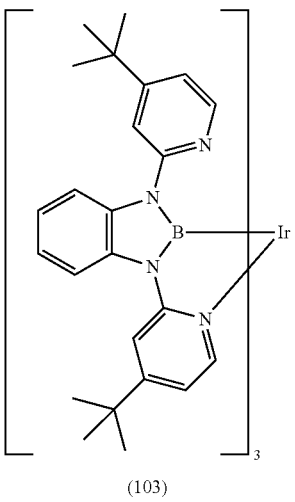
(103)

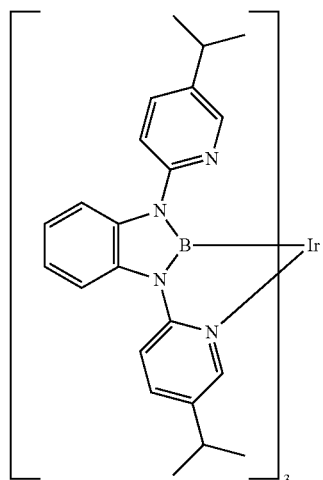
(104)
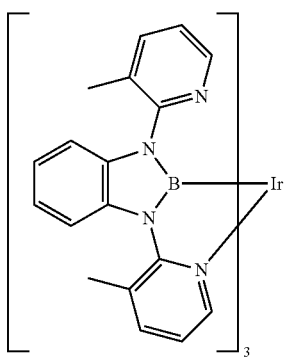
(105)
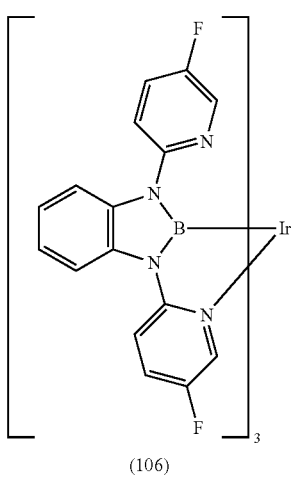
(106)
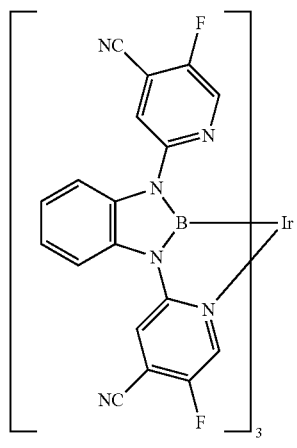
(107)
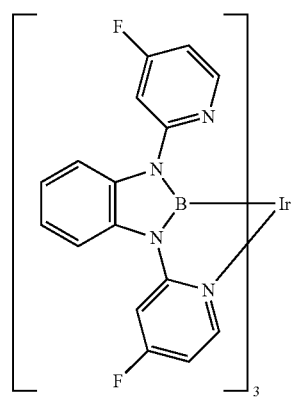
(108)
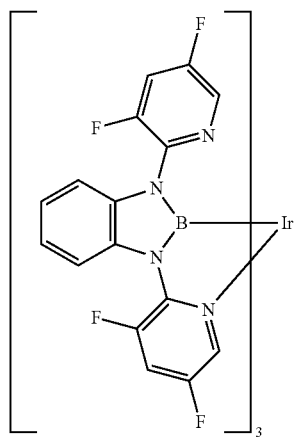
(109)

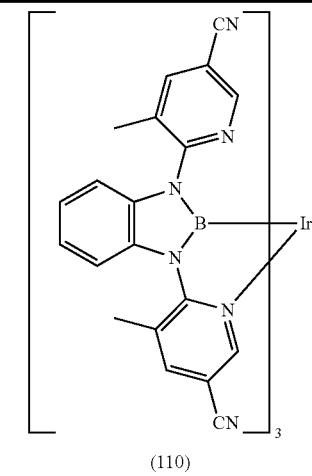
(110)
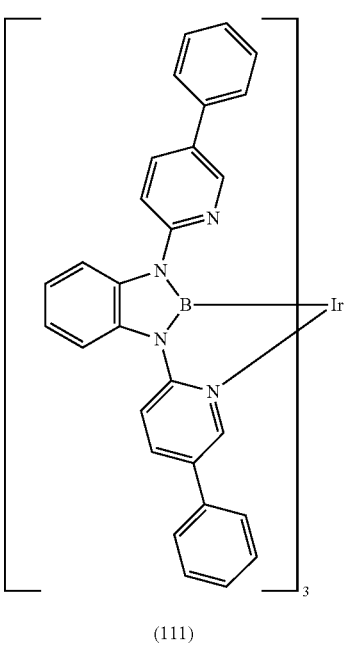
(111)
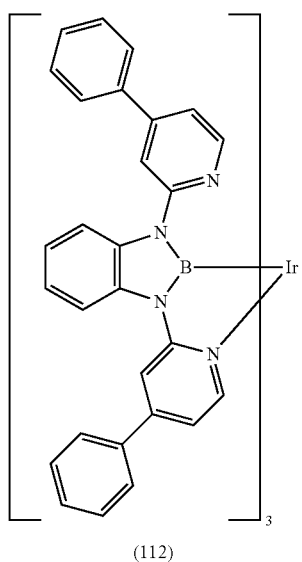
(112)
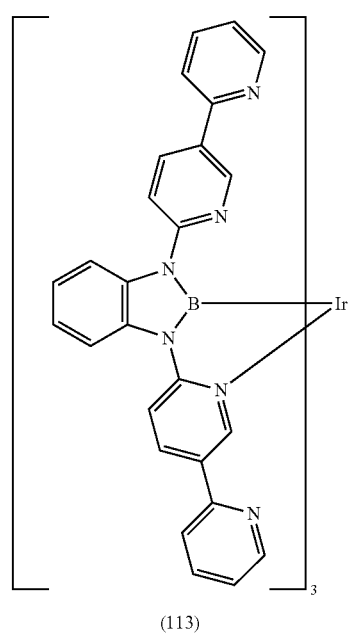
(113)
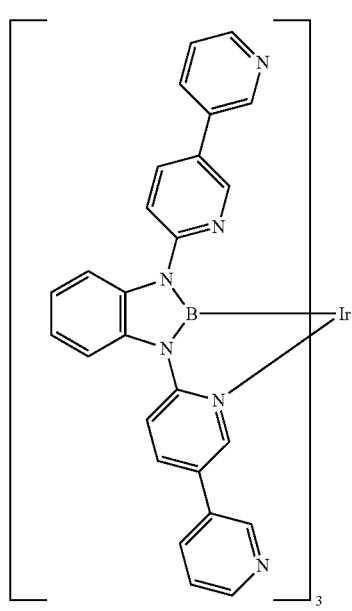
(114)

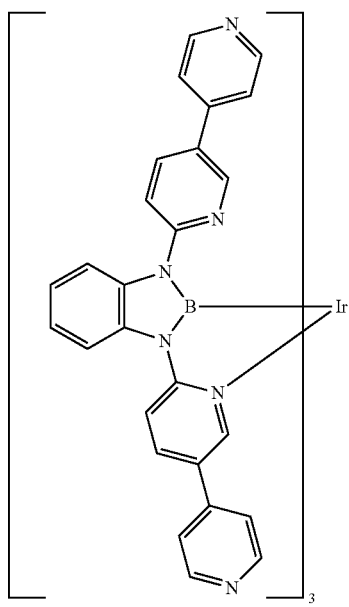
(115)
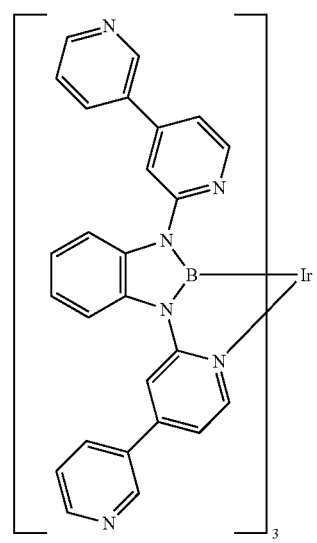
(117)
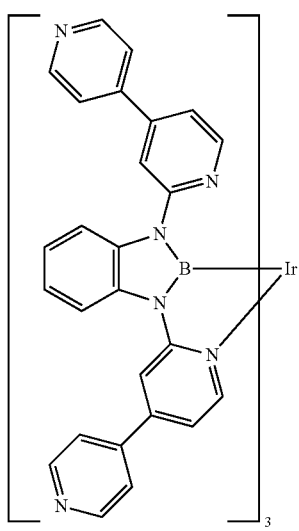
(116)
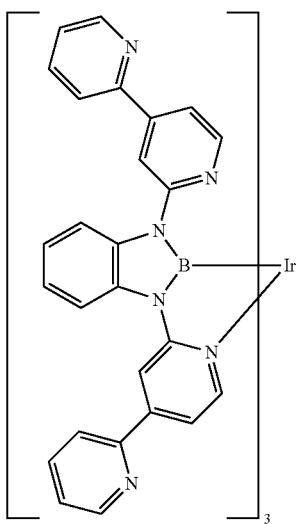
(118)

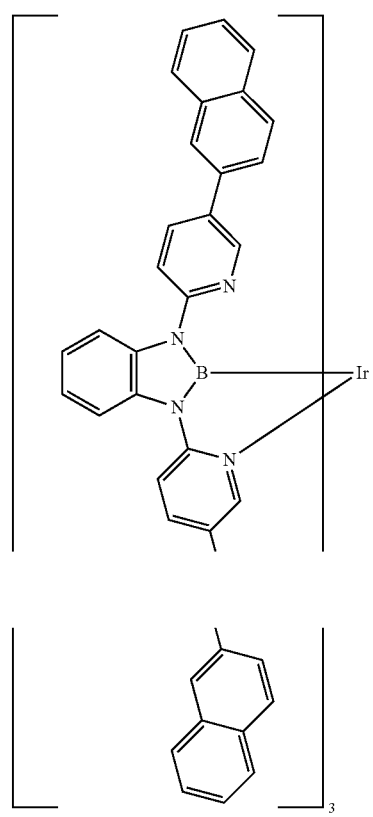
(119)
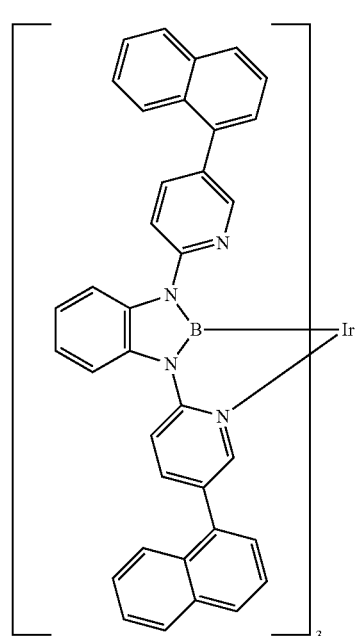
(120)
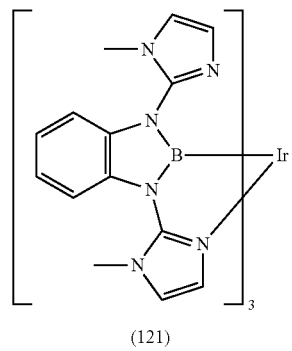
(121)
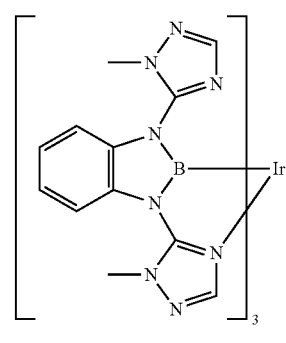
(122)
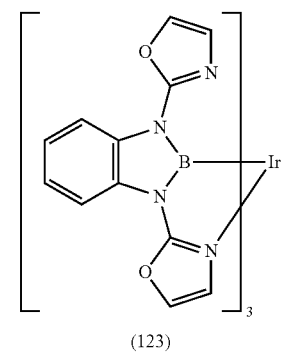
(123)
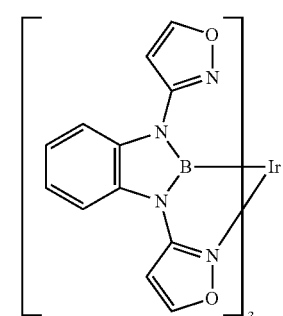
(124)

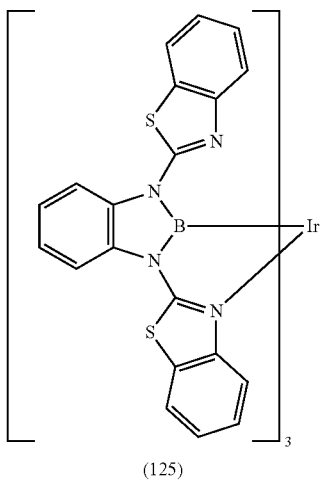
(125)
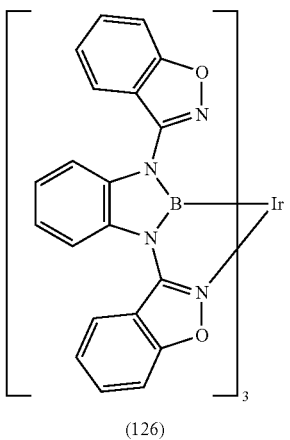
(126)
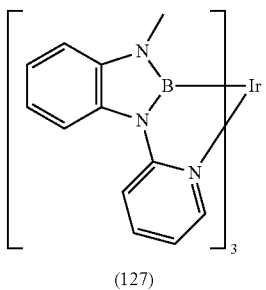
(127)
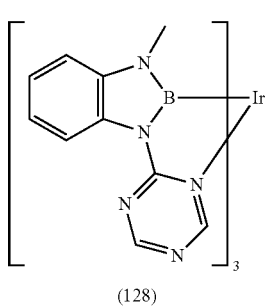
(128)
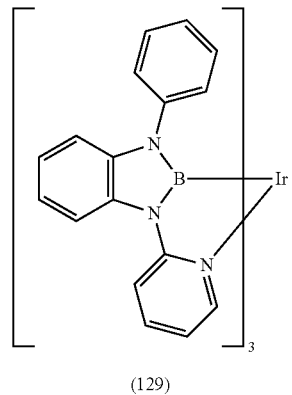
(129)
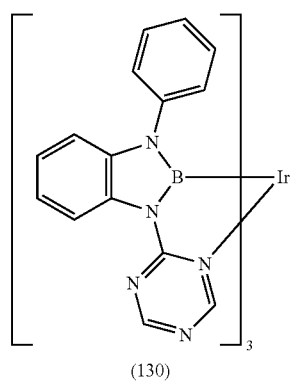
(130)
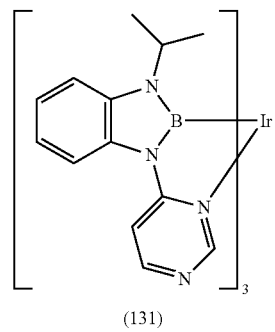
(131)
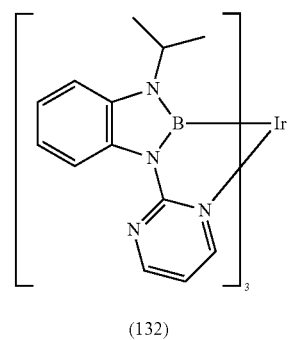
(132)

-continued
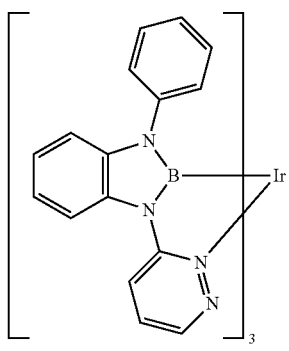
(133)
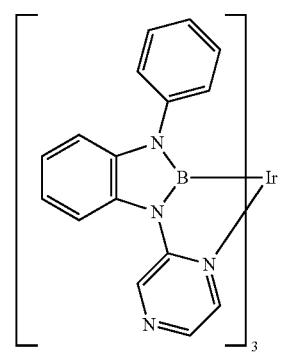
(134)
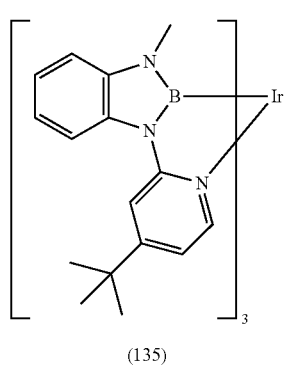
(135)
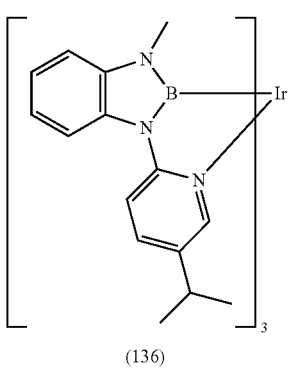
(136)
-continued
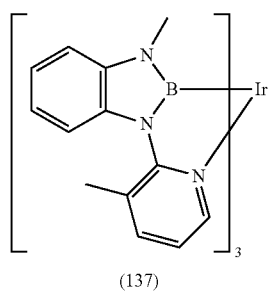
(137)
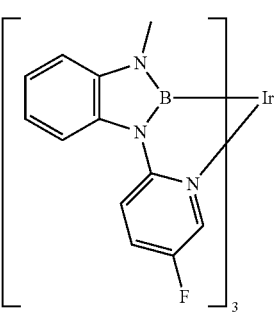
(138)
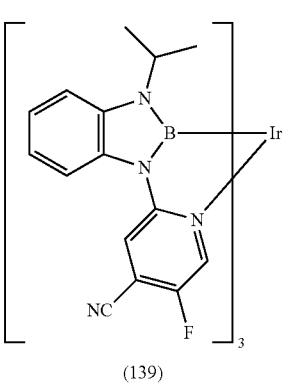
(139)
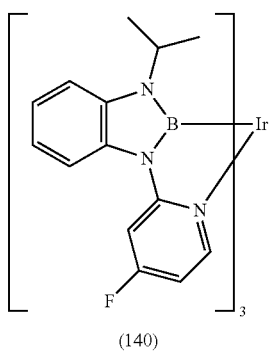
(140)

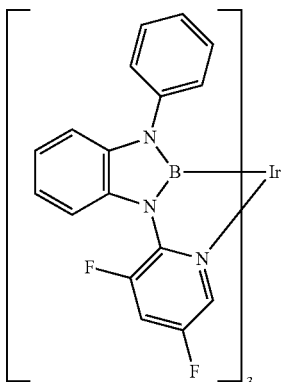
(141)
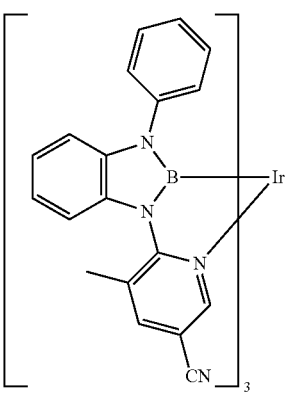
(142)
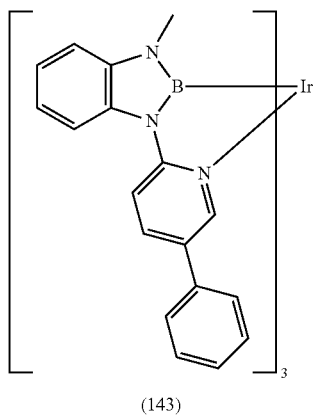
(143)
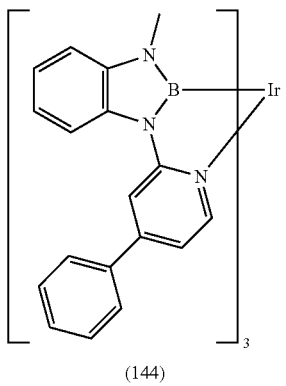
(144)
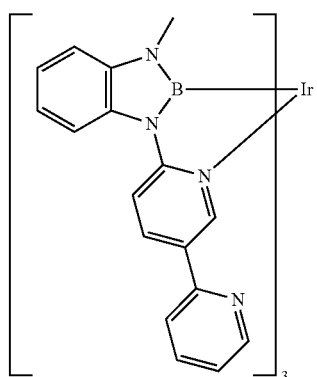
(145)
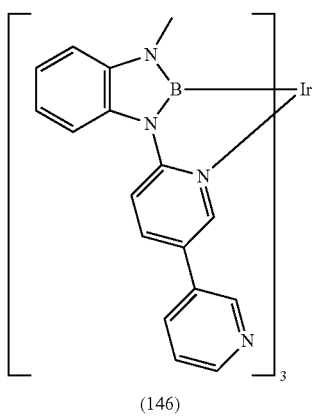
(146)
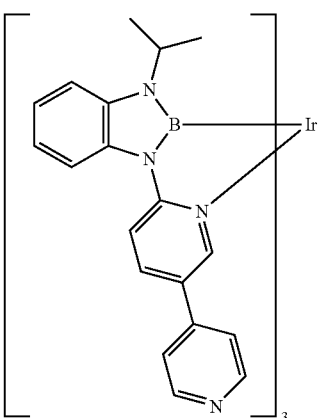
(147)

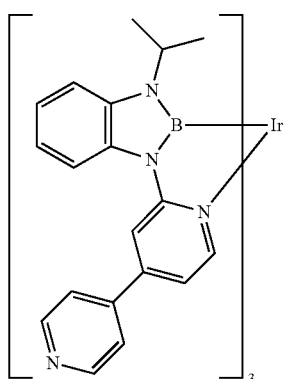
(148)
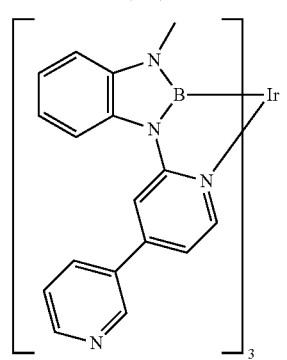
(149)
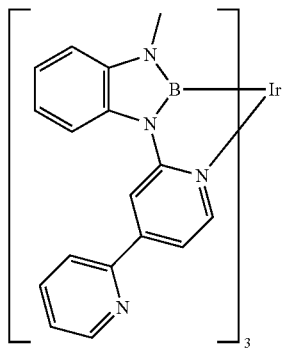
(150)
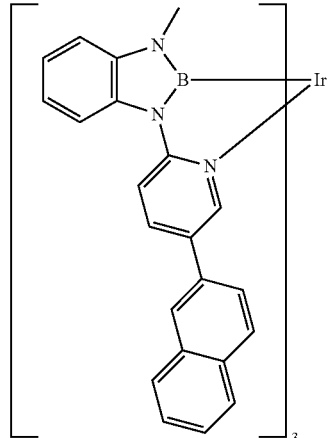
(151)
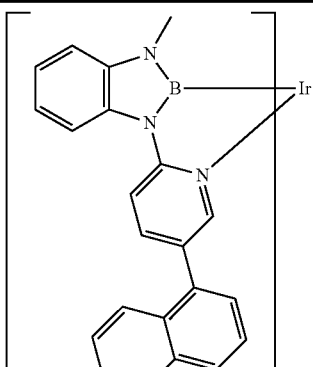
(152)
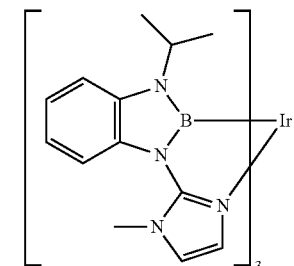
(153)
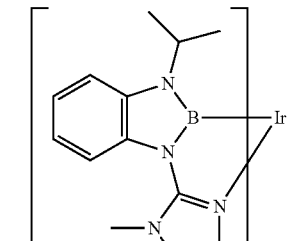
(154)
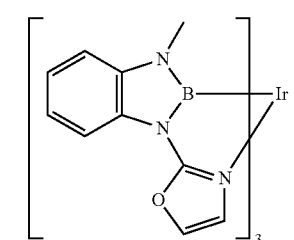
(155)

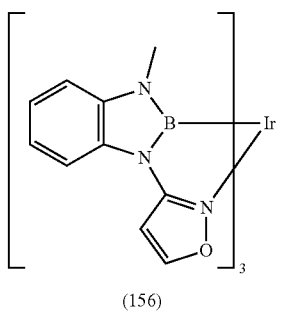
(156)
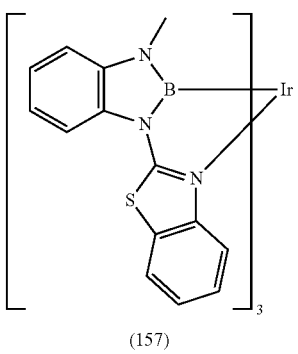
(157)
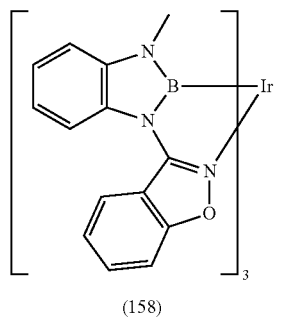
(158)
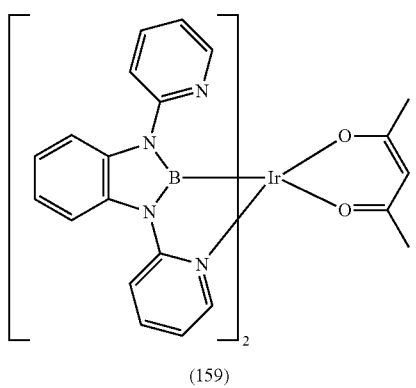
(159)
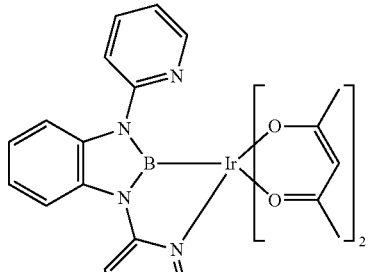
(160)
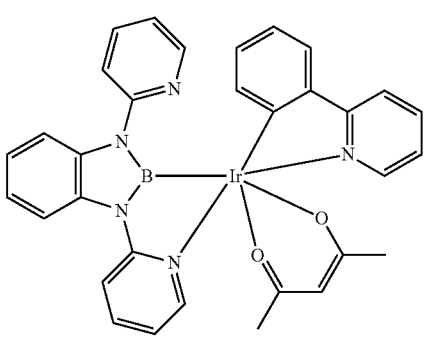
(161)
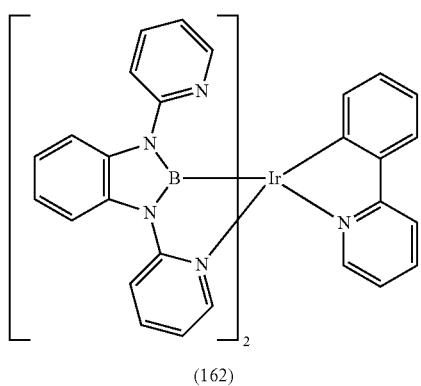
(162)
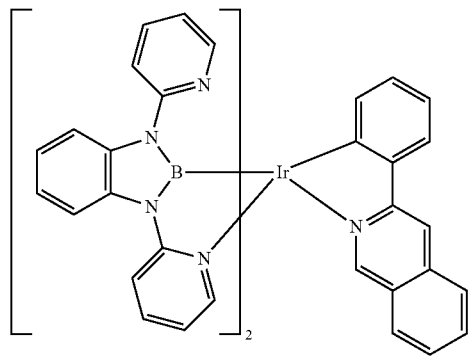
(163)

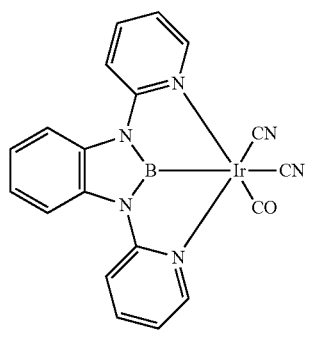
(164)
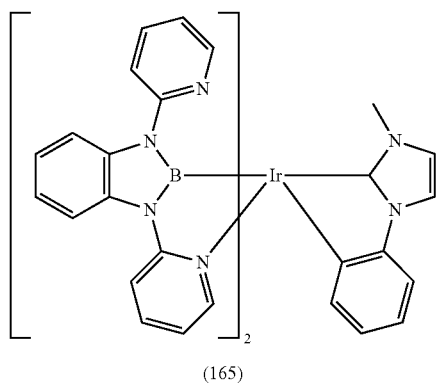
(165)
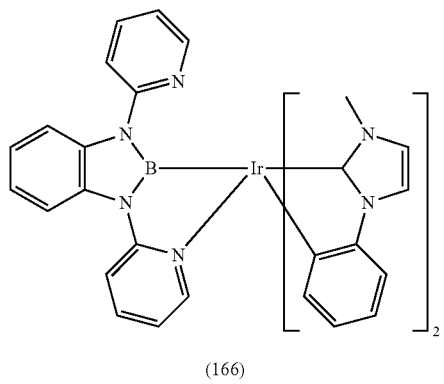
(166)
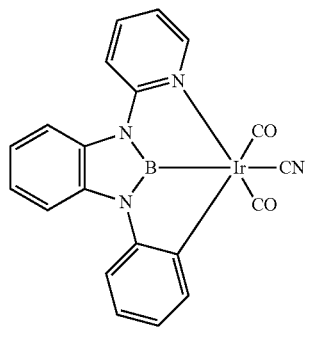
(167)
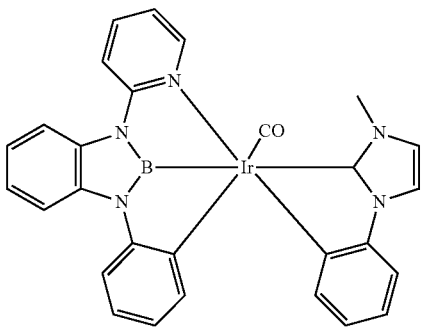
(168)
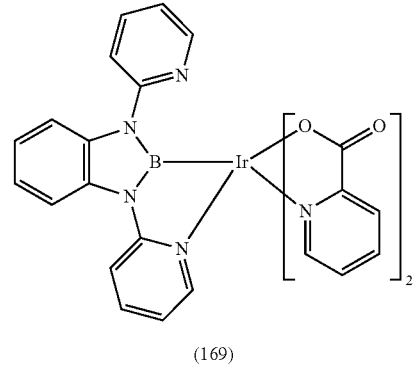
(169)
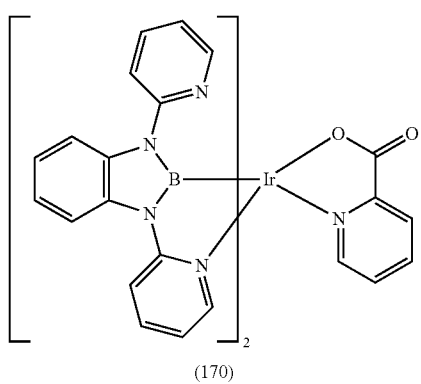
(170)
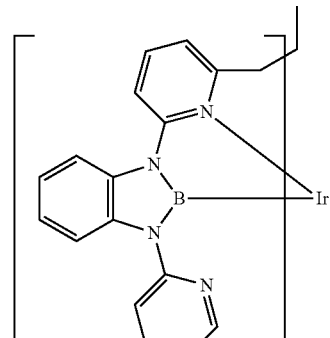
(171)

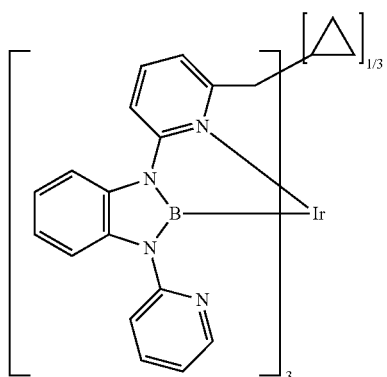
(172)
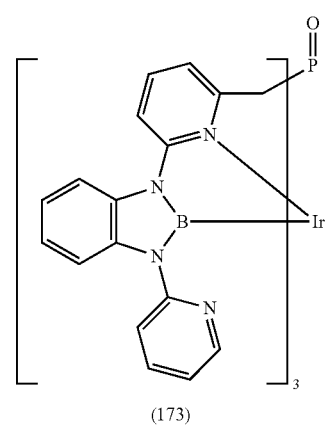
(173)
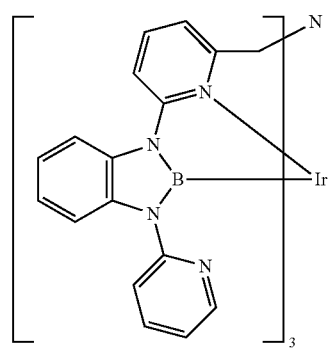
(174)
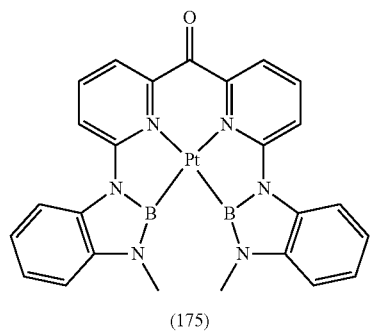
(175)
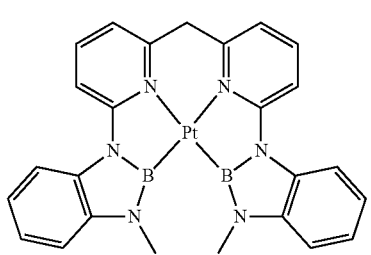
(176)
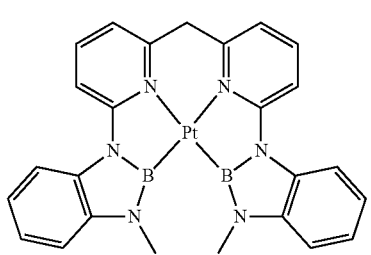
(177)
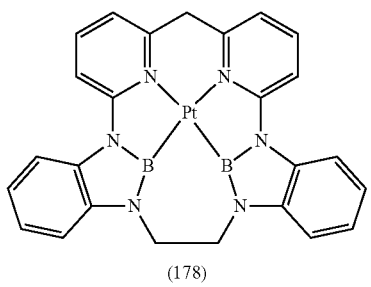
(178)
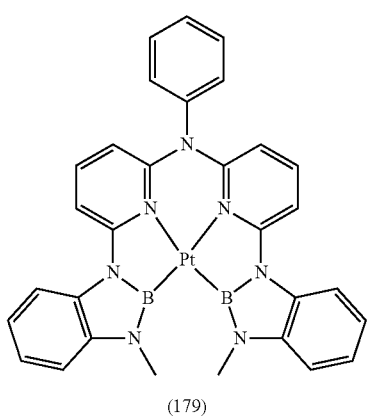
(179)

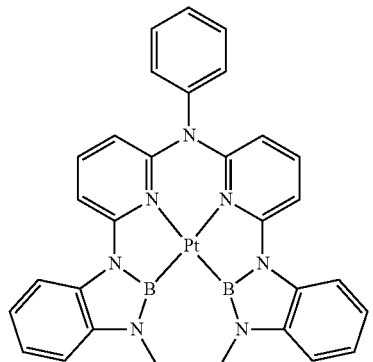
(180)
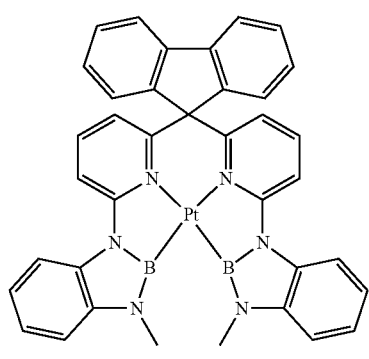
(181)
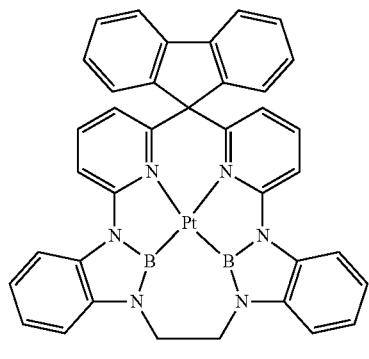
(182)
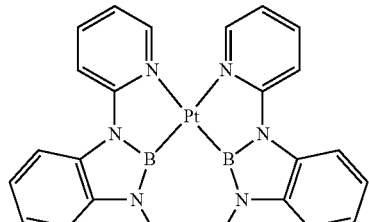
(183)
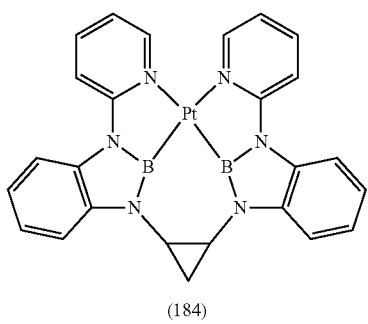
(184)
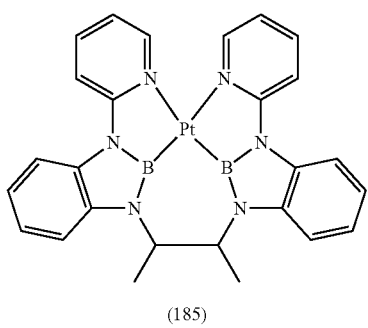
(185)
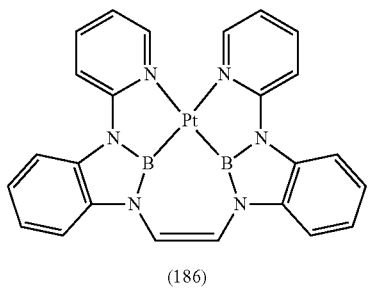
(186)
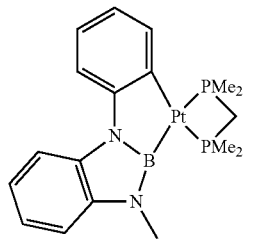
(187)
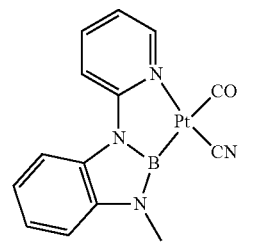
(188)

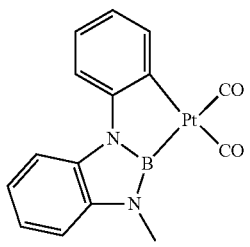
(189)
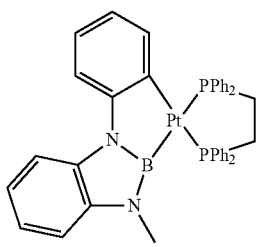
(190)
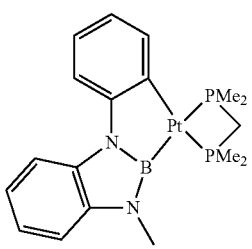
(191)
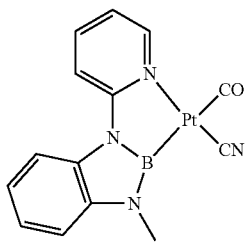
(192)
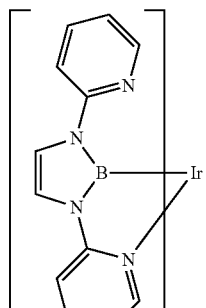
(193)
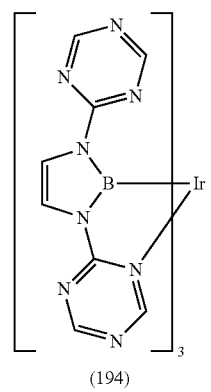
(194)
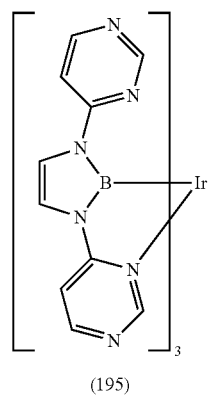
(195)
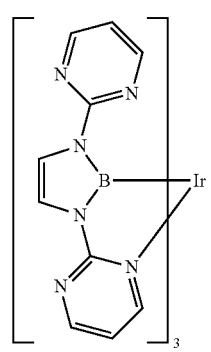
(196)
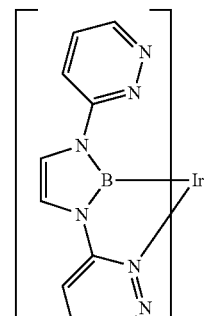
(197)

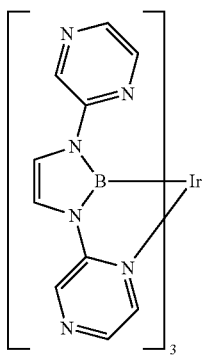
(198)
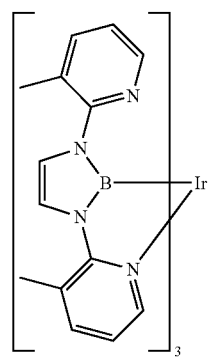
(201)
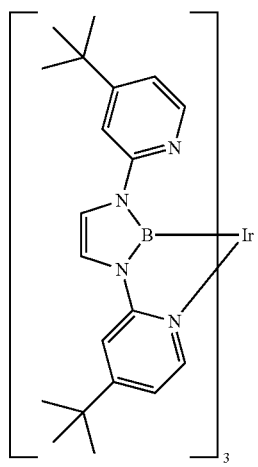
(199)
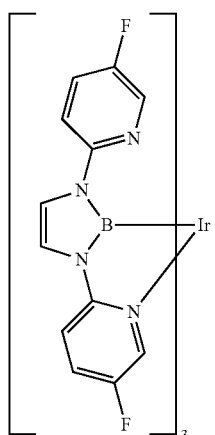
(202)
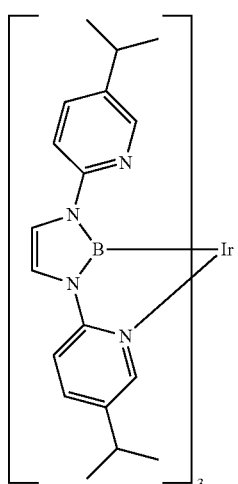
(200)
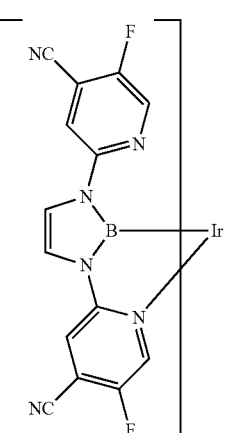
(203)

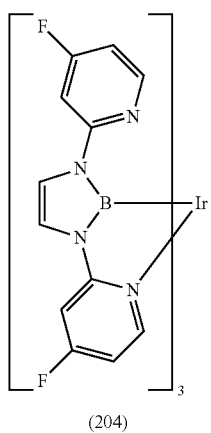
(204)
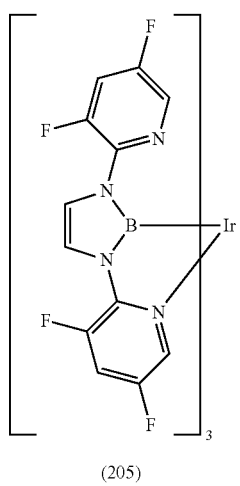
(205)
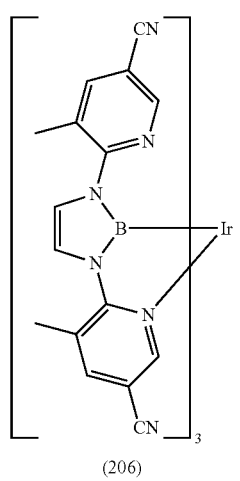
(206)
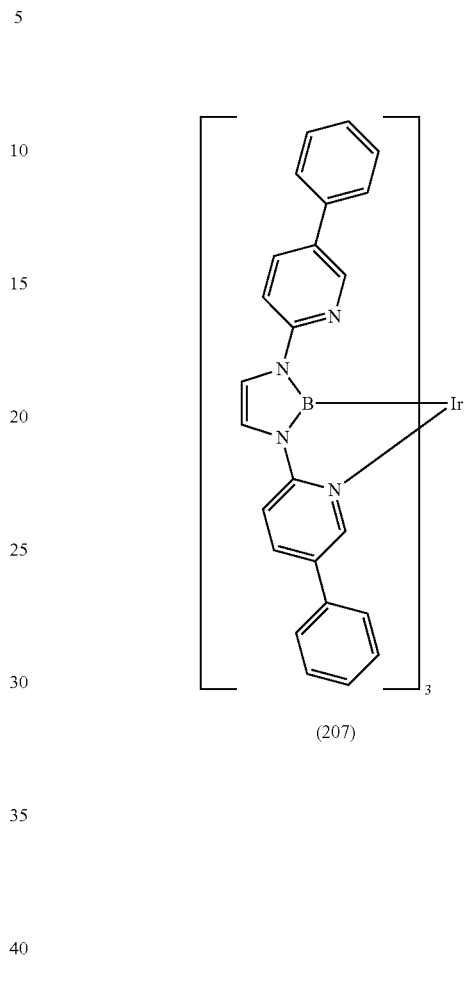
(207)
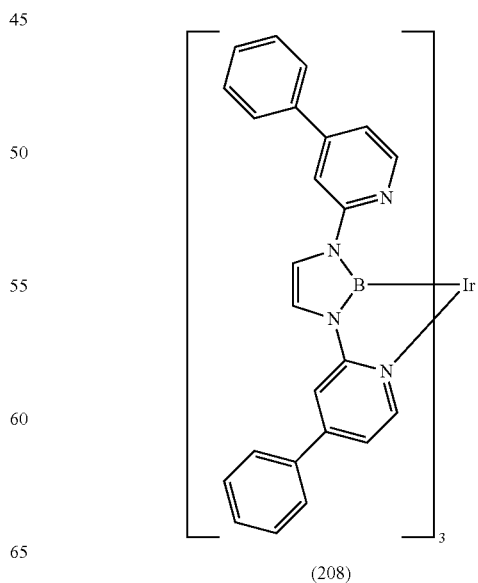
(208)

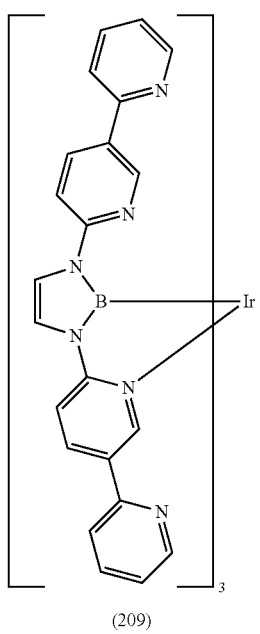
(209)
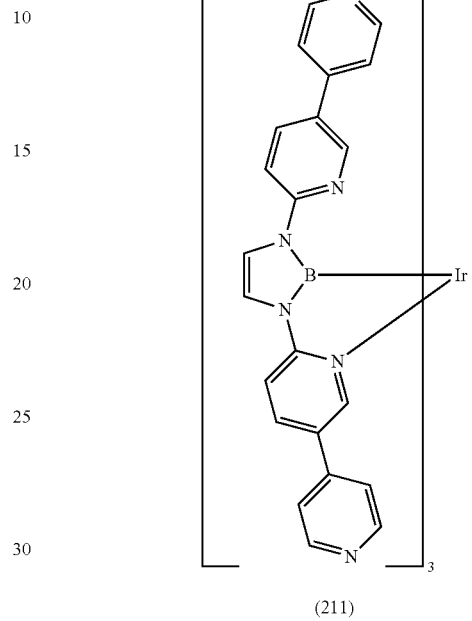
(211)
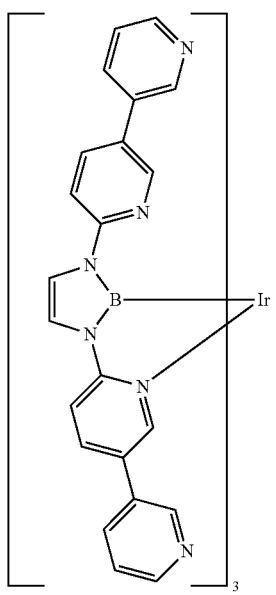
(210)
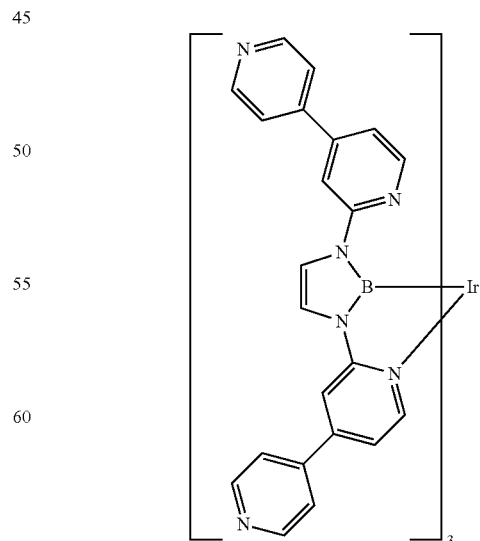
(212)

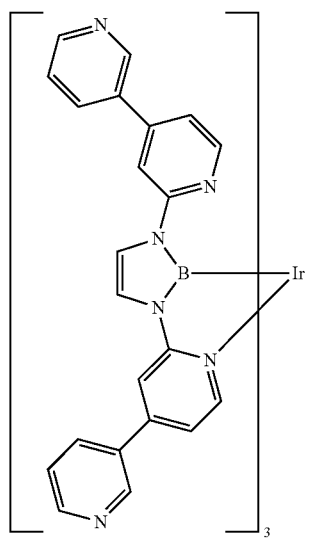
(213)
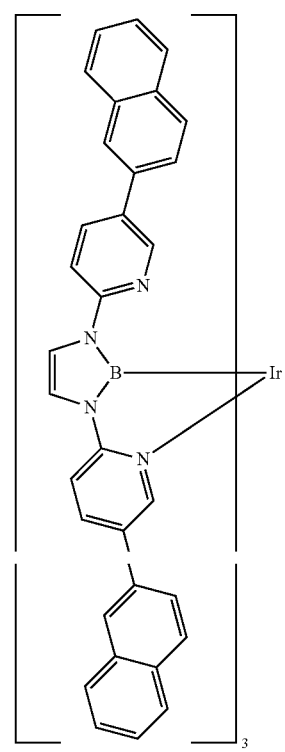
(215)
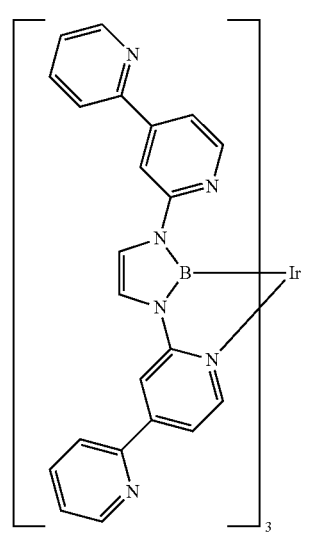
(214)
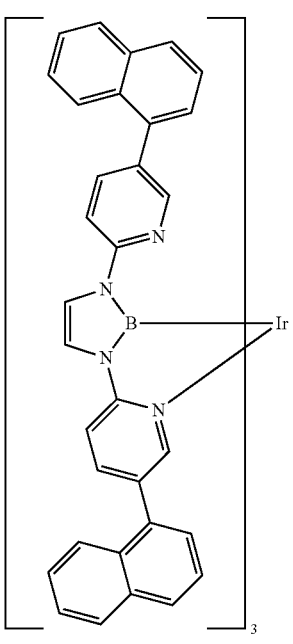
(216)

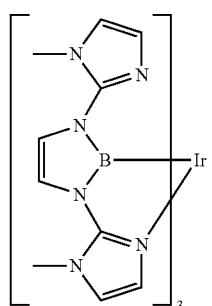
(217)
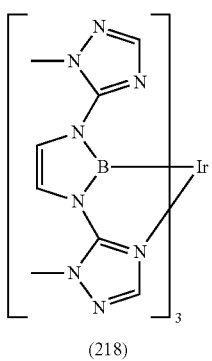
(218)
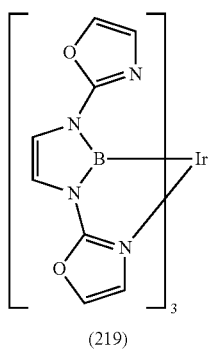
(219)
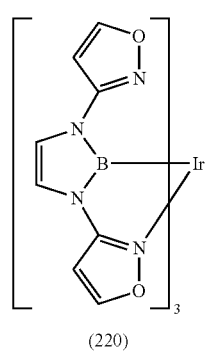
(220)
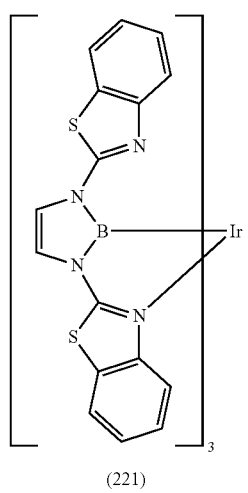
(221)
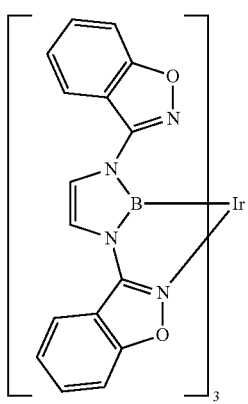
(222)
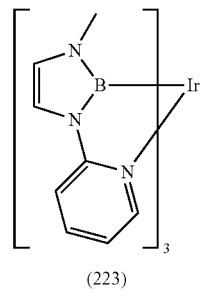
(223)
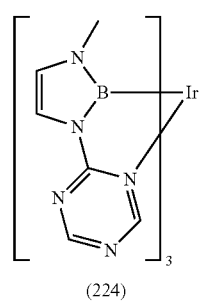
(224)

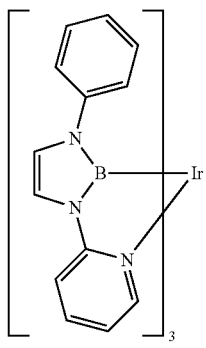
(225)
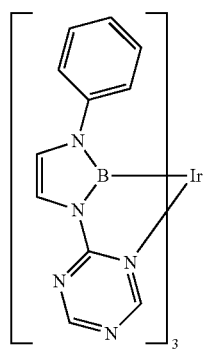
(226)
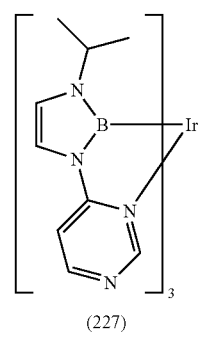
(227)
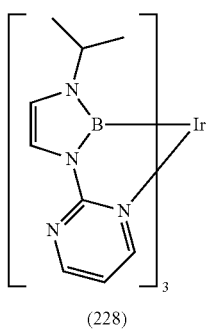
(228)
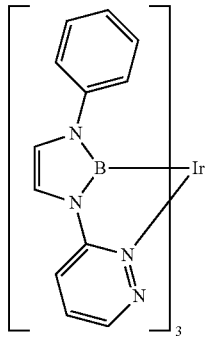
(229)
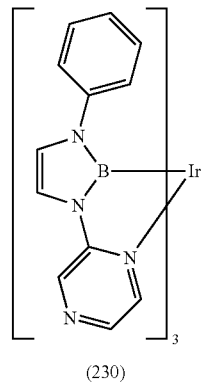
(230)
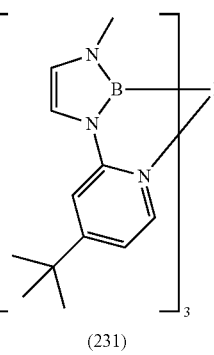
(231)
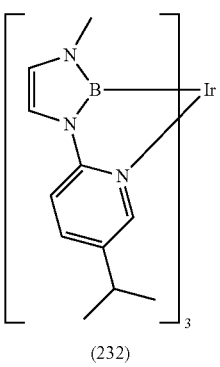
(232)

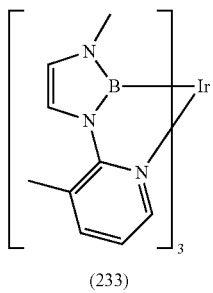
(233)
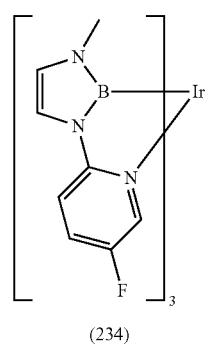
(234)
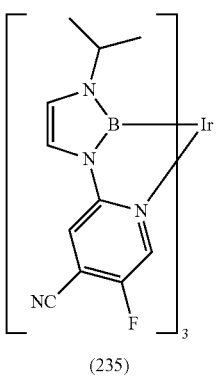
(235)
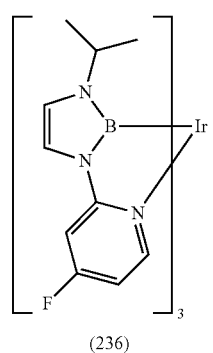
(236)
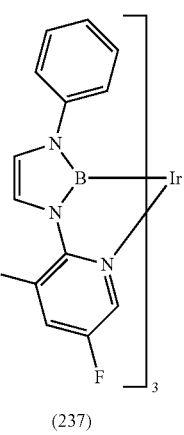
(237)
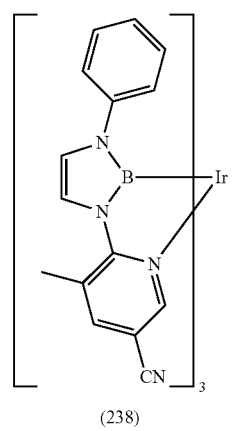
(238)
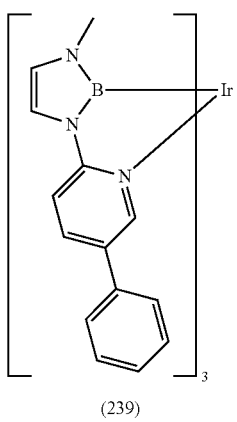
(239)

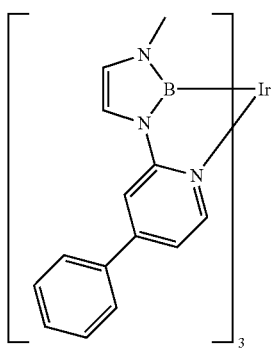
(240)
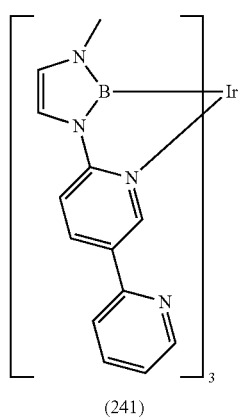
(241)
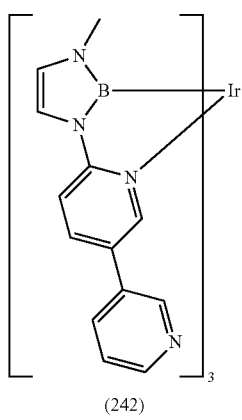
(242)
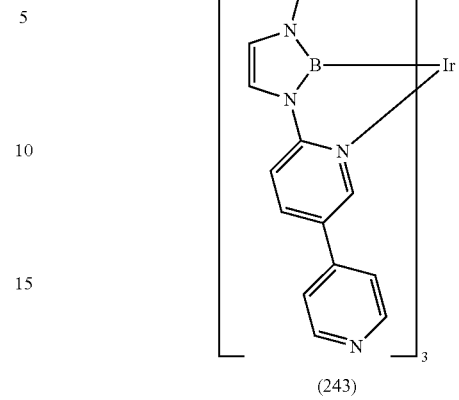
(243)
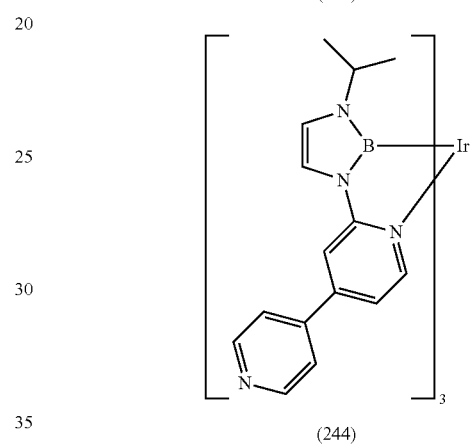
(244)
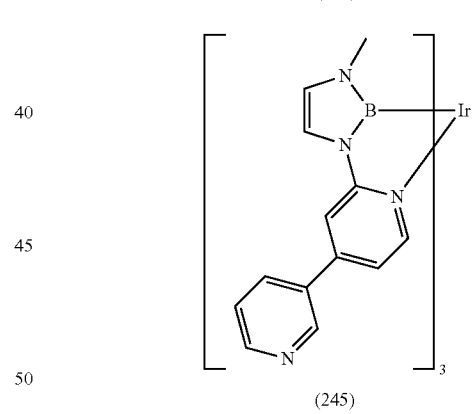
(245)
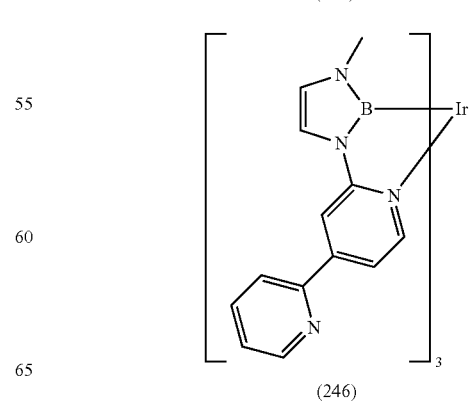
(246)

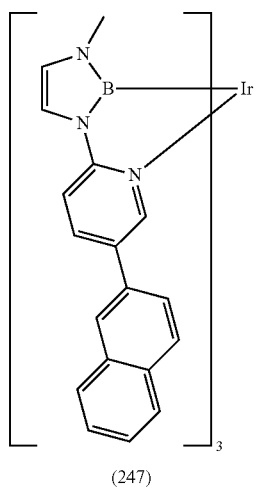
(247)
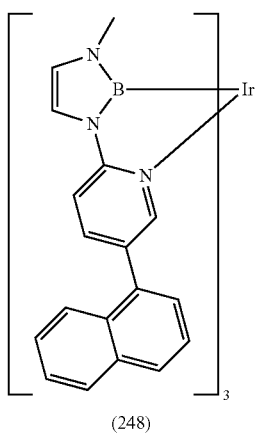
(248)
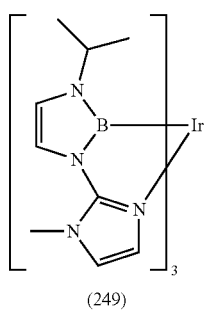
(249)
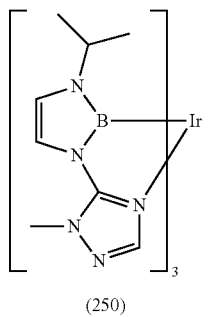
(250)
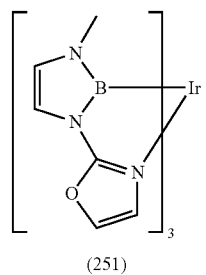
(251)
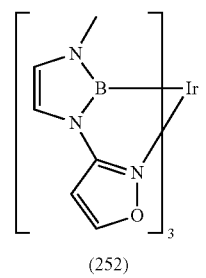
(252)
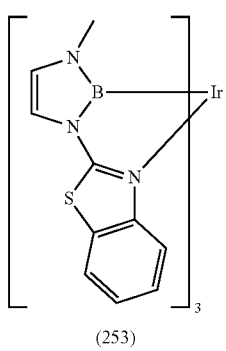
(253)
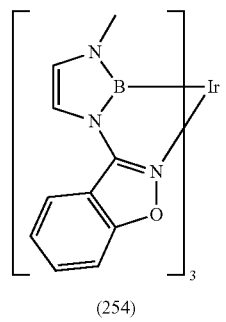
(254)
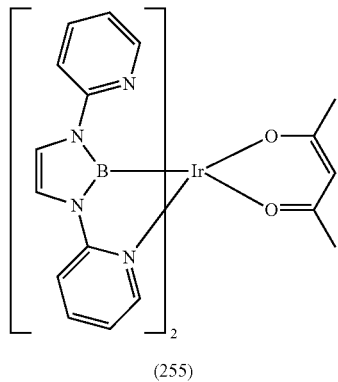
(255)

-continued
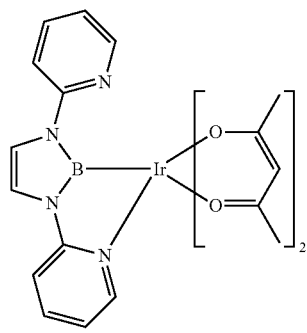
(256)
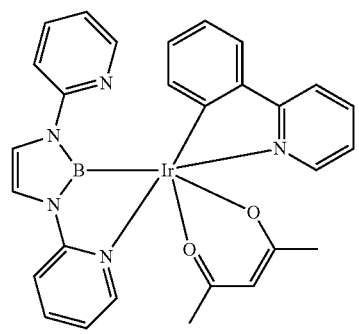
(257)
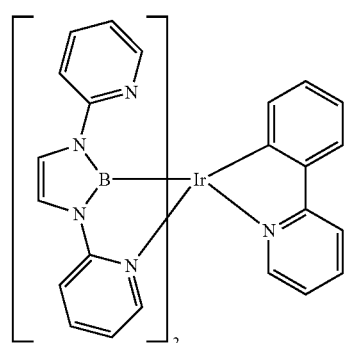
(258)
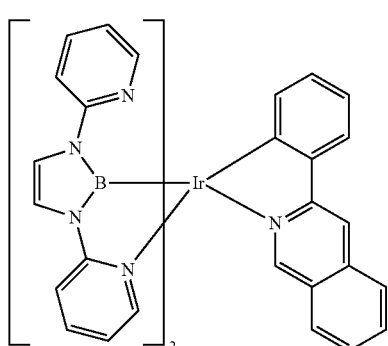
(259)
-continued
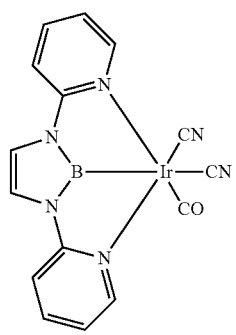
(260)
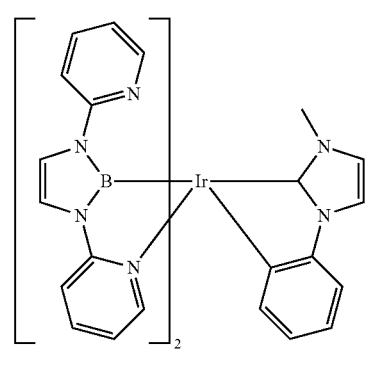
(261)
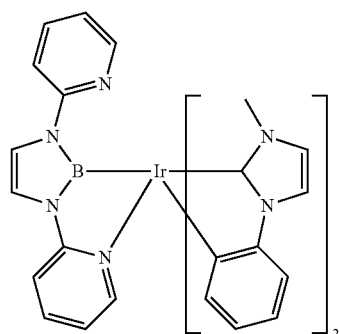
(262)
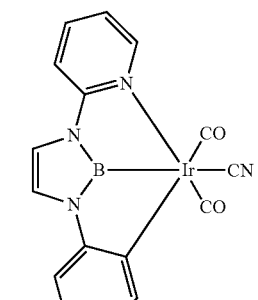
(263)

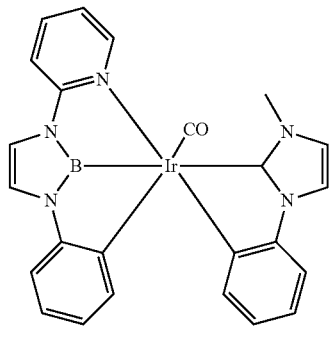
(264)
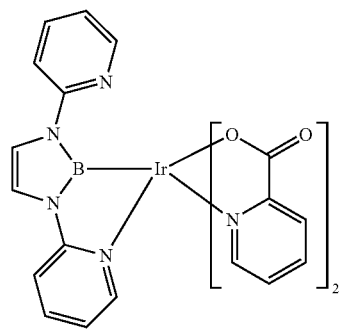
(265)
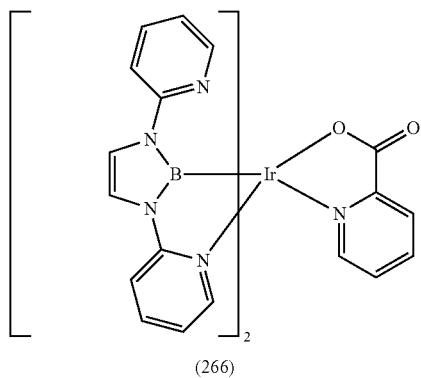
(266)
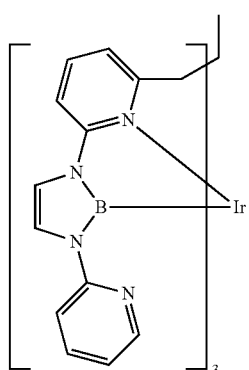
(267)
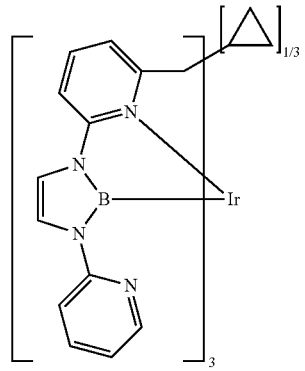
(268)
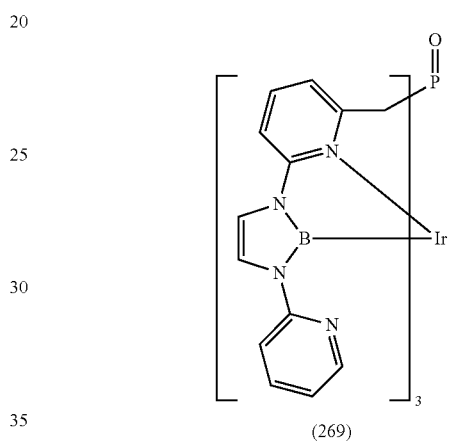
(269)
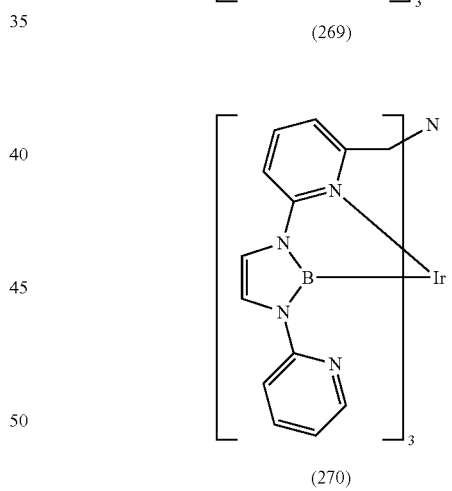
(270)
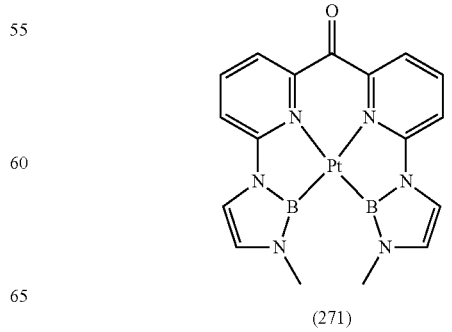
(271)

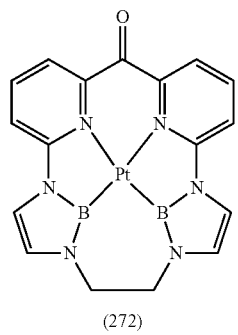
(272)
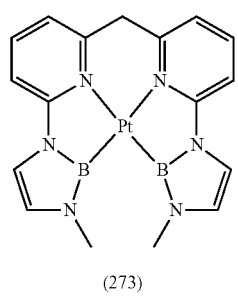
(273)
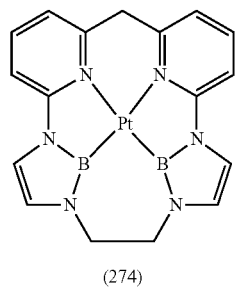
(274)
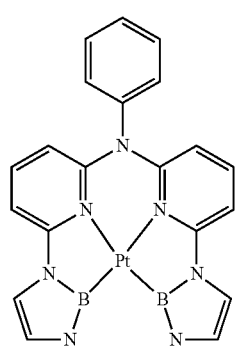
(275)
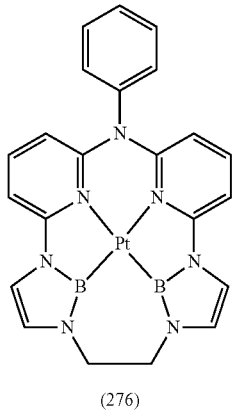
(276)
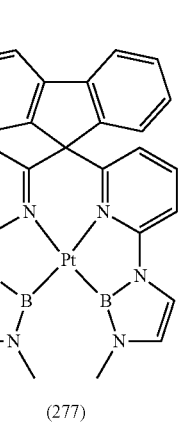
(277)
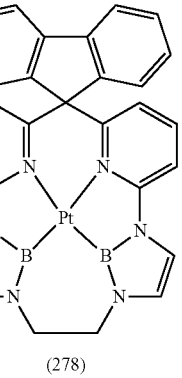
(278)
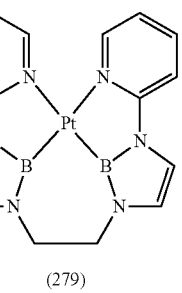
(279)

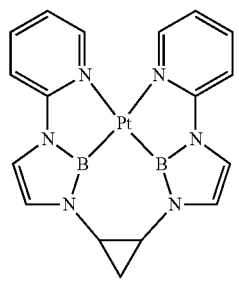
(280)
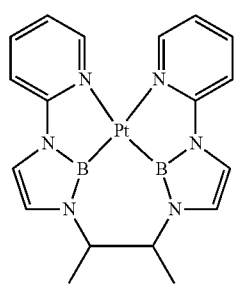
(281)
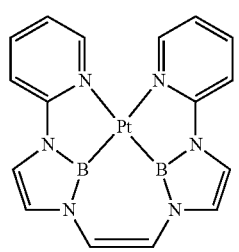
(282)
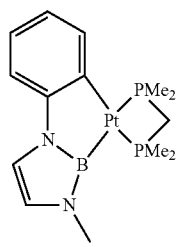
(283)
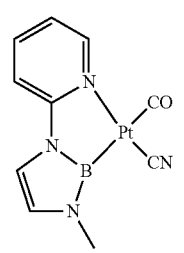
(284)
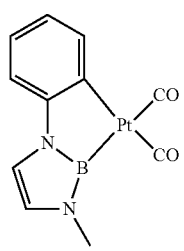
(285)
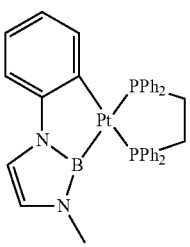
(286)
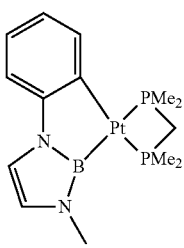
(287)
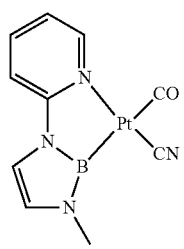
(288)
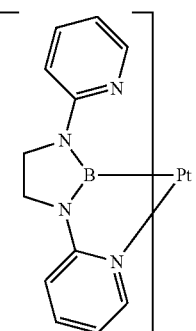
(289)

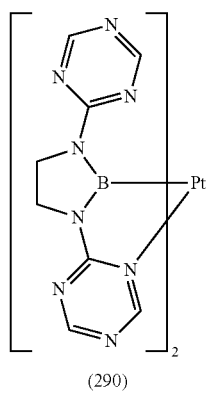
(290)
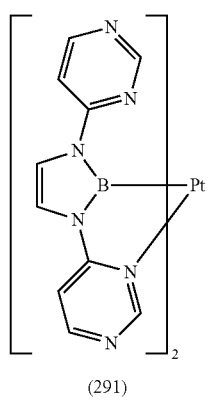
(291)
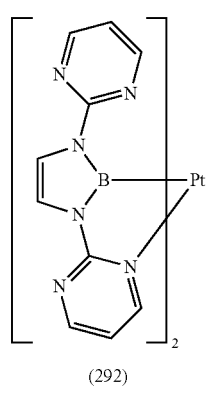
(292)
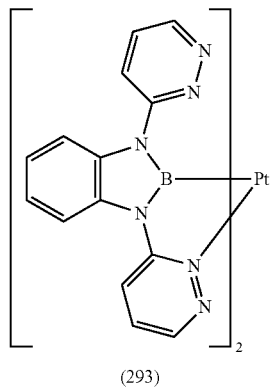
(293)
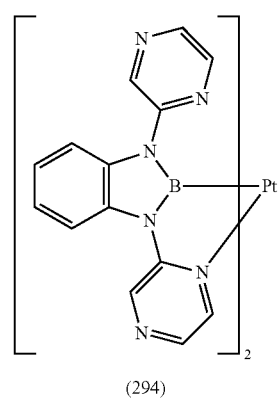
(294)
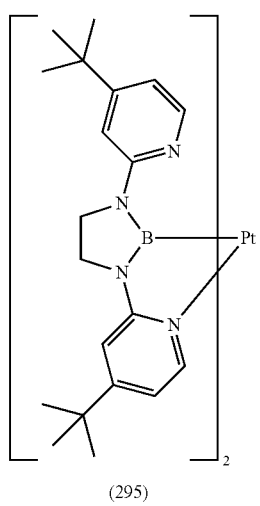
(295)
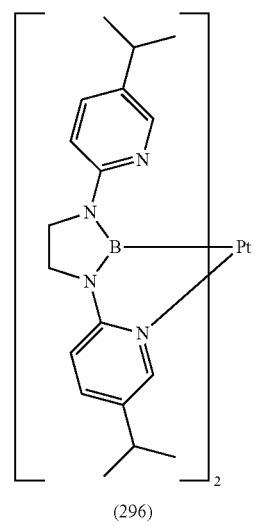
(296)

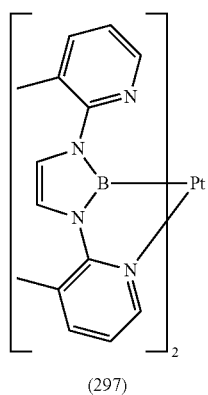
(297)
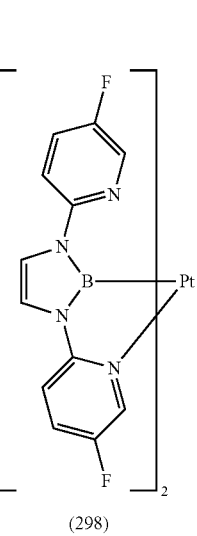
(298)
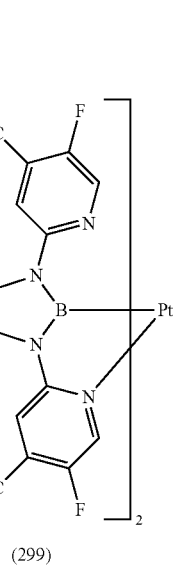
(299)
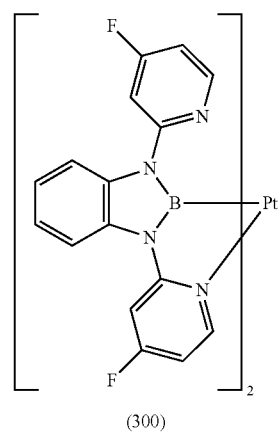
(300)
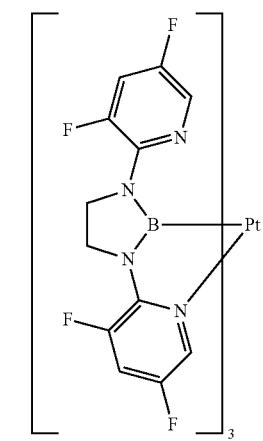
(301)
(302)

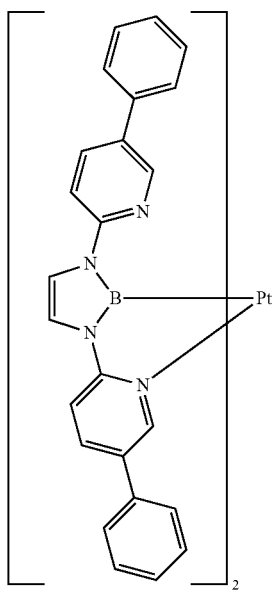
(303)
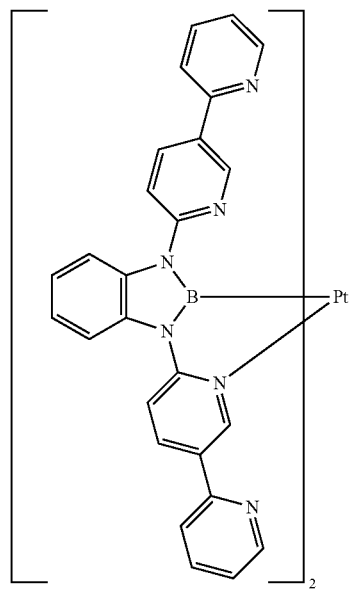
(305)
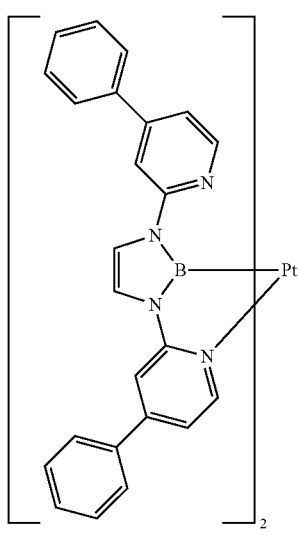
(304)
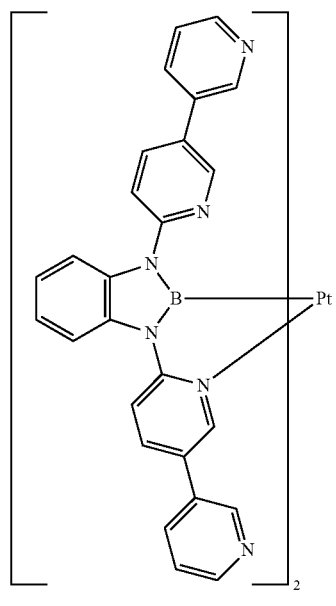
(306)

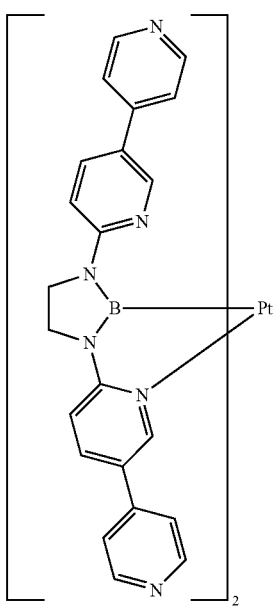
(307)
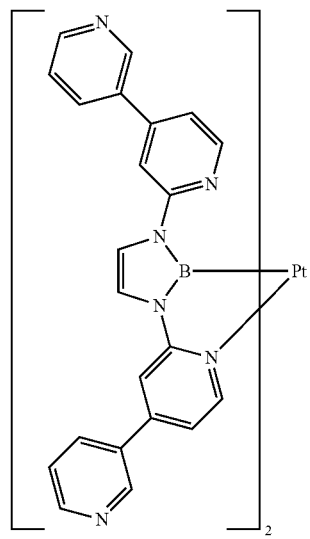
(309)
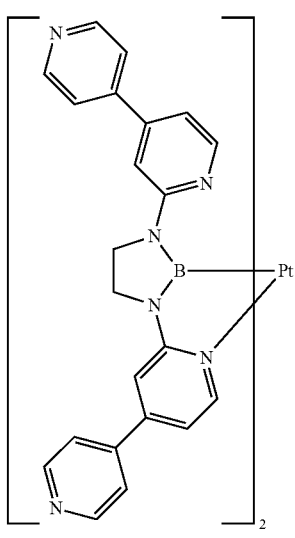
(308)
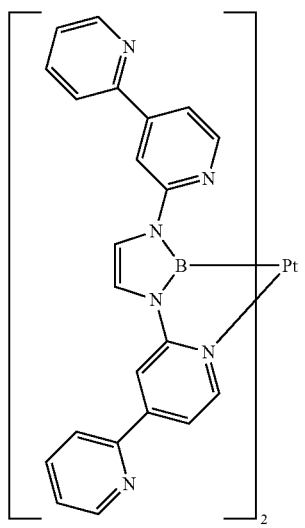
(310)

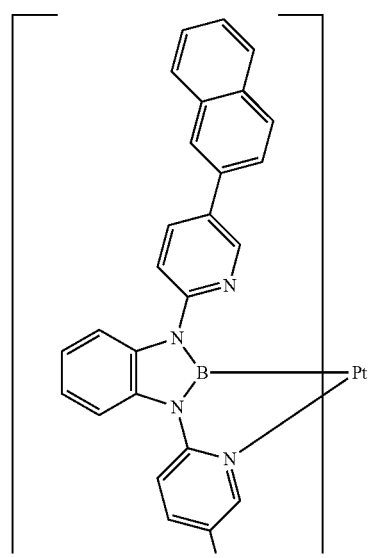
(311)
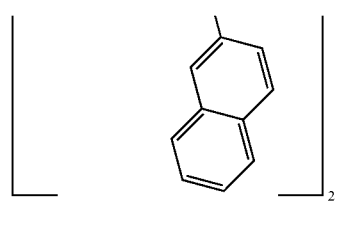
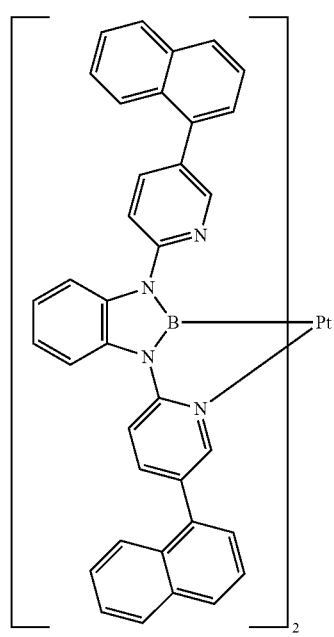
(312)
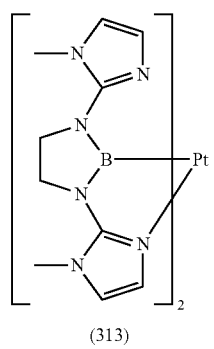
(313)
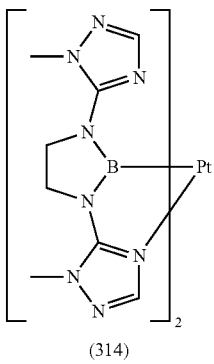
(314)
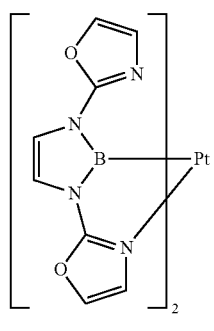
(315)
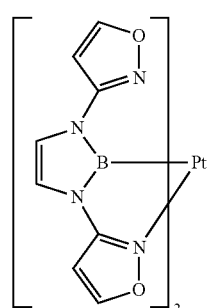
(316)

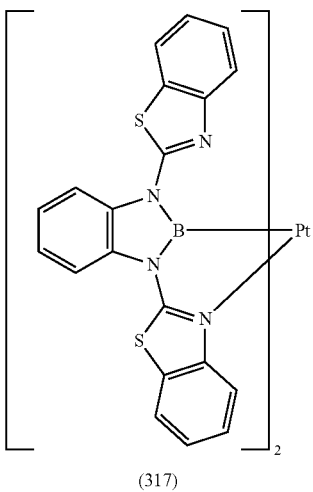
(317)
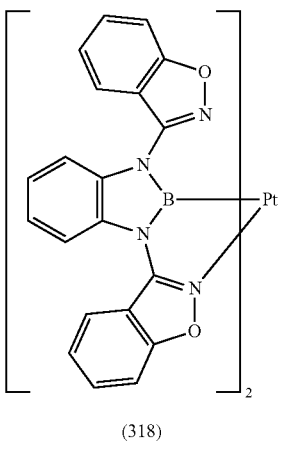
(318)
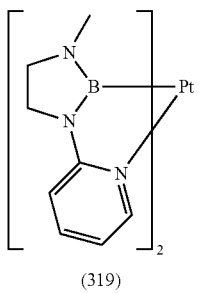
(319)
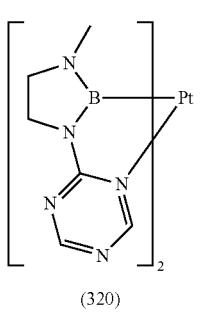
(320)
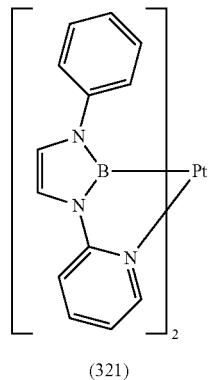
(321)
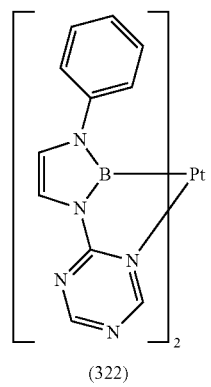
(322)
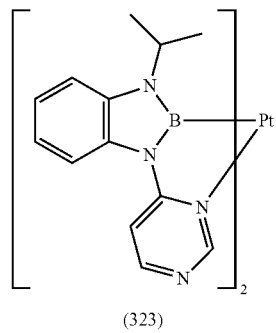
(323)
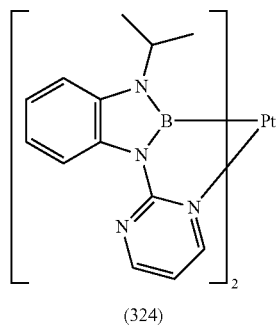
(324)

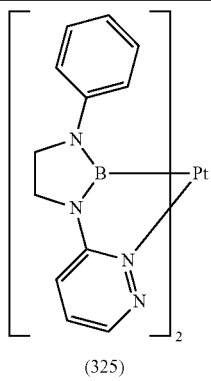
(325)
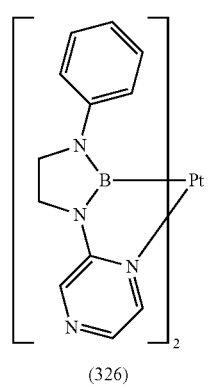
(326)
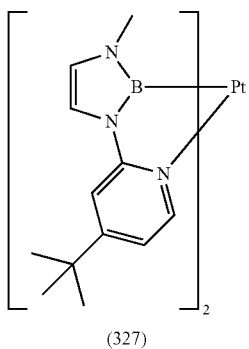
(327)
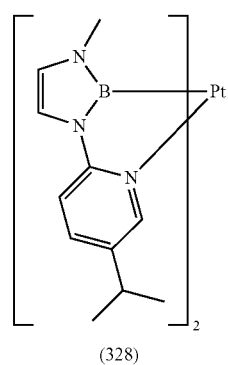
(328)
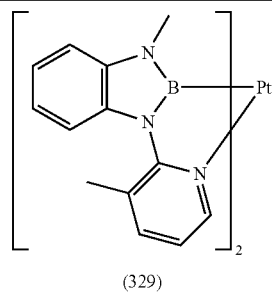
(329)
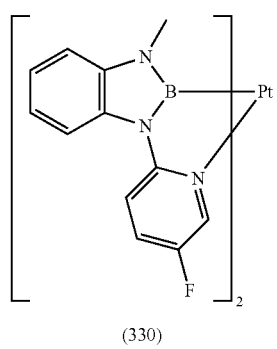
(330)
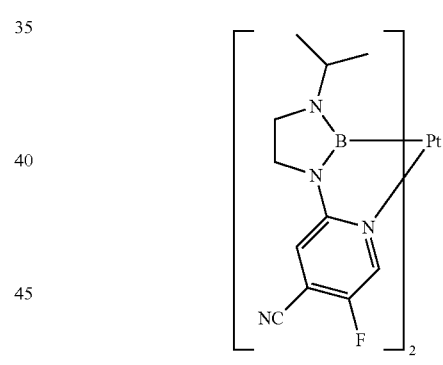
(331)
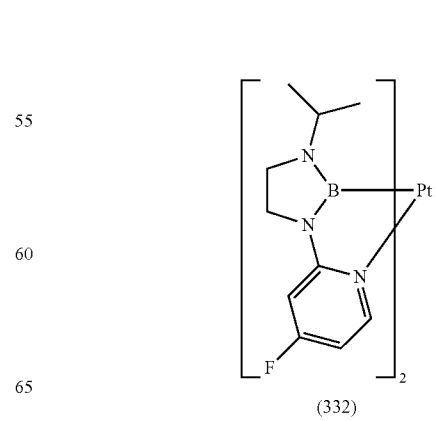
(332)

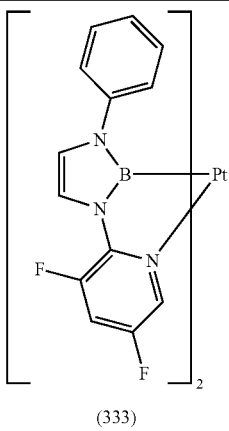
(333)
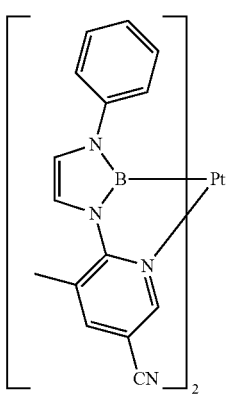
(334)
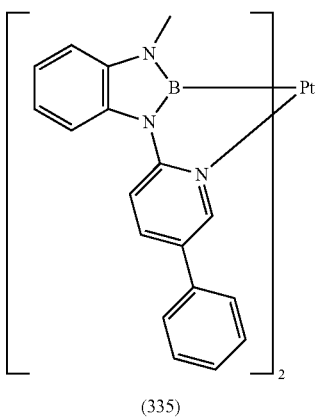
(335)
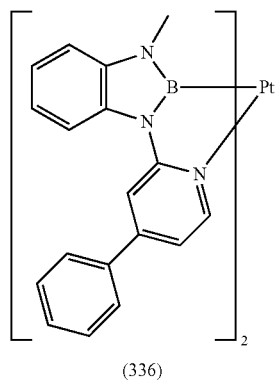
(336)
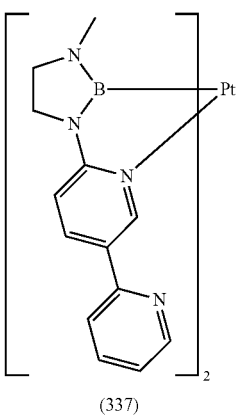
(337)
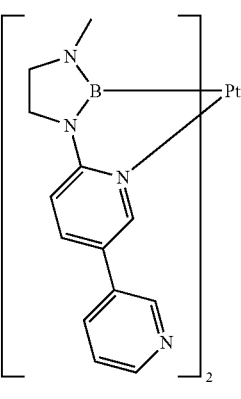
(338)
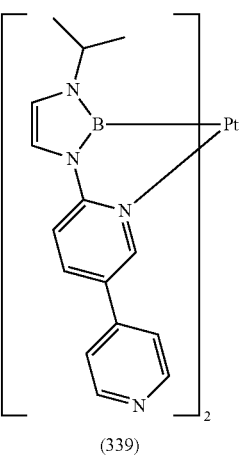
(339)

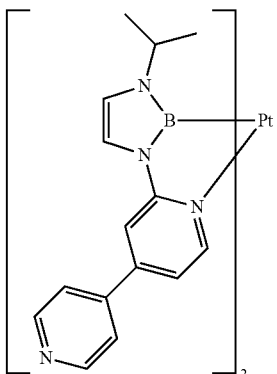
(340)
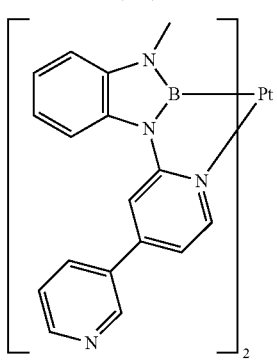
(341)
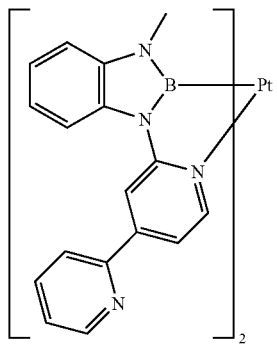
(342)
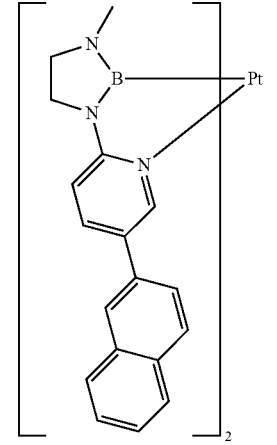
(343)
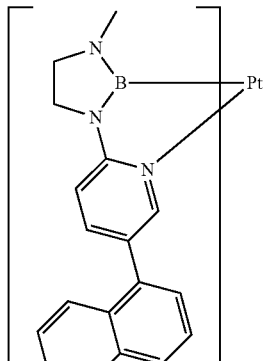
(344)
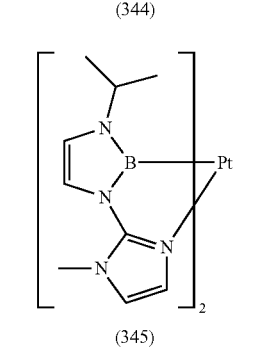
(345)
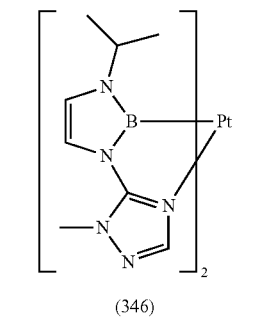
(346)
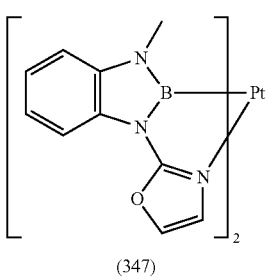
(347)
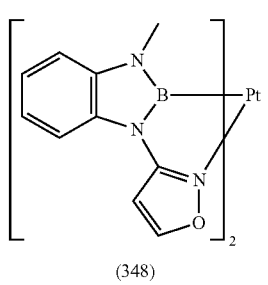
(348)

117
-continued
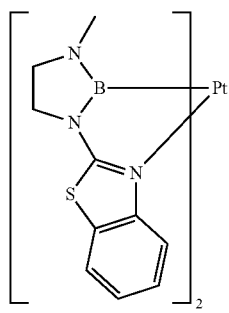
(349)
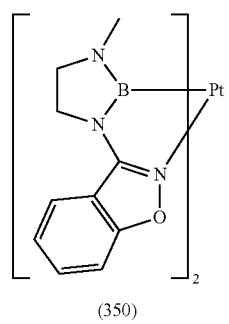
(350)
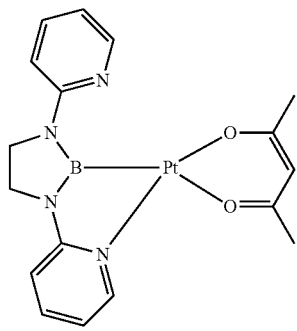
(351)
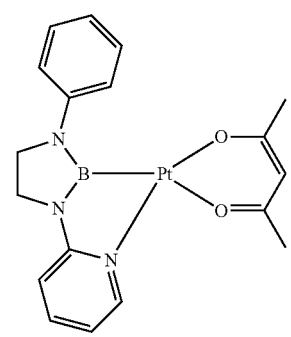
(352)
118
-continued
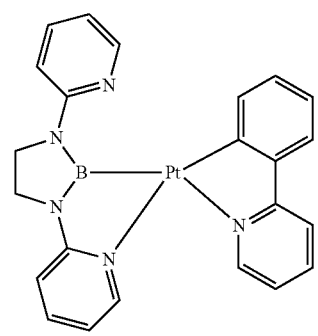
(353)
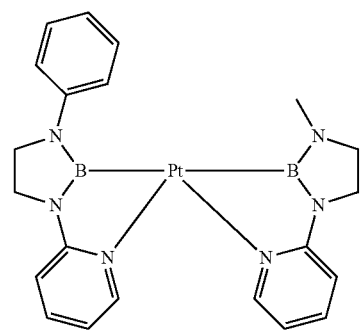
(354)
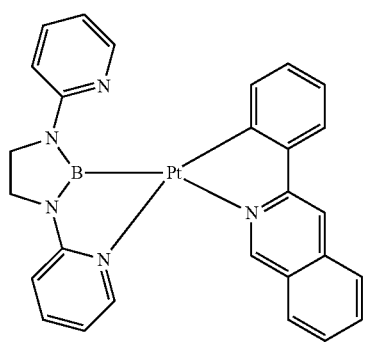
(355)
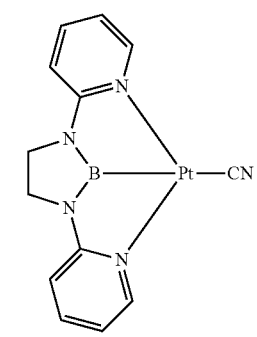
(356)

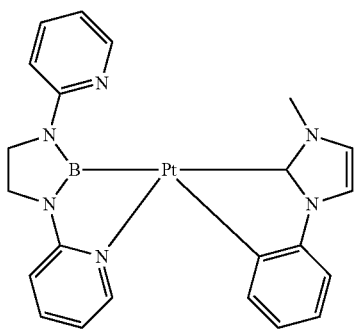

(357)

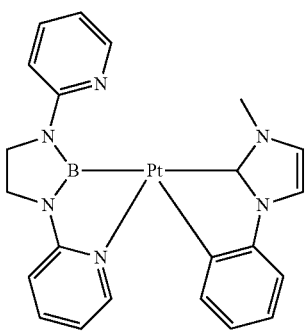

(358)

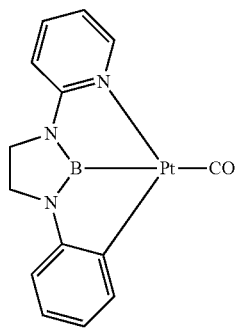

(359)

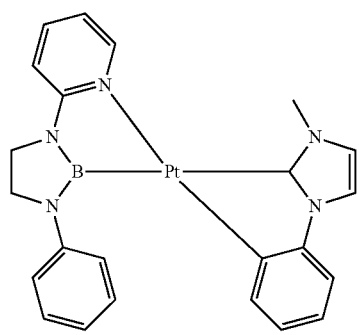

(360)

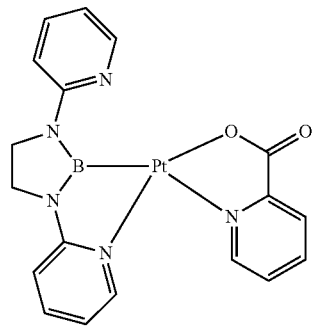

(361)

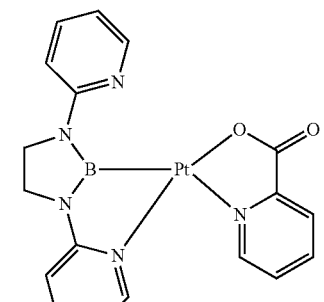

(362)

The complexes of the formula I described above and the preferred embodiments indicated above are preferably used as active component in the electronic device. Preferred electronic devices are selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors and organic laser diodes (O-lasers). Particular preference is given to organic electroluminescent devices.

Active components are generally the organic, organometallic or inorganic materials introduced between the anode and cathode, for example charge-injection, charge-transport or charge-blocking materials, but in particular emission materials and matrix materials. The compounds according to the invention exhibit particularly good properties for these functions, in particular as emission material in organic electroluminescent devices, as described in greater detail below. Organic electroluminescent devices are therefore a preferred embodiment of the invention.

The organic electroluminescent device preferably comprises a cathode, an anode and at least one emitting layer, where the compound of the general formula I is preferably in the form of an emitting compound in the emitting layer or where the compound of the general formula I is in the form of a matrix material for an emitting compound in the emitting layer, particularly preferably in the form of an emitting compound.

The organic electronic device may comprise further layers, selected from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions.

It is likewise possible for interlayers, which have, for example, an exciton-blocking function, to be introduced between two emitting layers or also between other layers. However, it should be pointed out that each of these layers does not necessarily have to be present. The organic electroluminescent device may comprise one emitting layer or a plurality of emitting layers, where at least one emitting layer comprises at least one compound of the formula I. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

In a preferred embodiment of the invention, the electronic device comprises the compound of the formula I or the preferred embodiments indicated above as emitting compound in an emitting layer.

If the compound of the formula I is employed as emitting compound in an emitting layer, it is preferably employed in combination with one or more matrix materials. The mixture of the compound of the formula I and the matrix material comprises between 1 and 99% by vol., preferably between 2 and 90% by vol., particularly preferably between 3 and 40% by vol., especially between 5 and 15% by vol., of the compound of the formula I, based on the mixture as a whole comprising emitter and matrix material. Correspondingly, the mixture comprises between 99 and 1% by vol., preferably between 98 and 10% by vol., particularly preferably between 97 and 60% by vol., especially between 95 and 85% by vol., of the matrix material, based on the mixture as a whole comprising emitter and matrix material.

Suitable matrix materials for the compounds according to the invention are ketones, phosphine oxides, sulfoxides and sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl), mCBP or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazoles, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the unpublished application DE 102008036982.9, WO 07/063754 or WO 08/056746, or zinc complexes, for example in accordance with EP 652273 or WO 09/062578. The compounds of the formula I of the present application are furthermore suitable as matrix materials, as described in greater detail below. In general, all matrix materials as employed in accordance with the prior art for phosphorescent emitters in organic electroluminescent devices can also be employed for the compounds according to the invention. It is likewise possible to employ mixtures of these matrix materials.

It is also possible for the organic electroluminescent device not to comprise a separate hole-transport layer or for it to comprise a metal complex, which is identical or similar to the complex employed in the emitting layer, as hole-transport material in the hole-transport layer.

In a further preferred embodiment of the invention, the compound of the formula I or the preferred embodiments indicated above are employed as matrix material for an emitting compound in an emitting layer.

In a further preferred embodiment of the invention, the electroluminescent device according to the invention comprises a matrix material and furthermore at least two phosphorescent emitters in the emitting layer, where at least one of the two phosphorescent emitters is a compound of the formula (I) given above. The phosphorescent emitter which emits at shorter wavelength serves here as matrix for the phosphorescent emitter which emits at longer wavelength. The compound of the formula (I) here can be the compound emitting at shorter wavelength or the compound emitting at longer wavelength. Likewise, both phosphorescent compounds can be complexes of the formula (I). It is also possible for both complexes then to be luminescent.

If the compound of the formula I or the preferred embodiments indicated above are employed as matrix material for an emitting compound in an emitting layer, they are preferably employed in combination with one or more phosphorescent materials (triplet emitters) or fluorescent materials (singlet emitters). Preferred emitting materials are phosphorescent materials. For the purposes of this invention, phosphorescence is taken to mean the luminescence from an excited state of relatively high spin multiplicity, i.e. a spin state>1, in particular from an excited triplet state or from an MLCT mixed state. For the purposes of the present invention, all luminescent transition-metal complexes, in particular all luminescent iridium, platinum and copper compounds, are regarded as phosphorescent materials. The mixture of the compound of the formula I or the preferred embodiment indicated above and the emitting compound then comprises between 99 and 1% by vol., preferably between 98 and 10% by vol., particularly preferably between 97 and 60% by vol., especially between 95 and 85% by vol., of the compound of the formula I or the preferred embodiment indicated above, based on the mixture as a whole comprising emitter and matrix material. Correspondingly, the mixture comprises between 1 and 99% by vol., preferably between 2 and 90% by vol., particularly preferably between 3 and 40% by vol., especially between 5 and 15% by vol., of the emitter, based on the mixture as a whole comprising emitter and matrix material. It is likewise possible to employ a compound of the formula (I) and a further compound jointly as matrix material.

The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244 or WO 09/118087. Suitable emitters are furthermore the compounds of the formula I indicated above and the preferred embodiments indicated above. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without an inventive step.

In a further preferred embodiment of the invention, the compound of the formula I or the preferred embodiments indicated above are employed as hole-blocking material in a hole-blocking layer and/or as electron-transport material in an electron-transport layer. The emitting layer here may be fluorescent or phosphorescent.

Preference is furthermore given to an organic electroluminescent device, characterised in that one or more layers are applied by means of a sublimation process, in which the materials are applied by vapour deposition in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose.

Hybrid processes, in which one or more layers are applied from solution and one or more other layers are applied by vapour deposition, are also possible.

These processes are generally known to the person skilled in the art and can be applied by him without problems to organic electroluminescent devices according to the invention comprising compounds of the formula I or the preferred embodiments indicated above.

The preferred compounds (metal complexes) of the formula I mentioned above are novel and are therefore likewise a subject-matter of the present invention. The preferences and embodiments indicated above for the organic electronic devices preferably also apply entirely analogously to the compounds according to the invention.

For the purposes of the present invention, particular preference is given to compounds of the general formula I

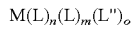
M(L)$_n$(L')$_m$(L'')$_o$    I, where the compound of the general formula I contains a moiety M(L)$_n$ of the formula II, III and/or IV:

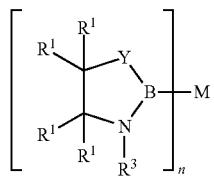
formula II

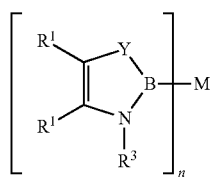
formula III

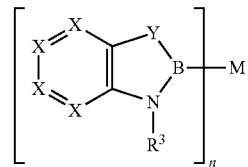
formula IV where the following applies to the symbols and indices used:
M is a metal;
Y is on each occurrence, in each case independently of one another, NR$^3$, O or S;
X is on each occurrence, in each case independently of one another, CR$^1$ or N;
R$^1$ is on each occurrence, in each case independently of one another, H, D, F, Cl, Br, I, CHO, N(R$^2$)$_2$, N(Ar)$_2$, C(=O)Ar, P(=O)(Ar)$_2$, S(=O)Ar, S(=O)$_2$Ar, CR$^2$=C(R$^2$)$_2$, CR$^2$=CR$^2$Ar, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems, where two or more adjacent substituents R$^1$ may also form a mono- or polycyclic, aliphatic or aromatic ring system with one another;
R$^2$ is on each occurrence, in each case independently of one another, H, D, F or an aliphatic, aromatic and/or heteroaromatic hydrocarbon radical having 1 to 20 C atoms, in which, in addition, one or more H atoms may be replaced by F; two or more substituents R$^2$ here may also form a mono- or polycyclic, aliphatic or aromatic ring system with one another;
R$^3$ is on each occurrence, in each case independently of one another, an aliphatic hydrocarbon radical having 1 to 20 C atoms or an aromatic or heteroaromatic ring system having 5 to 30 aromatic ring atoms, in which, in addition, one or more H atoms may be replaced by R$^1$, characterised in that at least one radical R$^3$ represents a coordinating group which contains a charged or uncharged exocyclic or endocyclic donor atom D which bonds to the metal M;
a plurality of part-ligands L here may form a polydentate or polypodal ligand together with one another or L with L' and/or L'', optionally via a link via R$^3$;
Ar is on each occurrence, in each case independently of one another, an aromatic or heteroaromatic ring system having 5 to 30 aromatic ring atoms, which may be substituted by one or more non-aromatic radicals R$^1$;
where furthermore n=1 to 6 (1, 2, 3, 4, 5, 6), o=0 to 5 (0, 1, 2, 3, 4, 5) and m=0 to 5 (0, 1, 2, 3, 4, 5) if M has the coordination number 6, and n=1 to 5 (1, 2, 3, 4, 5), o=0 to 4 (0, 1, 2, 3, 4) and m=0 to 4 (0, 1, 2, 3, 4) if M has the coordination number 5, and n=1 to 4 (1, 2, 3, 4), m=0 to 3 (0, 1, 2, 3) and o=0 to 3 (0, 1, 2, 3) if M has the coordination number 4.

It is particularly preferred here for $R^3$ on each occurrence, in each case independently of one another, to represent an aromatic or heteroaromatic ring system having 5 to 30 aromatic ring atoms, in which, in addition, one or more H atoms may be replaced by $R^1$, where at least one group $R^3$ contains a charged or uncharged exocyclic or endocyclic donor atom D which bonds to the metal M; a plurality of part-ligands L or L with L' and/or L'', optionally via a link via $R^3$, may together form a polydentate or polypodal ligand. $R^3$ is particularly preferably selected from structures of the formulae (1) to (24).

Otherwise, the same preferences apply as indicated for the organic electronic device.

The present invention again furthermore relates to a process for the preparation of the compounds of the formula I by reaction of the corresponding free ligand of the formula V, VI or VII with metal compounds of the formula (47), (48) or (49) given above.

The compounds of the general formula I according to the invention can be used as emitter compound, as matrix material, as hole-blocking material and/or as electron-transport material in an electronic device, in particular in an organic electroluminescent device.

The invention likewise relates to the ligands L, which are a valuable intermediate for the synthesis of the metal complexes according to the invention.

The invention thus relates to a ligand L of the general formula V, VI or VII:

formula V

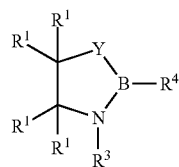

formula VI

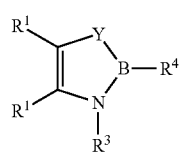

formula VII

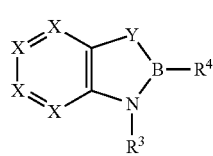

where $R^1$, $R^3$ and Y have the meanings indicated above under product protection, in particular the preferred embodiments indicated above, and furthermore:

$R^4$ is H or halogen;

where the following compounds are excluded:

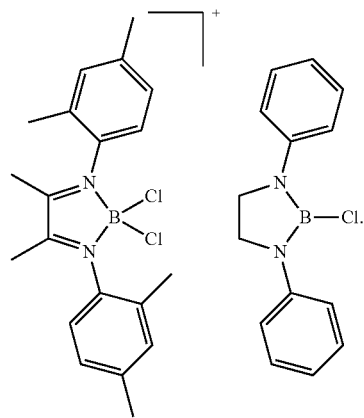

In an embodiment of the invention, the ligand L conforms to the formula Va, VIa, VIIa, Vb, VIb or VIIb:

Va

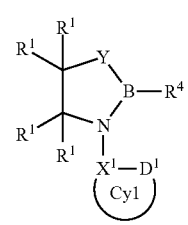

VIa

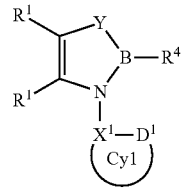

VIIa

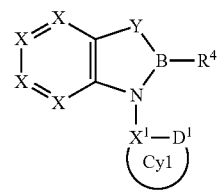

Vb

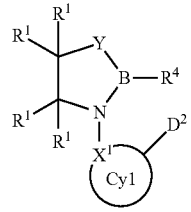

VIb

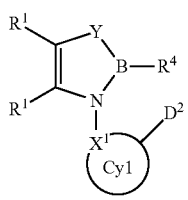

-continued

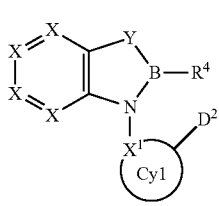
VIIb where the symbols and indices have the meanings indicated above.

The donor atom $D^1$ is preferably selected from B, C, N, O and S, and the donor group $D^2$ is preferably selected from O, S, $NR^1$, $N(R^1)_2$, $PR^1$ and $P(R^1)_2$.

In a further preferred embodiment of the invention, Y=$NR^3$.

Furthermore, the preferred embodiments indicated above for the electronic device apply.

Preferred structures $R^3$ or Cy1 of the ligand L are selected from the following structures (1) to (24):

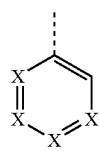 (1)

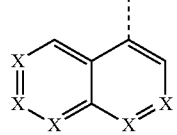 (2)

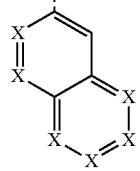 (3)

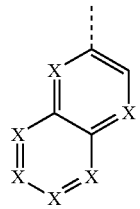 (4)

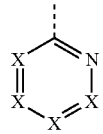 (5)

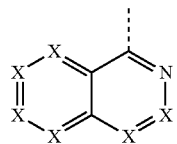 (6)

-continued

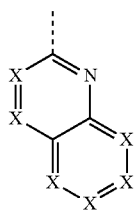 (7)

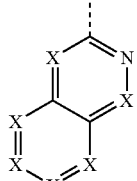 (8)

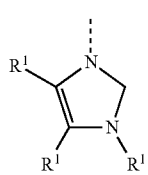 (9)

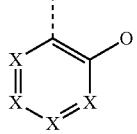 (10)

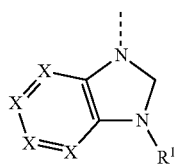 (11)

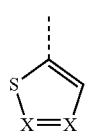 (12)

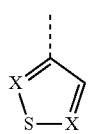 (13)

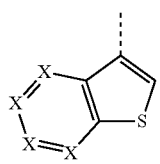 (14)

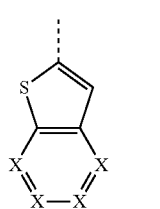 (15)

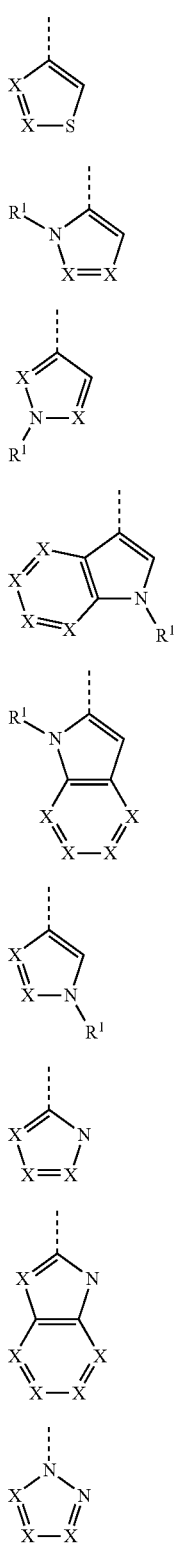
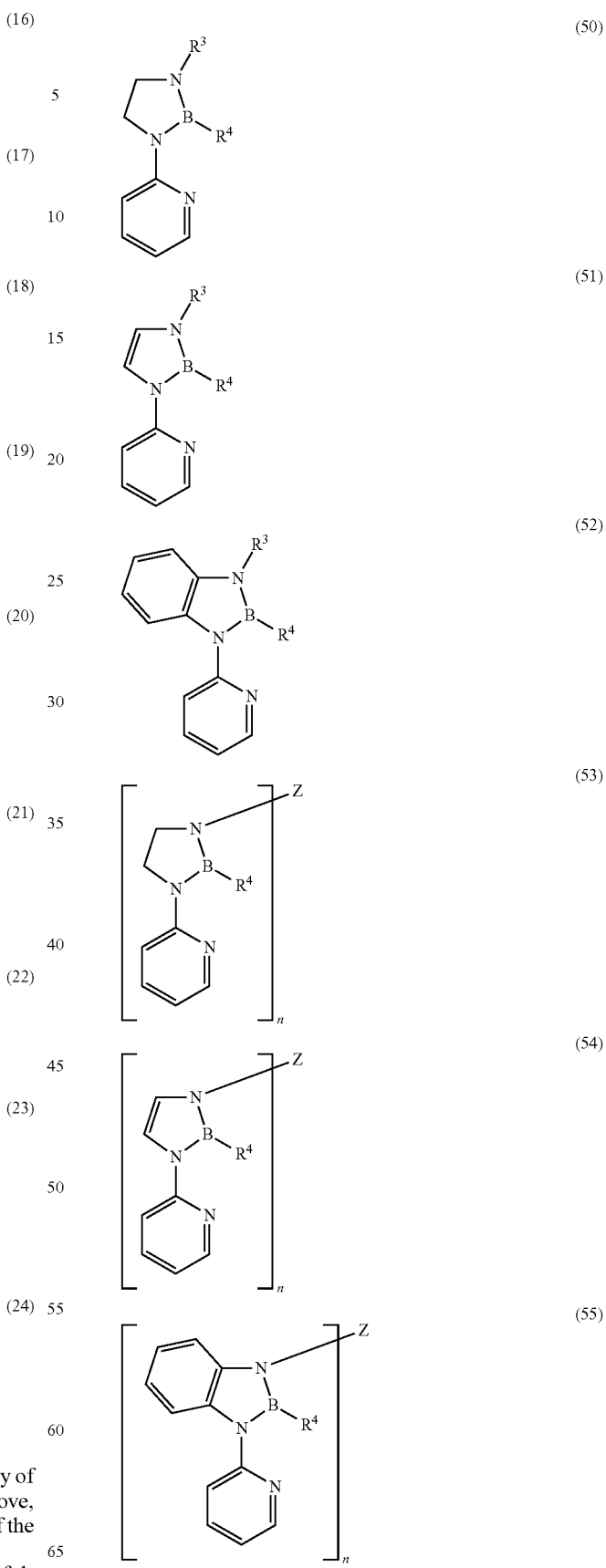
where X is on each occurrence, in each case independently of one another, $CR^1$ or N, $R^1$ has the meaning indicated above, and the dashed line denotes a bond to the nitrogen atom of the boron/nitrogen heterocycle.
Particularly preferred ligands L are selected from the following structures:

where the symbols and indices used have the meanings indicated above.

The ligand L serves as intermediate for the preparation of the metal complexes of the general formula I. The invention thus also relates to the use of the ligand L of the general formula V, VI or VII:

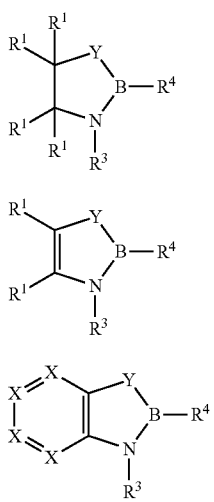

formula V formula VI formula VII for the preparation of a compound of the general formula I as defined above, where the symbols and indices used have the meanings indicated above.

In a preferred embodiment of the invention, the ligand conforms to the formula Va, VIa, VIIa, Vb, VIb or VIIb indicated above.

In a preferred embodiment of the invention, Y=NR$^3$.

Preferred structures R$^3$ or Cy1 of the ligand L are selected from the structures (1) to (24) indicated above.

Particularly preferred ligands L are the structures (50) to (55) indicated above.

The above-described compounds of the formula (I) according to the invention, in particular compounds which are substituted by reactive leaving groups, such as bromine, iodine, boronic acid or boronic acid ester, can be used as monomers for the generation of corresponding oligomers, dendrimers or polymers. The oligomerisation or polymerisation here preferably takes place via the halogen functionality or the boronic acid functionality.

The invention therefore furthermore relates to oligomers, polymers or dendrimers comprising one or more compounds of the formula I, where one or more bonds are present from the complex of the formula I to the polymer, oligomer or dendrimer. Depending on the linking of the compound of the formula I, the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

The same preferences as described above apply entirely analogously to the recurring units of the formula I in oligomers, dendrimers and polymers.

For the preparation of the oligomers or polymers, the monomers according to the invention are homopolymerised or copolymerised with further monomers. Preference is given to copolymers, where the units of the formula I are preferably present to the extent of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and transindenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The proportion of these units in total is preferably in the region of at least 50 mol %. The polymers, oligomers and dendrimers may also contain further units, for example hole-transport units, in particular those based on triarylamines, and/or electron-transport units.

Furthermore, the metal complexes according to the invention may also be further functionalised and thus converted into extended metal complexes. An example which may be mentioned here is functionalisation using arylboronic acids by the SUZUKI method or using primary or secondary amines by the HARTWIG-BUCHWALD method.

The electronic devices according to the invention, in particular organic electroluminescent devices, are distinguished by the following surprising advantages over the prior art:

1. In contrast to many metal complexes in accordance with the prior art, which undergo partial or complete pyrolytic decomposition on sublimation, the compounds according to the invention have high thermal stability.
2. Organic electroluminescent devices comprising compounds of the formula I as emitting materials have an excellent lifetime.
3. Blue-phosphorescent complexes which have good colour coordinates and a long lifetime on use in organic electroluminescent devices are accessible. This is a significant advance over the prior art, since blue-phosphorescent devices were hitherto usually only accessible with poor colour coordinates and in particular a poor lifetime.
4. The compounds according to the invention, employed in organic electroluminescent devices, result in high efficiencies and in steep current/voltage curves.

These above-mentioned advantages are not accompanied by an impairment of the other electronic properties.

The invention is explained in greater detail by the following examples, without wishing to restrict it thereby. The person skilled in the art will be able to prepare further complexes according to the invention from the descriptions without an inventive step and use them in organic electronic devices or use the process according to the invention.

EXAMPLES

The following syntheses are, unless indicated otherwise, carried out under a protective-gas atmosphere in dried solvents. The solvents and reagents can be purchased from ALDRICH or ABCR.

Precursors 1-4: Synthesis of Symmetrically N,N'-Substituted o-phenyl-enediamines The symmetrically N,N'-substituted o-phenylenediamines indicated below are prepared from o-dibromobenzene and a corresponding amine analogously to Tetrahedron Letters 2004, 45, 6851-6853.

| Prec. | Amine | o-Phenylenediamine | Yield |
|---|---|---|---|
| 1 | 2-aminopyrimidine<br>109-12-6 | N,N'-di(pyrimidin-2-yl)-o-phenylenediamine | 35% |
| 2 | 5-fluoro-2-aminopyridine<br>21717-96-4 | N,N'-bis(5-fluoropyridin-2-yl)-o-phenylenediamine | 21% |
| 3 | 5-phenyl-2-aminopyridine<br>33421-40-8 | N,N'-bis(5-phenylpyridin-2-yl)-o-phenylenediamine | 63% |
| 4 | 2-aminobenzothiazole<br>84293-42-5 | N,N'-bis(benzothiazol-2-yl)-o-phenylenediamine | 12% |

Precursors 5-12: Synthesis of Asymmetrically N,N'-Substituted o-phenylenediamines The asymmetrically N,N'-substituted o-phenylenediamines indicated below are prepared from a bromide and an amine analogously to Organometallics 2009, 28, 5244-5252.

| Prec. | Bromide | Amine | o-Phenylenediamine | Yield |
|---|---|---|---|---|
| 5 | N-methyl-2-bromoaniline<br>6832-87-7 | 2-aminopyridine<br>504-29-0 | N-methyl-N'-(pyridin-2-yl)-o-phenylenediamine | 39% |
| 6 | N-methyl-2-bromoaniline<br>6832-87-7 | 2-aminobenzothiazole<br>84293-42-5 | N-methyl-N'-(benzothiazol-2-yl)-o-phenylenediamine | 17% |
| 7 | N-phenyl-2-bromoaniline<br>J. Org. Chem. 2009, 74, 4490-4498 | 2-aminopyridine<br>504-29-0 | N-phenyl-N'-(pyridin-2-yl)-o-phenylenediamine | 78% |

-continued

| Prec. | Bromide | Amine | o-Phenylenediamine | Yield |
|---|---|---|---|---|
| 8 | J. Chem. Soc., Perkin Trans. I 1999, 1505-1510. | 15995-42-3 | | 22% |
| 9 | 760177-68-2 | 534-85-0 | | 29% |
| 10 | 760177-68-2 | 4760-34-3 | | 27% |

| Prec. | Bromide | Amine | o-Phenylenediamine | Yield |
|---|---|---|---|---|
| 11 | 881810-86-2 | 534-85-0 | | 52% |
| 12 | 881810-86-2 | 4760-34-3 | | 48% |

Precursors 13-25: Synthesis of 2-bromobenzo-1,3,2-diazaboroles

The 2-bromobenzo-1,3,2-diazaboroles indicated below are prepared from the corresponding N,N'-substituted o-phenylenediamines by reaction with boron tribromide analogously to J. Org. Chem. 1962, 27, 4701-4702.

| Prec. | o-Phenylenediamine | Benzo-1,3,2-diazaborole | Yield |
|---|---|---|---|
| 13 | Russian Journal of Organic Chemistry 2007, 43, 1696-1697. | | 76% |
| 14 | | | 53% |

-continued

| Prec. | o-Phenylenediamine | Benzo-1,3,2-diazaborole | Yield |
|---|---|---|---|
| 15 | | | 51% |
| 16 | | | 69% |
| 17 | | | 36% |
| 18 | | | 39% |
| 19 | | | 22% |
| 20 | | | 72% |
| 21 | | | 43% |

-continued
| Prec. | o-Phenylenediamine | Benzo-1,3,2-diazaborole | Yield |
|---|---|---|---|
| 22 | 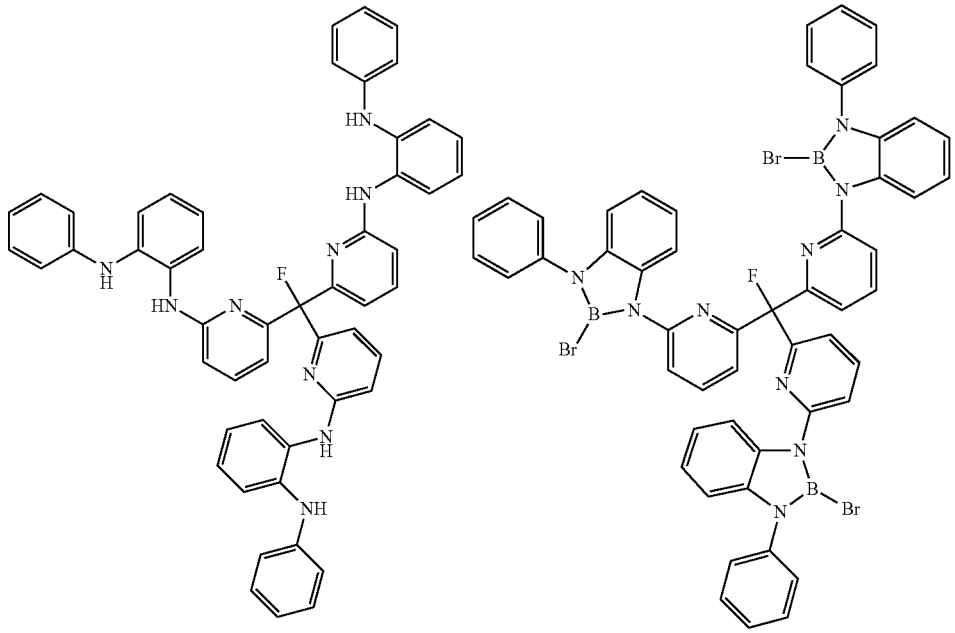 | | 35% |
| 23 | 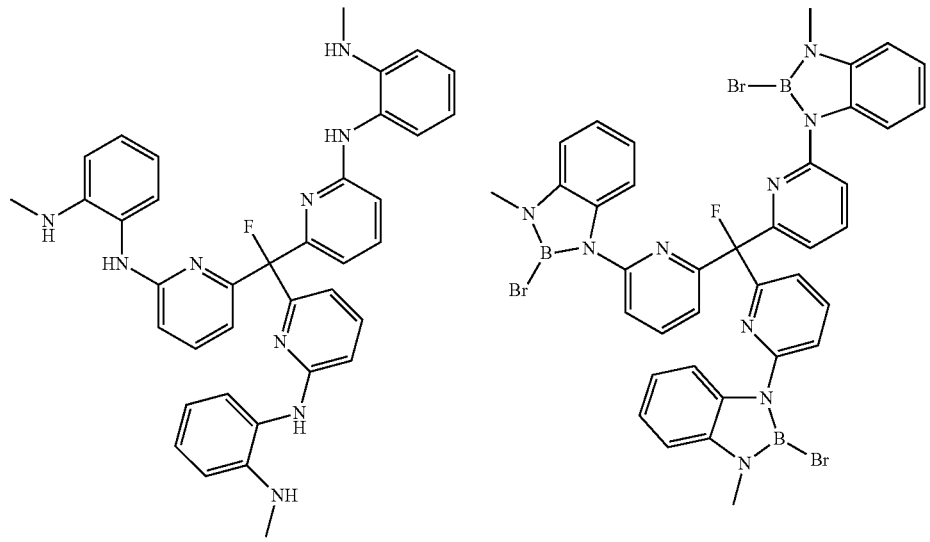 | | 29% |

| Prec. | o-Phenylenediamine | Benzo-1,3,2-diazaborole | Yield |
|---|---|---|---|
| 24 | | | 61% |
| 25 | | | 52% |

Precursors 26-27: Synthesis of 2-bromo-1,3,2-diazaboroles

The 2-bromo-1,3,2-diazaboroles indicated below are prepared from the corresponding diimines by reduction using magnesium and subsequent reaction with boron tribromide analogously to Science 2006, 314, 113-116.

| Prec. | Diimine | 1,3,2-Diazaborole | Yield |
|---|---|---|---|
| 26 | analogously to Organometallics 2000, 19, 4944-4956. | | 43% |
| 27 | analogously to Organometallics 2000, 19, 4944-4956. | | 56% |

Precursors 28-29: Synthesis of
2-bromo-1,3,2-diazaborolidines

The 2-bromo-1,3,2-diazaborolidines indicated below are prepared from the corresponding diamines by reaction with a boron tribromide/triethylamine adduct analogously to Organometallics 2005, 24, 5455-5463.

| Prec. | Diamine | 1,3,2-Diazaborolidine | Yield |
|---|---|---|---|
| 28 | (structure) Russian Journal of Organic Chemistry 2007, 43, 1696-1697. | (structure) | 66% |
| 29 | (structure) 2 HCl 193473-63-1 requires 2 additional equivalents of NEt₃ | (structure) | 58% |

Examples 1-18

Synthesis of the Compounds According to the Invention

Synthesis of Compound 1:

A solution of 910.4 mg (3 mmol) of 2-bromo-1,3-dipyridin-2-yl-1,3,2-diazaborolidine and 76.7 mg (0.6 mmol) of naphthalene in 50 ml of THF is cooled to −45° C. 209.2 mg (30 mmol) of lithium powder are added; the mixture is stirred with cooling for 24 h and subsequently filtered through Celite. The filtrate is added dropwise to a solution, cooled to −45° C., of 537.4 mg (1.0 mmol) of trispyridinoiridium trichloride in 25 mmol of THF; the cooling is removed, and the mixture is stirred at room temperature for 5 h. The volatile constituents are removed in a rotary evaporator, and the residue is suspended in 250 ml of warm heptane. After filtration through Celite, the volatile constituents are removed in a rotary evaporator, and the residue is recrystallised four times from toluene. Yield: 42% (363.1 mg, 0.4 mmol).

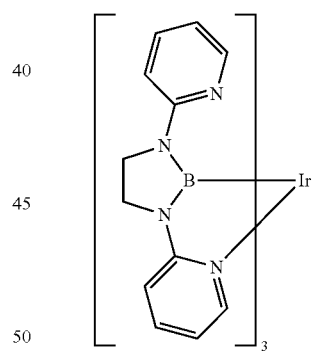

The following complex is prepared analogously to compound 1 from the corresponding 1,3,2-diazaborolidines:

| Comp. | 1,3,2-Diazaborolidine | Complex | Yield |
|---|---|---|---|
| 2 | (structure) | (structure) | 51% |

The following complexes are prepared analogously to compound 1 from the corresponding 1,3,2-diazaboroles:

| Comp. | 1,3,2-Diazaborole | Complex | Yield |
|---|---|---|---|
| 3 | | | 33% |
| 4 | | | 46% |

The following complexes are prepared analogously to compound 1 from the corresponding benzo-1,3,2-diazaboroles:

| Comp. | Benzo-1,3,2-diazaborole | Complex | Yield |
|---|---|---|---|
| 5 | | | 39% |

-continued

| Comp. | Benzo-1,3,2-diazaborole | Complex | Yield |
|---|---|---|---|
| 6 | | | 12% |
| 7 | | | 30% |
| 8 | | | 47% |

-continued
| Comp. | Benzo-1,3,2-diazaborole | Complex | Yield |
|---|---|---|---|
| 9 | 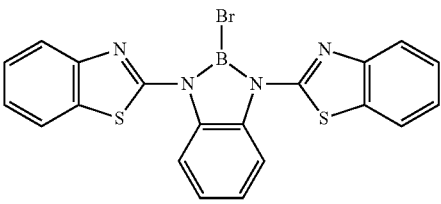 [SMILES: BrB1N(c2nc3ccccc3s2)c2ccccc2N1c1nc2ccccc2s1] | 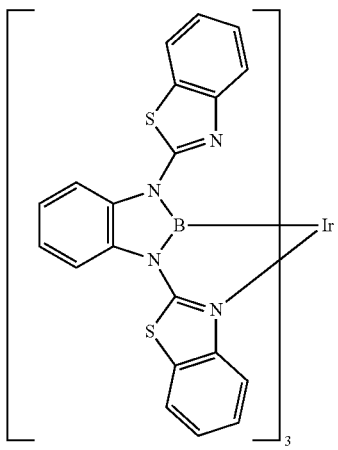 | 27% |
| 10 | 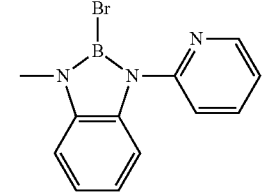 [SMILES: CN1B(Br)N(c2ccccn2)c2ccccc21] | 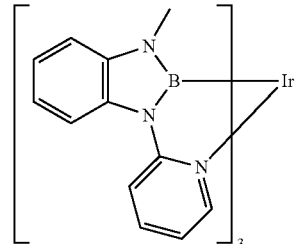 | 38% |
| 11 | 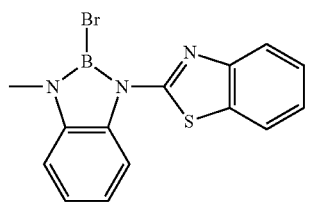 [SMILES: CN1B(Br)N(c2nc3ccccc3s2)c2ccccc21] | 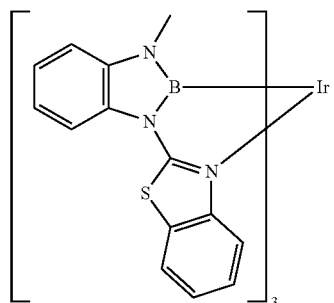 | 19% |
| 12 | 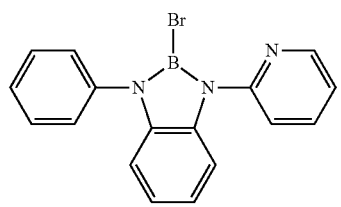 [SMILES: BrB1N(c2ccccc2)c2ccccc2N1c1ccccn1] | 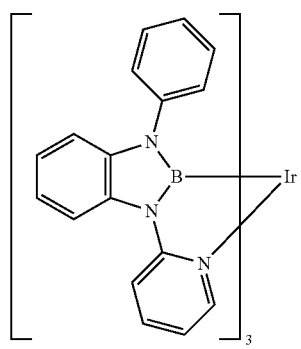 | 39% |

-continued
| Comp. | Benzo-1,3,2-diazaborole | Complex | Yield |
|---|---|---|---|
| 13 | 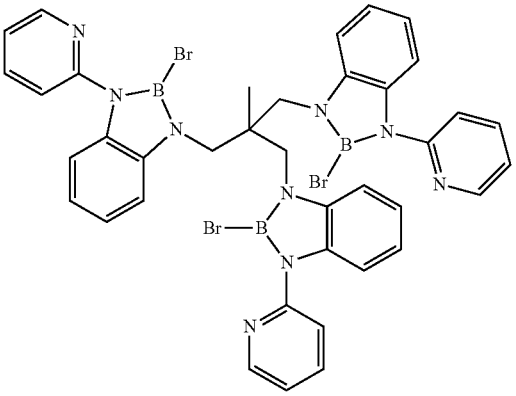 [SMILES: CC(CN1B(Br)N(c2ccccn2)c2ccccc21)(CN1B(Br)N(c2ccccn2)c2ccccc21)CN1B(Br)N(c2ccccn2)c2ccccc21] | 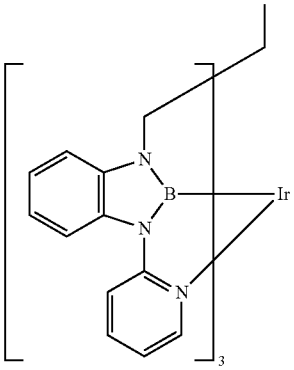 | 19% |
| 14 | 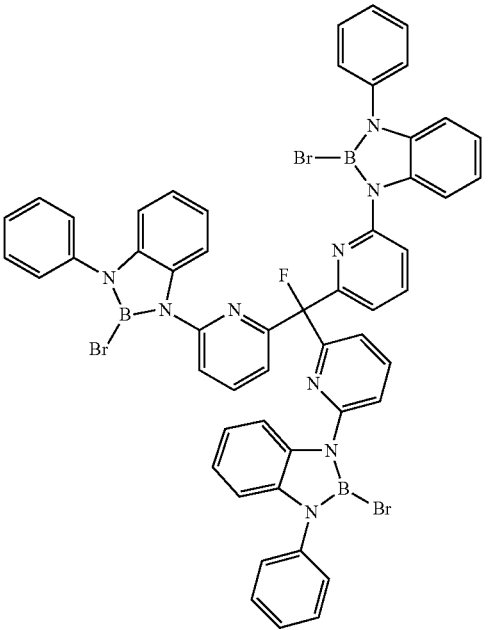 [SMILES: FC(c1cccc(N2B(Br)N(c3ccccc3)c3ccccc32)n1)(c1cccc(N2B(Br)N(c3ccccc3)c3ccccc32)n1)c1cccc(N2B(Br)N(c3ccccc3)c3ccccc32)n1] | 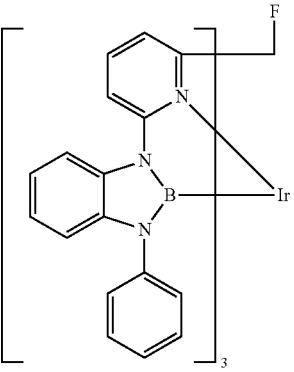 | 7% |
| 15 | 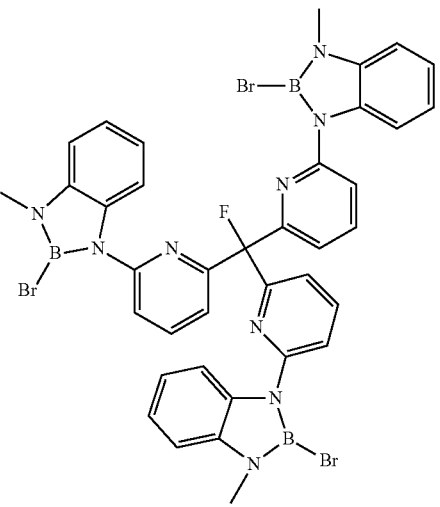 [SMILES: CN1B(Br)N(c2cccc(C(F)(c3cccc(N4B(Br)N(C)c5ccccc54)n3)c3cccc(N4B(Br)N(C)c5ccccc54)n3)n2)c2ccccc21] | 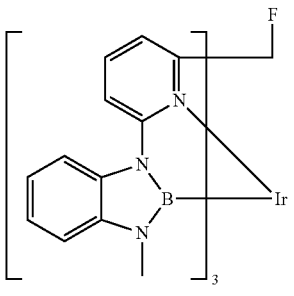 | 13% |

Compound 16 is prepared analogously to compound 1 from di-μ-chloro-tetrakis[2-(2-pyridinyl)phenyl-C,N]diiridium and 2-bromo-1-phenyl-3-pyridin-2-ylbenzo-1,3,2-diazaborole.

| Comp. | Metal comp. | Benzo-1,3,2-diazaborole | Complex | Yield |
|---|---|---|---|---|
| 16 | [structure] 92220-65-0 | [structure] | [structure] | 47% |

Compounds 17-18 are prepared analogously to compound 1 from corresponding 2-bromobenzo-1,3,2-diazaboroles and bis(benzonitrile)platinum dichloride.

| Comp. | Benzo-1,3,2-diazaborole | Complex | Yield |
|---|---|---|---|
| 17 | [structure] | [structure] | 34% |
| 18 | [structure] | [structure] | 39% |

Example 19

Synthesis of Compound 19 According to the Invention

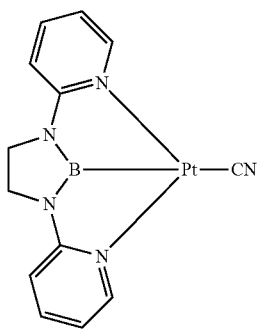

A solution of 606.4 mg (2.0 mmol) of 2-bromo-1,3-bis (pyridin-2-yl)-1,3,2-diazaborolidine and 76.6 mg (0.6 mmol) of naphthalene in 40 ml of THF is cooled to −45° C. 139.2 mg (20 mmol) of lithium powder are added; the mixture is stirred with cooling for 24 h and subsequently filtered through Celite. The filtrate is added dropwise to a solution, cooled to −45° C., of 746.9 mg (1.8 mmol) of potassium tetrachloroplatinate(II) in 35 mmol of THF, and the mixture is stirred at room temperature for 48 h. After the mixture has been filtered through Celite, 197.5 mg (3.0 mmol) of potassium cyanide are added to the solution, and the mixture is stirred for 24 h and again filtered through Celite. The volatile constituents are subsequently removed in a rotary evaporator. The residue is recrystallised twice from toluene. Yield: 21% (169.6 mg, 0.4 mmol).

Example 20

Production and Characterisation of Organic Electroluminescent Devices

Electroluminescent devices according to the invention can be produced as described, for example, in WO 05/003253. The results for various OLEDs are compared here. The basic structure, the materials used, the degree of doping and the layer thicknesses thereof are identical for better comparability.

The first device example describes a comparative standard in accordance with the prior art, in which the emission layer consists of the host material (or matrix M) bis-[1,3';1',1'';3'',1''';3''',1'''']quinquephenyl-5''-ylmethanone (in accordance with DE102008033943.1, Example 3) and the guest material (dopant) 10% fac-tris[2-(2-pyridinyl)(5-cyanophenyl)]iridium(III) (TEB) for blue emission. Furthermore, OLEDs having an identical structure and comprising dopants according to the invention are described. OLEDs having the following structure are produced analogously to the general process indicated above:

- Hole-injection layer (HIL) 20 nm of 2,2',7,7'-tetrakis(di-para-tolylamino)spiro-9,9'-bifluorene
- Hole-transport layer (HTL) 5 nm of NPB (N-naphthyl-N-phenyl-4,4'-diaminobiphenyl)
- Electron-blocking layer (EBL) 15 nm of EBL (9,9-bis-(3,5-diphenylaminophenyl)fluorene)
- Emission layer (EML) 40 nm of host material: bis-[1,3';1',1'';3'',1''';3''',1'''']quinquephenyl-5''-ylmethanone (M)
- Dopant: % by vol. doping; compounds see Table 1
- Hole-blocking layer (HBL) 10 nm: bis-[1,3';1,1'';3'',1''',3''',1'''']-quinquephenyl-5''-ylmethanone (M)
- Electron conductor (ETL) 20 nm of AlQ$_3$ (tris(quinolinato) aluminium(III))
- Cathode 1 nm of LiF, 100 nm of Al on top.

The structures of EBL, M and TEB are depicted below for clarity.

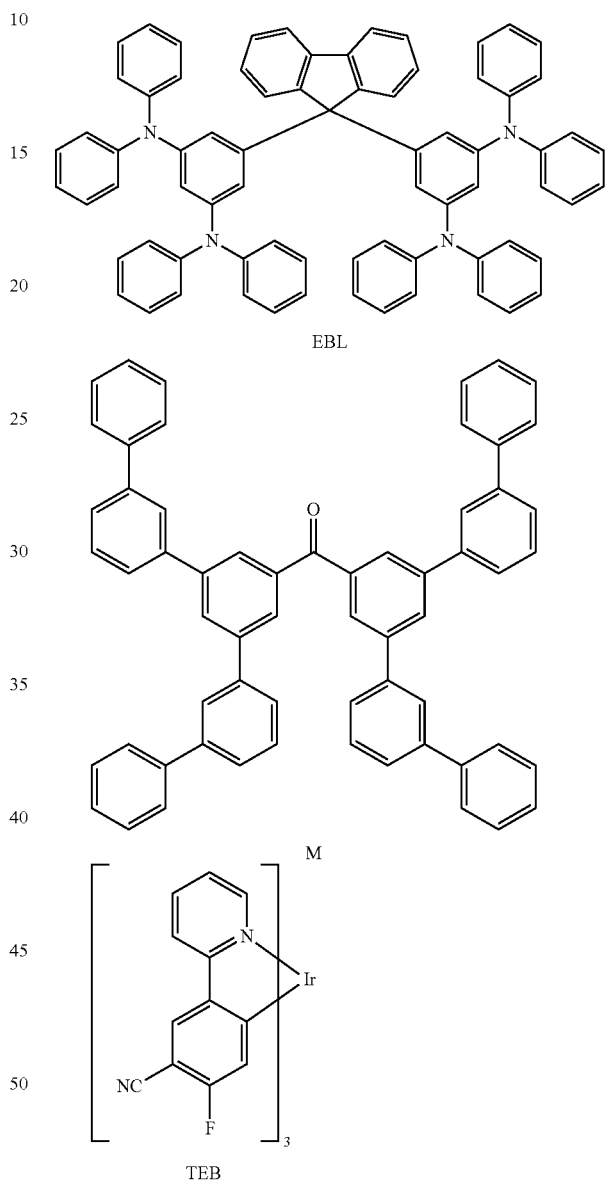

The dopants according to the invention used are compounds 1-19 described above.

These as yet unoptimised OLEDs are characterised by standard methods; for this purpose, the electroluminescence spectra, the external quantum efficiency (measured in %) as a function of the luminance, calculated from current-voltage-brightness characteristic lines (IUL characteristic lines), and the lifetime are determined.

As can be seen from Table 1, the devices exhibit superior behaviour in the measured external quantum efficiencies (EQEs), voltages and emission maxima compared with the prior art comprising the dopant TEB.

TABLE 1

Device results with compounds according to the invention

| Ex. | Dopant/ % by vol. | EQE at 100 cd/m² [%] | Voltage at 100 cd/m² [V] | λ max [nm] |
|---|---|---|---|---|
| 20 (comparison) | TEB/10% | 9.2 | 6.8 | 462 |
| 21 | Comp. 1/20% | 8.0 | 6.7 | 443 |
| 22 | Comp. 2/10% | 11.3 | 5.5 | 441 |
| 23 | Comp. 3/20% | 7.8 | 6.5 | 476 |
| 24 | Comp. 4/20% | 6.7 | 5.8 | 469 |
| 25 | Comp. 5/20% | 7.0 | 5.9 | 452 |
| 26 | Comp. 6/20% | 3.4 | 11.3 | 445 |
| 27 | Comp. 7/20% | 5.4 | 8.3 | 438 |
| 28 | Comp. 8/20% | 5.5 | 7.4 | 454 |
| 29 | Comp. 9/20% | 6.3 | 5.3 | 444 |
| 30 | Comp. 10/10% | 10.9 | 5.7 | 449 |
| 31 | Comp. 11/20% | 8.0 | 6.0 | 441 |
| 32 | Comp. 12/20% | 7.7 | 6.4 | 450 |
| 33 | Comp. 13/20% | 8.1 | 6.5 | 448 |
| 34 | Comp. 14/20% | 7.9 | 6.6 | 447 |
| 35 | Comp. 15/20% | 7.9 | 6.3 | 445 |
| 36 | Comp. 16/20% | 12.0 | 5.4 | 524 |
| 37 | Comp. 17/20% | 10.1 | 7.1 | 462 |
| 38 | Comp. 18/20% | 9.8 | 7.5 | 460 |
| 39 | Comp. 19/10% | 10.2 | 6.7 | 457 |

The invention claimed is:

1. An electronic device comprising a compound of formula (I)

where said compound of formula (I) comprises a moiety $M(L)_n$ of formula (II) and/or (III) and/or (IV):

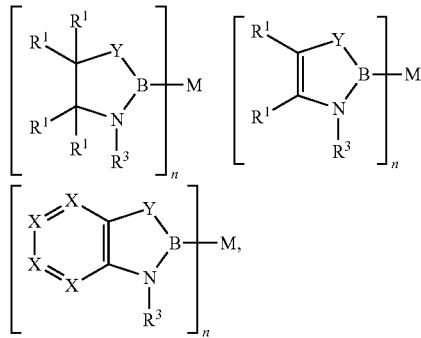

wherein
M is a metal;
Y is on each occurrence, in each case independently of one another, $NR^3$, O or S;
X is on each occurrence, in each case independently of one another, $CR^1$ or N;
$R^1$ is on each occurrence, in each case independently of one another, H, D, F, Cl, Br, I, CHO, $N(R^2)_2$, $N(Ar)_2$, $C(=O)$Ar, $P(=O)(Ar)_2$, $S(=O)Ar$, $S(=O)_2Ar$, $CR^2=C(R^2)_2$, $CR^2=CR^2Ar$, CN, $NO_2$, $Si(R^3)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which are optionally substituted by one or more radicals $R^2$, wherein one or more non-adjacent $CH_2$ groups are optionally replaced by $R^2C=CR^2$, $C≡C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and wherein one or more H atoms are optionally replaced by D, F, Cl, Br, I, CN or $NO_2$, or an aromatic or heteroaromatic ring system having 5 to 60 aromatic ring atoms, which in each case are optionally substituted by one or more radicals $R^2$, or an aryloxy or heteroaryloxy group having 5 to 60 aromatic ring atoms, which is optionally substituted by one or more radicals $R^2$, or a combination of these systems, and wherein two or more adjacent substituents $R^1$ optionally define a mono- or polycyclic, aliphatic or aromatic ring system with one another;

$R^2$ is on each occurrence, in each case independently of one another, H, D, F or an aliphatic, aromatic and/or heteroaromatic hydrocarbon radical having 1 to 20 C atoms, in which, in addition, one or more H atoms are optionally replaced by F; and wherein two or more substituents $R^2$ optionally define a mono- or polycyclic, aliphatic or aromatic ring system with one another;

$R^3$ is on each occurrence, in each case independently of one another, H, D, an aliphatic hydrocarbon radical having 1 to 20 C atoms or an aromatic or heteroaromatic ring system having 5 to 30 aromatic ring atoms, which is optionally substituted by one or more radicals $R^1$; or $R^3$ is a coordinating group, wherein $R^3$ bonds to the metal M via a charged or uncharged exocyclic or endocyclic donor atom D;

a plurality of part-ligands L here may form a polydentate or polypodal ligand with one another or L together with L' and/or L", optionally via a link via $R^3$;

Ar is on each occurrence, in each case independently of one another, an aromatic or heteroaromatic ring system having 5 to 30 aromatic ring atoms, which is optionally substituted by one or more non-aromatic radicals $R^1$;

L' and L"
are any desired co-ligands; and
wherein
n is 1, 2, 3, 4, 5, or 6, o is 0, 1, 2, 3, 4, or 5, and m is 0, 1, 2, 3, 4, or 5, if M has the coordination number 6,
n is 1, 2, 3, 4, or 5, o is 0, 1, 2, 3, or 4 and m is 0, 1, 2, 3, or 4, if M has the coordination number 5, and
n is 1, 2, 3, or 4, m is 0, 1, 2, or 3, and o is 0, 1, 2, or 3, if M has the coordination number 4.

2. The electronic device of claim 1, wherein said device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic photoreceptors and organic laser diodes.

3. The electronic device of claim 1, wherein moiety $M(L)_n$ of formula (II), (III), and/or (IV) conforms to formula (IIa), (IIIa), (IVa), (IIb), (IIIb), or (IVb):

formula IIa

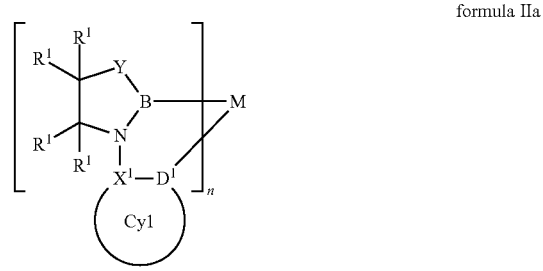

-continued formula IIIa

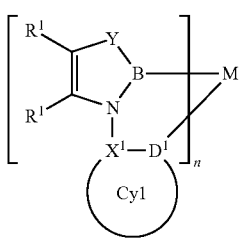

formula IVa

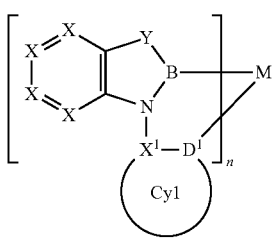

formula IIb

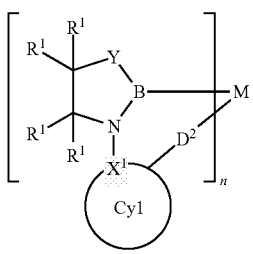

formula IIIb

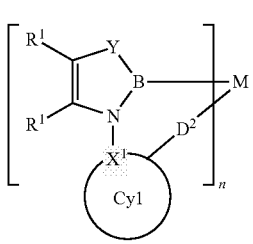

formula IVb

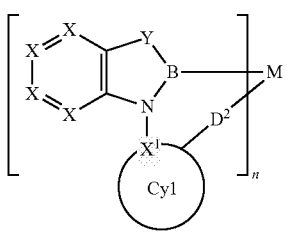

wherein
- $D^1$ is on each occurrence, in each case independently of one another, an endocyclic donor atom selected from the group consisting of B, C, N, O and S;
- $D^2$ is on each occurrence, in each case independently of one another, an exocyclic donor group selected from the group consisting of O, S, $NR^1$, $N(R^1)_2$, $PR^1$, $P(R^1)_2$, $P(O)R^1$, $P(O)(R^1)_2$, $AsR^1$, $As(R^1)_2$, $As(O)R^1$, $As(O)(R^1)_2$, $SbR^1$, $Sb(R^1)_2$, $Sb(O)R^1$, $Sb(O)(R^1)_2$, $BiR^1$, $Bi(R^1)_2$, $Bi(O)R^1$, $Bi(O)(R^1)_2$, $OR^1$, $SR^1$, $SeR^1$ and $TeR^1$;
- $X^1$ is on each occurrence, in each case independently of one another, C or N;
- Cy1 is an aromatic or heteroaromatic group or an aromatic or heteroaromatic ring system having 5 to 30 ring atoms, where $X^1$ and $D^1$ are present in the aromatic or heteroaromatic group or the aromatic or heteroaromatic ring system, and $D^2$ is bonded as an exocyclic donor atom or exocyclic donor group.

4. The electronic device of claim 1, wherein $D^1$ is on each occurrence, in each case independently of one another, N, O or S, and $D^2$ is on each occurrence, in each case independently of one another, O, S, $NR^1$, $N(R^1)_2$, $PR^1$, or $P(R^1)_2$.

5. The electronic device of claim 1, wherein Y is $NR^3$.

6. The electronic device of claim 1, wherein $R^3$ in formula II, III or IV or Cy1 in the formulae IIa, IIIa, IVa, IIb, IIIb, and IVb is selected from structures (1) to (24):

(1)

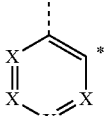

(2)

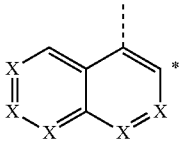

(3)

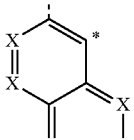

(4)

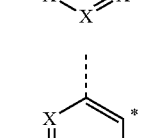

(5)

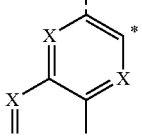

(6)

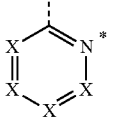

(7)

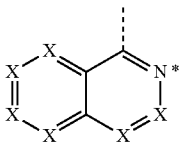

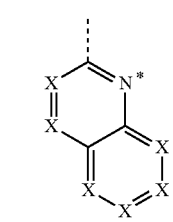

-continued (8) 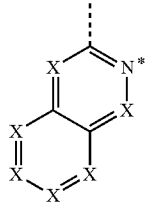

(9) 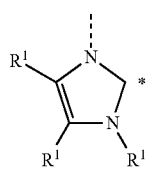

(10) 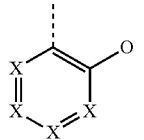

(11) 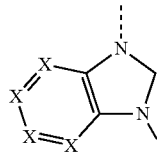

(12) 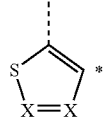

(13) 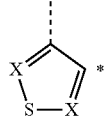

(14) 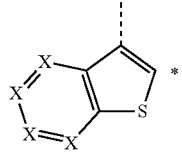

(15) 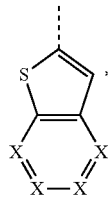

(16) 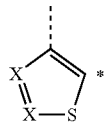

-continued

(17) 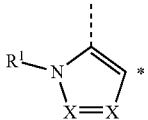

(18) 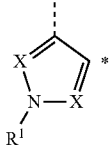

(19) 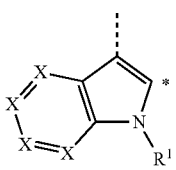

(20) 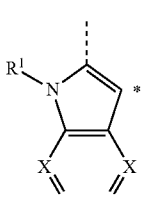

(21) 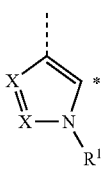

(22) 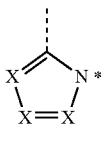

(23) 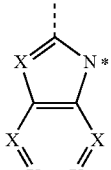

(24) 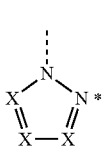

wherein

X is on each occurrence, in each case independently of one another, $CR^1$ or N, the dashed line denotes a bond to the nitrogen atom of the boron/nitrogen heterocycle, and \* indicates the position at which the group coordinates to the metal.

7. The electronic device of claim 1, wherein the moiety $M(L)_n$ is selected from formulae (IIc), (IIIc), and/or (IVc):

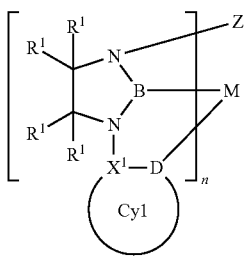
formula IIc

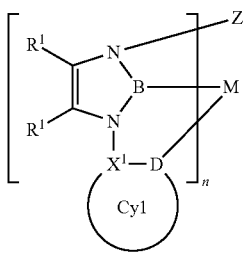</br>
formula IIIc

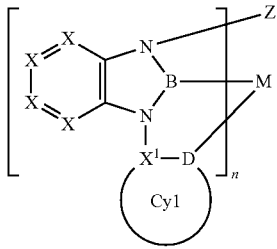</br>
formula IVc wherein

Z is any desired bridging unit.

8. The electronic device of claim 1, wherein the compound of formula (I) comprises only ligands L or wherein the compound of formula (I) is hexacoordinated and comprises two or three bidentate ligands L or two tridentate ligands L or wherein the compound of formula (I) is coordinated in a square-planar or tetrahedral manner and comprises one or two bidentate ligands L or one tetradentate ligand L.

9. A compound of formula (I)

$$M(L)_n(L')_m(L'')_o \qquad (I)$$

wherein said compound of formula (I) comprises a moiety $M(L)_n$ of formula (II), (III) and/or (IV):

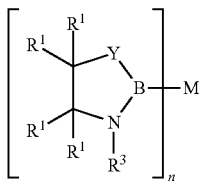</br>
formula II

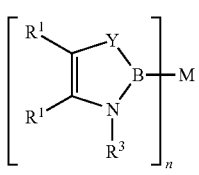</br>
formula III

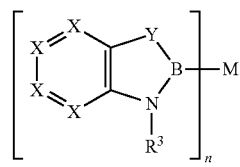</br>
formula IV wherein

M is a metal;

Y is on each occurrence, in each case independently of one another, $NR^2$, O or S;

X is on each occurrence, in each case independently of one another, $CR^1$ or N;

$R^1$ is on each occurrence, in each case independently of one another, H, D, F, Cl, Br, I, CHO, $N(Ar)_2$, $C(=O)Ar$, $P(=O)(Ar)_2$, $S(=O)Ar$, $S(=O)_2Ar$, $CR^2=C(R^2)_2$, $CR^2=CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, wherein one or more non-adjacent $CH_2$ groups are optionally replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and wherein one or more H atoms are optionally replaced by D, F, Cl, Br, I, CN, or $NO_2$, or an aromatic or heteroaromatic ring system having 5 to 60 aromatic ring atoms, which in each case is optionally substituted by one or more radicals $R^2$, or an aryloxy or heteroaryloxy group having 5 to 60 aromatic ring atoms, which is optionally substituted by one or more radicals $R^2$, or a combination of these systems, wherein two or more adjacent substituents $R^1$ optionally define a mono- or polycyclic, aliphatic or aromatic ring system with one another;

$R^2$ is on each occurrence, in each case independently of one another, H, D, F or an aliphatic, aromatic and/or heteroaromatic hydrocarbon radical having 1 to 20 C atoms, in which, in addition, one or more H atoms are optionally replaced by F, and wherein two or more substituents $R^2$ optionally define a mono- or polycyclic, aliphatic or aromatic ring system with one another;

$R^3$ is on each occurrence, in each case independently of one another, an aliphatic hydrocarbon radical having 1 to 20 C atoms or an aromatic or heteroaromatic ring system having 5 to 30 aromatic ring atoms, which is optionally substituted by one or more radicals $R^1$; at least one radical $R^3$ here is a coordinating group which bonds to the metal M via a charged or uncharged exocyclic or endocyclic donor atom D;

a plurality of part-ligands L here may form a polydentate or polypodal ligand with one another or L together with L' and/or L", optionally via a link via $R^3$;

Ar is on each occurrence, in each case independently of one another, an aromatic or heteroaromatic ring system having 5 to 30 aromatic ring atoms, which is optionally substituted by one or more non-aromatic radicals $R^1$; and L' and L"

are any desired co-ligands; and wherein n is 1, 2, 3, 4, 5, or 6, o is 0, 1, 2, 3, 4, or 5, and m is 0, 1, 2, 3, 4, or 5, if M has the coordination number 6, n is 1, 2, 3, 4, or 5, o is 0, 1, 2, 3, or 4 and m is 0, 1, 2, 3, or 4, if M has the coordination number 5, and n is 1, 2, 3, or 4, m is 0, 1, 2, or 3, and o is 0, 1, 2, or 3, if M has the coordination number 4.

10. The compound of claim 9, wherein the moiety $M(L)_n$ conforms to formula (IIa), (IIIa), (IVa), (IIb), (IIIb), or (IVb):

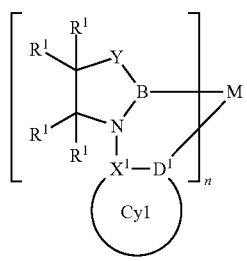

formula IIa

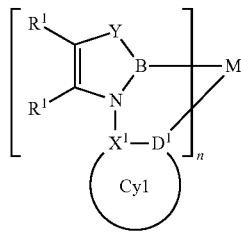

formula IIIa

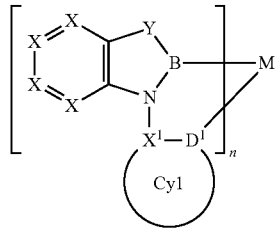

formula IVa

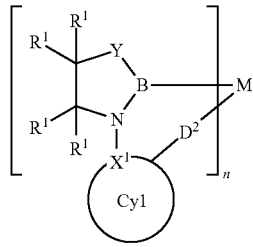

formula IIb

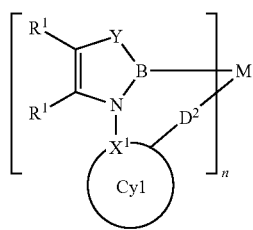

formula IIIb

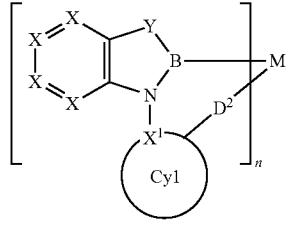

formula IVb $D^1$ is on each occurrence, in each case independently of one another, an endocyclic donor atom selected from the group consisting of B, C, N, O, and S;

$D^2$ is on each occurrence, in each case independently of one another, an exocyclic donor group selected from the group consisting of O, S, $NR^1$, $N(R^1)_2$, $PR^1$, $P(R^1)_2$, $P(O)R^1$, $P(O)(R^1)_2$, $AsR^1$, $As(R^1)_2$, $As(O)R^1$, $As(O)(R^1)_2$, $SbR^1$, $Sb(R^1)_2$, $Sb(O)R^1$, $Sb(O)(R^1)_2$, $BiR^1$, $Bi(R^1)_2$, $Bi(O)R^1$, $Bi(O)(R^1)_2$, $OR^1$, $SR^1$, $SeR^1$, and $TeR^1$;

$X^1$ is on each occurrence, in each case independently of one another, C or N;

Cy1 is an aromatic or heteroaromatic group or an aromatic or heteroaromatic ring system having 5 to 30 ring atoms, where $X^1$ and $D^1$ are present in the aromatic or heteroaromatic group or the aromatic or heteroaromatic ring system, and $D^2$ is bonded as an exocyclic donor atom or exocyclic donor group.

11. The compound of claim 9, wherein $R^3$ or Cy1 is selected from structures (1) to (24):

(1)

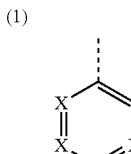

(2)

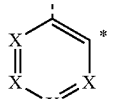

(3)

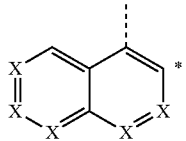

(4)

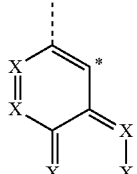

(5)

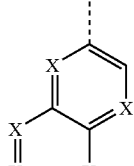

(6)

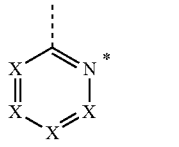

(7) 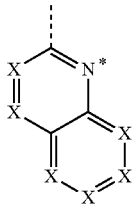
(8) 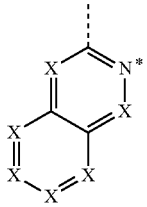
(9) 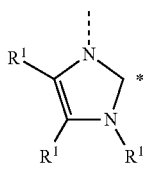
(10) 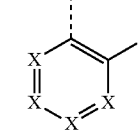
(11) 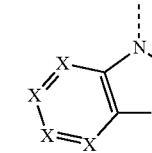
(12) 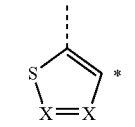
(13) 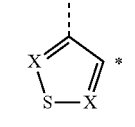
(14) 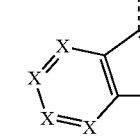
(15) 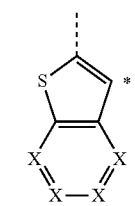
(16) 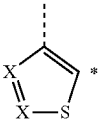
(17) 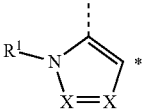
(18) 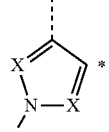
(19) 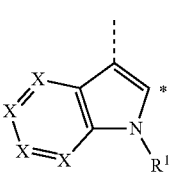
(20) 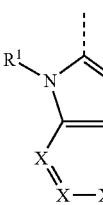
(21) 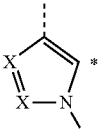
(22) 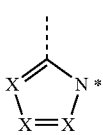
(23) 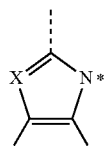
(24) 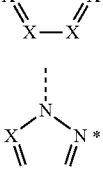
wherein
X is on each occurrence, in each case independently of one another, $CR^1$ or N, the dashed line denotes a bond to the nitrogen atom of the boron/nitrogen heterocycle, and

* indicates the position at which the group coordinates to the metal.

12. The compound of claim 9, wherein the moiety $M(L)_n$ is selected from formulae (IIc), (IIIc), and (IVc):

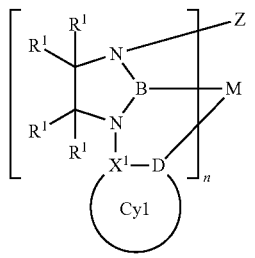

formula IIc

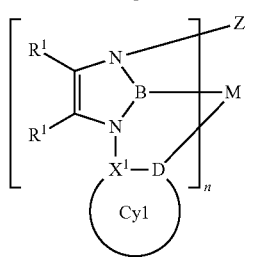

formula IIIc

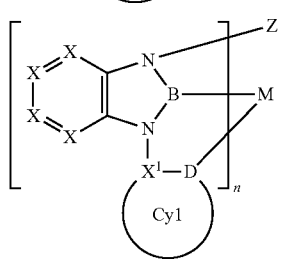

formula IVc wherein
Z is any desired bridging unit.

13. The electronic device of claim 1, wherein said compound of formula (I) is an emitter compound, a matrix material, a hole-blocking material, and/or an electron-transport material.

14. A compound of formula (V), (VI), or (VII):

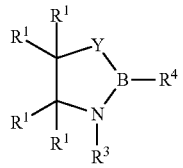

formula V

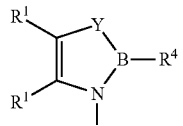

formula VI

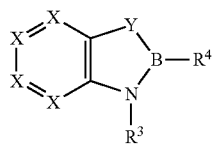

formula VII wherein
Y is on each occurrence, in each case independently of one another, $NR^2$, O or S;

X is on each occurrence, in each case independently of one another, $CR^1$ or N;

$R^1$ is on each occurrence, in each case independently of one another, H, D, F, Cl, Br, I, CHO, $N(Ar)_2$, $C(=O)Ar$, $P(=O)(Ar)_2$, $S(=O)Ar$, $S(=O)_2Ar$, $CR^2=C(R^2)_2$, $CR^2=CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, wherein one or more non-adjacent $CH_2$ groups are optionally replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and wherein one or more H atoms are optionally replaced by D, F, Cl, Br, I, CN, or $NO_2$, or an aromatic or heteroaromatic ring system having 5 to 60 aromatic ring atoms, which in each case is optionally substituted by one or more radicals $R^2$, or an aryloxy or heteroaryloxy group having 5 to 60 aromatic ring atoms, which is optionally substituted by one or more radicals $R^2$, or a combination of these systems, wherein two or more adjacent substituents $R^1$ optionally define a mono- or polycyclic, aliphatic or aromatic ring system with one another;

$R^2$ is on each occurrence, in each case independently of one another, H, D, F or an aliphatic, aromatic and/or heteroaromatic hydrocarbon radical having 1 to 20 C atoms, in which, in addition, one or more H atoms are optionally replaced by F, and wherein two or more substituents $R^2$ optionally define a mono- or polycyclic, aliphatic or aromatic ring system with one another;

$R^3$ is selected from structures (1) to (24):

(1)

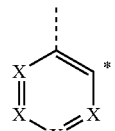

(2)

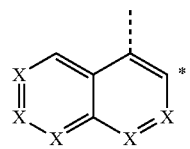

(3)

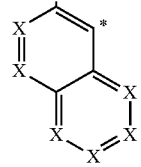

(4)

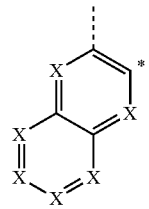

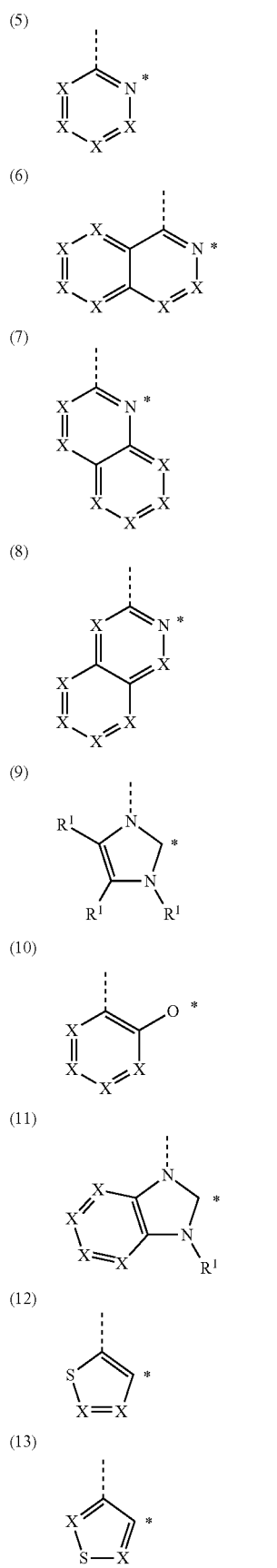
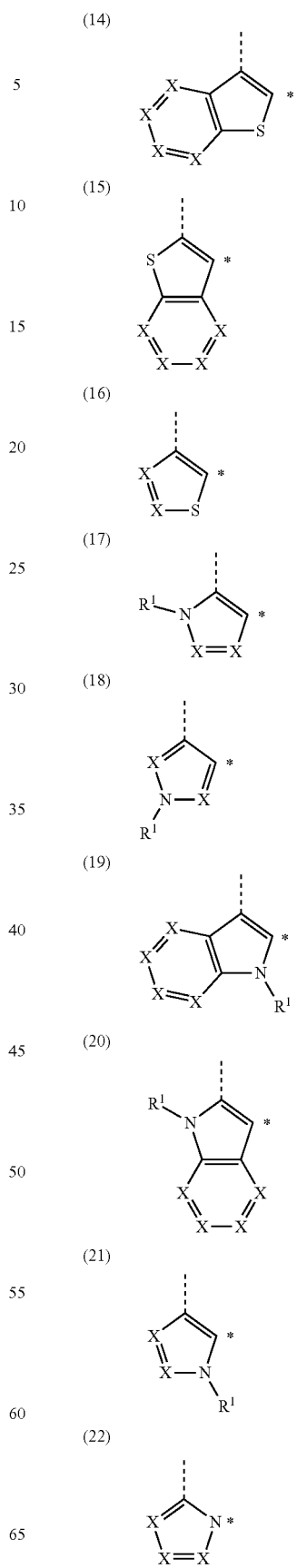

-continued

(23)
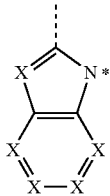

(24)
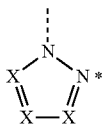

wherein

X is on each occurrence, in each case independently of one another, $CR^1$ or N, the dashed line denotes a bond to the nitrogen atom of the boron/nitrogen heterocycle, and \* indicates the position at which the group coordinates to the metal;

Ar is on each occurrence, in each case independently of one another, an aromatic or heteroaromatic ring system having 5 to 30 aromatic ring atoms, which is optionally substituted by one or more non-aromatic radicals $R^1$; and $R^4$ is H or halogen;

with the proviso that the following compounds are excluded:

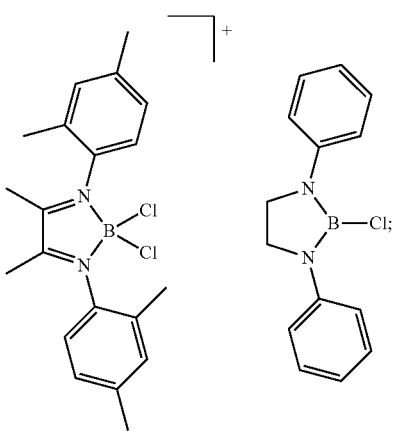

and wherein, if the compound is a compound according to Formula (VI), $R^3$ is not structure (1).

15. A process for preparing the compound of claim 9 comprising reacting a compound of formula (V), (VI), or (VII):

formula V
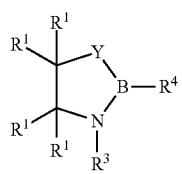

-continued formula VI
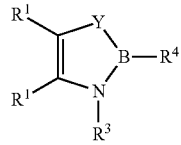

formula VII
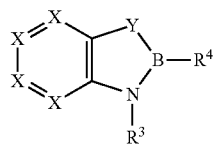

wherein

Y is on each occurrence, in each case independently of one another, $NR^2$, O or S;

X is on each occurrence, in each case independently of one another, $CR^1$ or N;

$R^1$ is on each occurrence, in each case independently of one another, H, D, F, Cl, Br, I, CHO, $N(Ar)_2$, $C(=O)Ar$, $P(=O)(Ar)_2$, $S(=O)Ar$, $S(=O)_2Ar$, $CR^2=C(R^2)_2$, $CR^2=CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, wherein one or more non-adjacent $CH_2$ groups are optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and wherein one or more H atoms are optionally replaced by D, F, Cl, Br, I, CN, or $NO_2$, or an aromatic or heteroaromatic ring system having 5 to 60 aromatic ring atoms, which in each case is optionally substituted by one or more radicals $R^2$, or an aryloxy or heteroaryloxy group having 5 to 60 aromatic ring atoms, which is optionally substituted by one or more radicals $R^2$, or a combination of these systems, wherein two or more adjacent substituents $R^1$ optionally define a mono- or polycyclic, aliphatic or aromatic ring system with one another;

$R^2$ is on each occurrence, in each case independently of one another, H, D, F or an aliphatic, aromatic and/or heteroaromatic hydrocarbon radical having 1 to 20 C atoms, in which, in addition, one or more H atoms are optionally replaced by F, and wherein two or more substituents $R^2$ optionally define a mono- or polycyclic, aliphatic or aromatic ring system with one another;

$R^3$ is selected from structures (1) to (24):

(1)
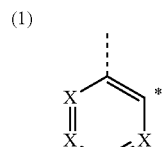

(2)
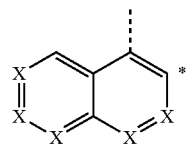

(3) 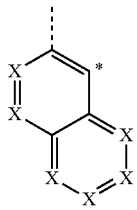
(4) 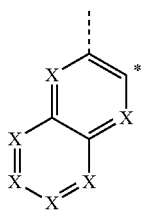
(5) 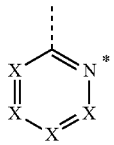
(6) 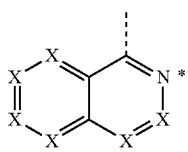
(7) 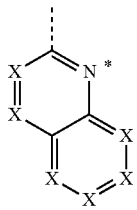
(8) 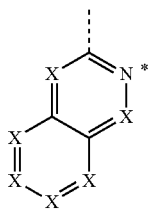
(9) 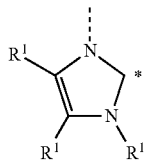
(10) 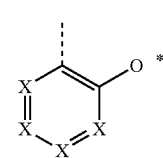
(11) 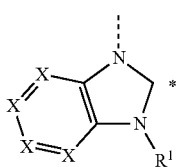
(12) 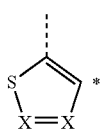
(13) 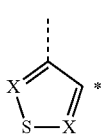
(14) 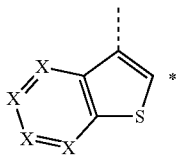
(15) 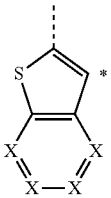
(16) 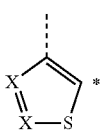
(17) 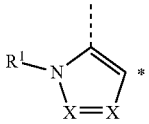
(18) 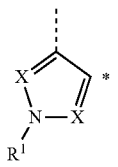
(19) 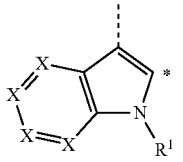

(20)

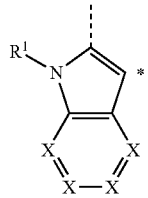

(21)

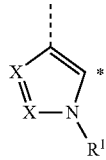

(22)

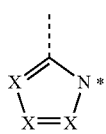

(23)

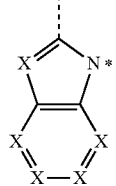

(24)

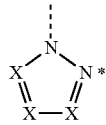

wherein
X is on each occurrence, in each case independently of one another, CR¹ or N,
the dashed line denotes a bond to the nitrogen atom of the boron/nitrogen heterocycle, and
* indicates the position at which the group coordinates to the metal;
Ar is on each occurrence, in each case independently of one another, an aromatic or heteroaromatic ring system having 5 to 30 aromatic ring atoms, which is optionally substituted by one or more non-aromatic radicals R¹; and
R⁴ is H or halogen;
with the proviso that the following compounds are excluded:

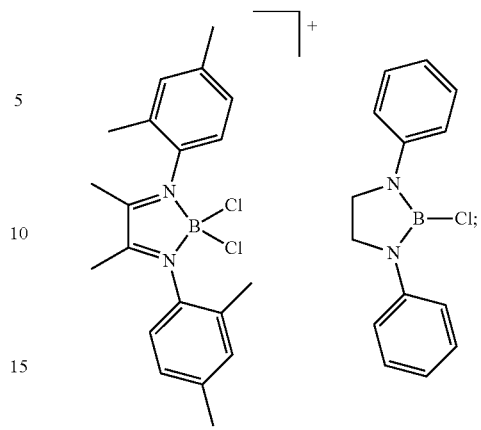

with a metal alkoxide of formula (47), a metal ketoketonate of formula (48) or a metal halide of formula (49):

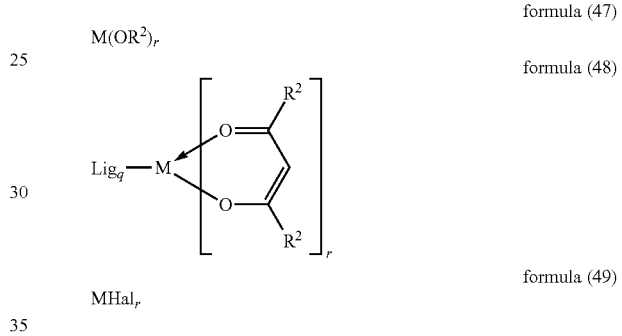

wherein
M is a metal;
R² is on each occurrence, in each case independently of one another, H, D, F or an aliphatic, aromatic and/or heteroaromatic hydrocarbon radical having 1 to 20 C atoms, in which, in addition, one or more H atoms are optionally replaced by F; and wherein two or more substituents R² optionally define a mono- or polycyclic, aliphatic or aromatic ring system with one another;
Hal is on each occurrence, identically or differently, F, Cl, Br or I;
Lig is on each occurrence, identically or differently, a neutral or monoanionic, monodentate or bidentate ligand;
q is on each occurrence, identically or differently, 0, 1, 2, 3 or 4, preferably 0, 1 or 2;
r is on each occurrence, identically or differently, 1, 2, 3, 4 or 5;
wherein the metal ketoketonate of formula (48) and the metal halide of formula (49) is optionally charged and comprises one or more counterions; and
wherein the metal alkoxide of formula (47), the metal ketoketonate of formula (48), and the metal halide of formula (49) are optionally in the form of the hydrate.

* * * * *